US008710199B2

(12) United States Patent
Han et al.

(10) Patent No.: US 8,710,199 B2
(45) Date of Patent: Apr. 29, 2014

(54) SIGNAL ACTIVATED MOLECULAR DELIVERY

(75) Inventors: Si-Ping Han, Yorba Linda, CA (US); William A. Goddard, III, Pasadena, CA (US); Lisa Scherer, Monrovia, CA (US); John J. Rossi, Alta Loma, CA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 19 days.

(21) Appl. No.: 13/167,672

(22) Filed: Jun. 23, 2011

(65) Prior Publication Data

US 2012/0022146 A1    Jan. 26, 2012

Related U.S. Application Data

(60) Provisional application No. 61/357,917, filed on Jun. 23, 2010.

(51) Int. Cl.
*C07H 21/00* (2006.01)
*C12N 15/113* (2010.01)

(52) U.S. Cl.
USPC ........................................ 536/22.1; 514/44 A

(58) Field of Classification Search
None
See application file for complete search history.

(56) References Cited

U.S. PATENT DOCUMENTS

| 2006/0088864 A1 | 4/2006 | Smolke et al. |
| 2009/0082217 A1 | 3/2009 | Smolke et al. |
| 2009/0234109 A1 | 9/2009 | Han et al. |

FOREIGN PATENT DOCUMENTS

| WO | WO 2007-107162 | 9/2007 |
| WO | WO 2011-163526 | 12/2011 |

OTHER PUBLICATIONS

PCT International Search Report mailed on Jul. 9, 2013 for PCT Application No. PCT/US2013/033380 filed Mar. 21, 2013 in the name of California Institute of Technology et al.
PCT Written Opinion mailed on Jul. 9, 2013 for PCT Application No. PCT/US2013/033380 filed Mar. 21, 2013 in the name of California Institute of Technology et al.
De Paula, D. et al. "Hydrophobization and bioconjugation for enhanced siRNA delivery and targeting." RNA, vol. 13, pp. 431-456, 2007.
Kim, J. et al. "Intracellular small interfering RNA delivery using genetically engineered double-stranded RNA binding protein domain." The Journal of Gene Medicine. vol. 11, pp. 804-812, 2009.
Wang, H.W. et al. "Structural Insights into RNA Processing by the Human RISC-Loading Complex." Nat Struct Mol Biol., vol. 16(1), pp. 1148-1153, 2009.

Mathews, D.H. et al. "Folding and Finding RNA Secondary Structure." Cold Spring Harbor Perspectives in Biology. 2010.
Wu, H., et al., Properties of cloned and expressed human RNase H1, *The Journal of Biological Chemistry*, 1999, vol. 274, pp. 28270-28278.
Zamaratski, E., et al., A critical survey of the structure-function of the antisense oligo/RNA heteroduplex as substrate for RNase H, *Journal of Biochemical and Biophysical Methods*, 2001, vol. 48, pp. 189.
Cazenave, C., et al., Characterization and subcellular localization of ribonuclease Activities From Xenopus laevia oocytes, *The Journal of Biological Chemistry*, 1994, vol. 269, pp. 25185.
Nowotny, M., et al. Crystal structures of RNase H bound to an RNA/DNA hybrid: substrate spaecificity and metal-dependent catalysis, *Cell*, 2005, vol. 121, pp. 1005.
Song, J. J. et al., "The crystal structure of the Argonaute2 PAZ domain reveals an RNA binding motif in RNAi effector complexes", *Nature Structural Biology*, vol. 10, pp. 1026 (2003).
Ma, J. B. et al., "Structural basis for overhang-specific small interfering RNA recognition by the PAZ domain", *Nature*, vol. 429, pp. 318 (2004).
Yan, K. S. et al., "Structure and conserved RNA binding of the PAZ domain", *Nature*, vol. 426, pp. 468 (2003).
Lingel, A. et al., "Structure and nucleic-acid binding of the Drosophila Argonaute 2 PAZ domain", *Nature*, vol. 426, pp. 465 (2003).
Behlke, M. A. et al., "Chemical modification of siRNAs for in vivo use", *Oligonucleotides*, vol. 18, pp. 305 (2008).
Rose, S. D. et al., "Functional polarity is introduced by Dicer processing of short substrate RNAs", *Nucleic Acids Research*, vol. 33, pp. 4140 (2005).
Tomari, Y., et al., "A Protein Sensor for siRNA Asymmetry", *Science*, vol. 306, pp. 1377, (2004).
Susan M. Freier and Karl-Heinz Altman, The ups and downs of nucleic acid duplex stability: structure-stability studies on chemically-modified DNA:RNA duplexes, *Nucleic Acids Research*, 1997, vol. 25, No. 22 4429-4443.
Majlessi, M. et al. Advantages of 2'-O-methyl oligoribonucleotide probes for detecting RNA targets *Nucleic Acids Research*, 1998, vol. 26, No. 9, pp. 2224-2229.
Kierzek, E. et al. The influence of locked nucleic acid residues on the thermodynamic properties of 2'-O-methyl RNA/RNA heteroduplexes *Nucleic Acids Research*, 2005, vol. 33, No. 16, pp. 5082-5093.
Yakovchuk, P. et al. Base-stacking and base-pairing contributions into thermal stability of the DNA double helix *Nucleic Acids Research*, 2006, vol. 34, No. 2, pp. 564-574.
Han, H. et al. Sequence-specific recognition of double helical RNA and RNA.DNA by triple helix formation, *PNAS* May 1, 1993 vol. 90, pp. 3806-3810.

(Continued)

*Primary Examiner* — Tracy Vivlemore
(74) *Attorney, Agent, or Firm* — Steinfl & Bruno LLP

(57) ABSTRACT

Provided herein are signal activatable molecular constructs for enzyme-assisted delivery of molecules and related components, such as a sensor domain, compositions, methods and systems.

33 Claims, 33 Drawing Sheets

(56) References Cited

OTHER PUBLICATIONS

Burge S, Parkinson GN, Hazel P, Todd AK, Neidle S (2006). "Quadruplex DNA: sequence, topology and structure". *NAR* 34 (19): 5402-5415. doi:10.1093/nar/gkl655.

J.N. Zadeh, C.D. Steenberg, J.S. Bois, B.R. Wolfe, M.B. Pierce, A.R. Khan, R.M. Dirks, N.A. Pierce. NUPACK: analysis and design of nucleic acid systems. *J Comput Chem*, 32, 170-173, 2011.

R.M. Dirks, J.S. Bois, J.M. Schaeffer, E. Winfree, and N.A. Pierce. (2007) Thermodynamic analysis of interacting nucleic acid strands. *SIAM Rev*, 49, 65-88.

R.M. Dirks and N.A. Pierce. (2003) A partition function algorithm for nucleic acid secondary structure including pseudoknots. *J Comput Chem*, 24, 1664-1677.

R.M. Dirks and N.A. Pierce. (2004) An algorithm for computing nucleic acid base-pairing probabilities including pseudoknots. *J Comput Chem*, 25, 1295-1304.

J.N. Zadeh, B.R. Wolfe, N.A. Pierce. Nucleic acid sequence design via efficient ensemble defect optimization. *J Comput Chem*, 32, 439-452, 2011.

M. Zuker. Mfold web server for nucleic acid folding and hybridization prediction. *Nucleic Acids Res.* 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major. RNAML: A standard syntax for exchanging RNA information. *RNA* 8 (6), 707-717, 2002.

Zuker & A. B. Jacobson. Using Reliability Information to Annotate RNA Secondary Structures. *RNA* 4, 669-679, 1998. [Abstract][Preprint] Note: Explains color annotation of secondary structure.

N. R. Markham & M. Zuker. UNAFold: Software for Nucleic Acid Folding and Hybridization. In Data, Sequence Analysis, and Evolution, J. Keith, ed., *Bioinformatics*: vol. 2, Chapter 1, pp. 3-31, Humana Press Inc., 2008.

M. Zuker, D. H. Mathews & D. H. Turner. Algorithms and Thermodynamics for RNA Secondary Structure Prediction: A Practical Guide in RNA Biochemistry and Biotechnology,11-43, J. Barciszewski and B. F. C. Clark, eds. , NATO ASI Series, Kluwer Academic Publishers, Dordrecht, NL, 1999.

M. Zuker. Prediction of RNA Secondary Structure by Energy Minimization. In Computer Analysis of Sequence Data A. M. Griffin and H. G. Griffin eds. Methods in Molecular Biology, Humana Press Inc. , 267-294, 1994.

J. A. Jaeger, D. H. Turner & M. Zuker. Predicting Optimal and Suboptimal Secondary Structure for RNA. In Molecular Evolution: Computer Analysis of Protein and Nucleic Acid Sequences, R. F. Doolittle ed. Methods in Enzymology 183, 281-306, 1990.

M. Zuker. On Finding All Suboptimal Foldings of an RNA Molecule. *Science* 244, 48-52, 1989.

D. H. Mathews, J. Sabina, M. Zuker & D. H. Turner. Expanded Sequence Dependence of Thermodynamic Parameters Improves Prediction of RNA Secondary Structure J. Mol. Biol. 288, 911-940, 1999.

E. Walter, D. H. Turner, J. Kim, M. H. Lyttle, P. Müller, D. H. Mathews & M. Zuker. Coaxial stacking of helixes enhances binding of oligoribonucleotides and improves predictions of RNA folding. *Proc. Natl. Acad. Sci. USA* 91, 9218-9222, 1994.

Mathews, D. H. et al. RNA Secondary Structure Prediction. *In Current Protocols in Nucleic Acid Chemistry* S. Beaucage, D. E. Bergstrom, G. D. Glick, and R. A. Jones eds., John Wiley & Sons, New York, 11. 2. 1-11. 2. 10, (2007) DOI: 10.1002/0471142700. nc1102s28.

D. H. Mathews, S. J. Schroeder, D. H. Turner & M. Zuker. Predicting RNA Secondary Structure. In the RNA World, R. F. Gesteland, T. R. Cech and J. F. Atkins eds., 3rd edition, Cold Spring Harbor Laboratory Press, Cold Spring Harbor, New York, Chapter 22, 2006.

D. H. Mathews & M. Zuker. Predictive Methods Using RNA Sequences. In Bioinformatics: A Practical Guide to the Analysis of Genes and Proteins, A. Baxevanis and F. Ouellette eds. ,3rd edition, John Wiley & Sons, New York, Chapter 6, 2005.

D. H. Mathews, M. D. Disney, J. L. Childs, S. J. Schroeder, M. Zuker & D. H. Turner. Incorporating chemical modification constraints into a dynamic programming algorithm for prediction of RNA secondary structure. Proc. Natl. Acad. Sci. USA 101 (19), 7287-7292, 2004.

M. Zuker & D. Sankoff. RNA Secondary Structures and their Prediction. Bull. Mathematical Biology 46, 591-621, 1984.

M. Zuker & P. Stiegler. Optimal computer folding of large RNA sequences using thermodynamics and auxiliary information. *Nucleic Acids Res.* 9, 133-148, 1981.

J. -M. Rouillard, M. Zuker & E. Gulari. OligoArray 2. 0: design of oligonucleotide probes for DNA microarrays using a thermodynamic approach. *Nucleic Acids Res.* 31 (12), 3057-3062, 2003.

J. -M. Rouillard, C. J. Herbert & M. Zuker. OligoArray: Genome-scale oligonucleotide design for microarrays. *Bioinformatics* 18 (3), 486-487, 2002.

Ding, Y. et al. RNA secondary structure prediction by centroids in a Boltzmann weighted ensemble, *RNA* 2005. 11: pp. 1157-1166.

Braasch, D.A. et al. RNA Interference in Mammalian Cells by Chemically-Modified RNA, *Biochemistry* 2003,42, pp. 7967-7975.

In-Biao Ma, Keqiong Ye & Dinshaw J. Patel Structural basis for overhang specific small interfering RNA recognition by the PAZ domain, *Nature*, 429, 318 (2004).

Whitehead, K.A. et al. Nature Reviews Drug Discovery 8, 129-138 (Feb. 2009) | doi:10.1038/nrd2742, Knocking down barriers: advances in siRNA delivery.

Simeoni, F. "Insight into the mechanism of the peptide.based gene delivery system MPG: implications for delivery of siRNA into mammalian cells." *Nucleic acids research* 31.11 (2003):2717.

Liu, Z., Winters, M., Holodniy, M. and Dai, H. (2007), siRNA Delivery into Human T Cells and Primary Cells with Carbon-Nanotube Transporters. *Angewandte Chemie*, 119: 2069-2073. doi: 10.1002/ange.200604295.

Chu, T.C. et al. Aptamer mediated siRNA delivery *Nucl. Acids Res.* 34(10): e73 doi:10.1093/nar/gk1388, 2006.

Rozema, D.B. et al. Dynamic PolyConjugates for targeted in vivo delivery of siRNA to hepatocytes *PNAS* 2007 104 (32) 12982-12987.

Derfus, A.M. et al. Targeted Quantum Dot Conjugates for siRNA Delivery *Bioconjugate Chem.*, 2007, 18 (5), pp. 1391-1396, DOI: 10.1021/bc060367e.

Kumar, P. et al. T Cell-Specific siRNA Delivery Suppresses HIV-1 Infection in Humanized Mice, *Cell*, vol. 134, Issue 4, Aug. 22, 2008, pp. 577-586.

Rinaudo, K. et al. A universal RNAi-based logic evaluator that operates in mammalian cells, *Nature Biotechnology* 25, 795-801 (2007).

Ehsani, A. et al. Rational Design of Micro-RNA-like Bifunctional siRNAs Targeting HIV and the HIV Coreceptor CCR5 *Molecular Therapy* (2010) 18 4, pp. 796-802. doi:10.1038/mt.2009.321.

Tiemann, K. et al. Dual-targeting siRNAs *RNA* (2010), 16: pp. 1275-1284.

Judge, A.D. et al. Design of Noninflammatory Synthetic siRNA Mediating Potent Gene Silencing in Vivo, *Molecular Therapy* (2006) 13, pp. 494-505.

Blight K.J. et al., Secondary Structure Determination of the Conserved 98-Base Sequence at the 3' Terminus of Hepatitis C Virus Genome RNA Journal of Virology, Oct. 1997, vol. 71, pp. 7345-7352.

Ehsani, A. et al. Rational Design of Micro-RNA-like Bifunctional siRNAs Targeting HIV and the HIV Coreceptor CCR5 Molecular Therapy (2010) 18 3, pp. 796-802. doi;10.138/mt.2009.321.

PCT International Search Report mailed on Feb. 24, 2012 for PCT Application No. PCT/US2011/041703 filed Jun. 23, 2011 in the name of California Institute of Technology et al.

PCT Written Opinion completed on Feb. 22, 2012 for PCT Application No. PCT/US2011/041703 filed Jun. 23, 2011 in the name of California Institute of Technology et al.

Li, J. et al., Enzymatic signal amplification of molecular beacons for sensitive DNA detection, Nucleic Acid Research 2008, 36: 1-17.

Weissleder, R., et al In vivo imaging of tumors with proteaseactivated near-infrared fluorescent probes., Nature Biotechnology 1999, 17: 375-378.

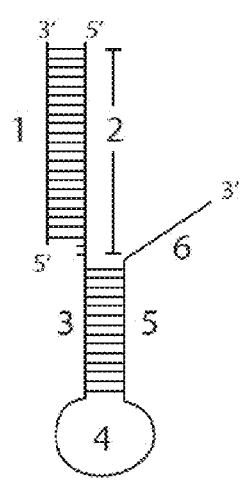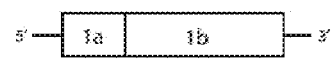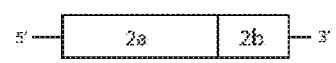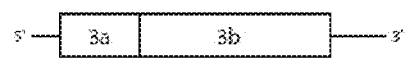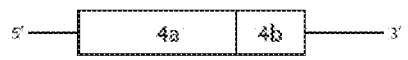
FIG. 1 siRNA targeting domain shRNA targeting domain microRNA targeting domain

Toehold placed in the terminal loop

Multistranded sensor domain

Multistranded sensor domain toehold at 5'

*In vitro* Signal Polynucleotide-dependent RNAseH Cleavage
Implementation #2: HPRT siRNA target, HIV-1 *tat/rev* Signal Polynucleotide
Hybridized with probe to segment 2

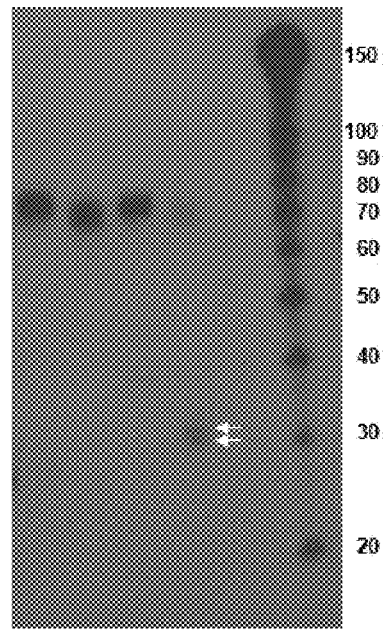

| 1 | Seg 1 + Seg 2-6 | + EDTA |
| 2 | Seg 1 + Seg 2-6 | |
| 3 | Seg * + Seg 2-6 + Signal | + EDTA |
| 4 | Seg 1 + Seg 2-6 + Signal | |

Arrows indicated Signal RNA-
dependent RNAseH cleavage product

Seg 1 = short strand
Seg 2-6 = long strand

M: RNA Decade Marker
   # nucleotides shown

FIG. 22

SEQUENCE LISTING

<160> NUMBER OF SEQ ID NOS: 18

<210> SEQ ID NO 1
<211> LENGTH: 25
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (24)..(25)
<223> OTHER INFORMATION: 2' deoxyribonucleotides

<400> SEQUENCE: 1

```
gguaacuaga gaucccucag accct                                          25

<210> SEQ ID NO 2
<211> LENGTH: 21
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (20)..(21)
<223> OTHER INFORMATION: 2' deoxyribonucleotides

<400> SEQUENCE: 2
acuagagauc ccucagaccc t                                              21

<210> SEQ ID NO 3
<211> LENGTH: 105
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (45)..(52)
<223> OTHER INFORMATION: 2' deoxyribonucleotides
<220> FEATURE:
<221> NAME/KEY: modified_base
<222> LOCATION: (77)..(78)
<223> OTHER INFORMATION: 2' deoxyribonucleotides

<400> SEQUENCE: 3
agggucugag ggaucucuag uuaccuugaa gagcucauca gumcmumtca aggtaumamc    60
mcmcmumgma mumgmamgmc mumcmumumc mgmumcmgmc mumgt                   105

<210> SEQ ID NO 4
<211> LENGTH: 27
<212> TYPE: DNA
<213> ORGANISM: artificial sequence
<220> FEATURE:
<223> OTHER INFORMATION: Synthetic polynucleotide

<400> SEQUENCE: 4
agggucugag ggaucucuag uuaccuu                                        27

<210> SEQ ID NO 5
<211> LENGTH: 21
<212> TYPE: DNA
<213> ORGANISM: artificial sequence
<220> FEATURE:
<223> OTHER INFORMATION: Synthetic polynucleotide

<400> SEQUENCE: 5
agggucugag ggaucucuag u                                              21

<210> SEQ ID NO 6
<211> LENGTH: 14
<212> TYPE: DNA
<213> ORGANISM: artificial sequence
<220> FEATURE:
<223> OTHER INFORMATION: Synthetic polynucleotide

<400> SEQUENCE: 6
gaagagcuca ucag                                                      14

<210> SEQ ID NO 7
<211> LENGTH: 22
```

```
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (4)..(11)
<223> OTHER INFORMATION: 2' deoxyribonucleotides

<400> SEQUENCE: 7
umcmumtcaa ggtaumamcm cm                                              22

<210> SEQ ID NO 8
<211> LENGTH: 28
<212> TYPE: DNA
<213> ORGANISM: artificial sequence
<220> FEATURE:
<223> OTHER INFORMATION: Synthetic polynucleotide

<400> SEQUENCE: 8
cmumgmamum gmamgmcmum cmumumcm                                        28

<210> SEQ ID NO 9
<211> LENGTH: 45
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 2' deoxyribonucleotide
<220> FEATURE:
<221> NAME/KEY: modified_base
<222> LOCATION: (34)..(34)
<223> OTHER INFORMATION: 2' deoxyribonucleotide

<400> SEQUENCE: 9
aamamamama mamcagcgac gaagagcuca ucagamamam amama                     45

<210> SEQ ID NO 10
<211> LENGTH: 42
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (21)..(22)
<223> OTHER INFORMATION: 2' deoxyribonucleotides

<400> SEQUENCE: 10
cmumgmamum gmamgmcmum cmumumcmgm umcmgmcmum gt                        42

<210> SEQ ID NO 11
<211> LENGTH: 25
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (24)..(25)
<223> OTHER INFORMATION: 2' deoxyribnucleotides

<400> SEQUENCE: 11
gccagacuuu guuggauuug aaatt                                           25

<210> SEQ ID NO 12
<211> LENGTH: 92
```

```
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (42)..(50)
<223> OTHER INFORMATION: 2' deoxyribonucleotides
<220> FEATURE:
<221> NAME/KEY: modified_base
<222> LOCATION: (71)..(72)
<223> OTHER INFORMATION: 2' deoxyribonucleotides

<400> SEQUENCE: 12
aauuucaaau ccaacaaagu cuggcuugaa gagcucauca ggctcttcaa cmumgmamum      60
gmamgmcmum cmumumcmgm umcmgmcmum gt                                    92

<210> SEQ ID NO 13
<211> LENGTH: 27
<212> TYPE: DNA
<213> ORGANISM: artificial sequence
<220> FEATURE:
<223> OTHER INFORMATION: Synthetic polynucleotide

<400> SEQUENCE: 13
aauuucaaau ccaacaaagu cuggcuu                                          27

<210> SEQ ID NO 14
<211> LENGTH: 25
<212> TYPE: DNA
<213> ORGANISM: artificial sequence
<220> FEATURE:
<223> OTHER INFORMATION: Synthetic polynucleotide

<400> SEQUENCE: 14
aauuucaaau ccaacaaagu cuggc                                            25

<210> SEQ ID NO 15
<211> LENGTH: 14
<212> TYPE: DNA
<213> ORGANISM: artificial sequence
<220> FEATURE:
<223> OTHER INFORMATION: Synthetic polynucleotide

<400> SEQUENCE: 15
gaagagcuca ucag                                                        14

<210> SEQ ID NO 16
<211> LENGTH: 28
<212> TYPE: DNA
<213> ORGANISM: artificial sequence
<220> FEATURE:
<223> OTHER INFORMATION: Synthetic polynucleotide

<400> SEQUENCE: 16
cmumgmamum gmamgmcmum cmumumcm                                         28

<210> SEQ ID NO 17
<211> LENGTH: 44
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 2' deoxyribonucleotide
<220> FEATURE:
<221> NAME/KEY: modified_base
```

-continued

```
<222> LOCATION: (34)..(34)
<223> OTHER INFORMATION: 2' deoxyribonucleotide

<400> SEQUENCE: 17
aamamamama macagcgacg aagagcucau cagamamama mama                    44

<210> SEQ ID NO 18
<211> LENGTH: 42
<212> TYPE: DNA
<213> ORGANISM: artificial sequence
<220> FEATURE:
<223> OTHER INFORMATION: Synthetic polynucleotide
<220> FEATURE:
<221> NAME/KEY: modified_base
<222> LOCATION: (21)..(22)
<223> OTHER INFORMATION: 2' deoxyribonucleotide

<400> SEQUENCE: 18
cmumgmamum gmamgmcmum cmumumcmgm umcmgmcmum gt                      42
```

SIGNAL ACTIVATED MOLECULAR DELIVERY

CROSS REFERENCE TO RELATED APPLICATIONS

This application is related to U.S. Provisional Application entitled "Ribonuclease H assisted signal activated RNA interference" Ser. No. 61/357,917, filed on Jun. 23, 2010, the disclosure of which is incorporated herein by reference in its entirety.

FIELD

The present disclosure relates to signal activated molecular delivery and in particular to signal activatable constructs, and related components, compositions, methods and systems.

BACKGROUND

Molecular delivery has been a challenge in the field of biological molecule analysis, in particular when aimed at obtaining controlled delivery of analytes of interest to specific environments. Whether for medical applications or for fundamental biology studies, several methods are commonly used for the delivery of various classes of biomaterials and biomolecules.

Controlled delivery of targets to specific environments, e.g. specific cell types and/or tissues of individuals in vitro and/or in vivo is currently still challenging, especially when directed at providing controlled release of the target in a controllable conformation, typically associated to a biological activity.

SUMMARY

Provided herein, are signal activatable constructs for enzyme-assisted molecular delivery, and related components, compositions, methods and systems. In particular, in several embodiments, signal activatable constructs herein described comprise activatable molecular complexes and activated complexes suitable for controlled release of a targeting domain, which can comprise molecules of various chemical natures.

According to a first aspect, a sensor domain is described for enzyme-assisted molecular delivery, and related compositions, methods and systems. The sensor domain comprises a protection segment, an activation segment, a displacement segment, and a toehold segment. In the sensor domain, the protection segment comprises an RNA portion and a targeting domain binding portion presented for covalent attachment to a targeting domain. In the sensor domain, the activation segment comprises a DNA portion complementary to the RNA portion of the protection segment, the displacement segment is complementary to the protection segment, and the displacement segment complementarily binds the protection segment. In the sensor domain, the toehold segment is complementary to a signal polynucleotide, and the protection segment, displacement segment, and activation segment are configured so that upon complementary binding of the signal polynucleotide to the toehold segment, the displacement segment is displaced from the protection segment and the DNA portion of the activation segment complementarily binds the RNA portion of the protection segment to provide an RNAase H binding site presented for binding. In the sensor domain, the targeting domain binding portion and the RNA portion of the protection segment are further configured to allow release of the targeting domain upon cleavage of the RNAase H binding site. The composition comprises one or more sensor domains together with a suitable vehicle. The method comprises: contacting the sensor domain with a targeting domain configured for covalently attach the one end of the protection segment, the contacting performed for a time and under condition to allow covalent attachment of the targeting domain to the protection segment in a molecular complex configured to release the targeting domain. The system comprises: a sensor domain and a targeting domain configured for covalent attachment to the target binding portion of the sensor domain to provide a complex wherein the targeting domain is bound to the protection segment through covalent attachment to the target binding portion of the protection segment, and the complex configured to release the targeting domain upon cleavage of the RNAase H binding site.

According to a second aspect a molecular complex is described for enzyme-assisted molecular delivery, and related compositions methods and systems. The molecular complex comprises a targeting domain and a sensor domain. In the molecular complex, the sensor domain comprises a protection segment comprising an RNA portion, an activation segment comprising a DNA portion complementary to the RNA portion of the protection segment; a displacement segment complementary to the protection segment, the displacement segment complementarily binding the protection segment; and a toehold segment complementary to a signal polynucleotide. In the molecular complex, the sensor domain is bound to the targeting domain through covalent attachment of the targeting domain to the protection segment of the sensor domain at a targeting domain binding portion configured to allow release of the targeting domain upon cleavage of the RNAase H binding site. In the molecular complex, the protection segment, displacement segment, and activation segment are configured so that upon binding of the signal polynucleotide, the displacement segment is displaced from the protection segment and the DNA portion of the activation segment complementarily binds the RNA portion of the protection segment to provide an RNAase H binding site presented for binding. The composition comprises one or more molecular complexes herein described together with a suitable vehicle. The method comprises: contacting the molecular complex with the signal polynucleotide and an RNAase H for a time and under condition to allow release of the targeting domain from the molecular complex. The system comprises: at least two of a molecular complex, a signal polynucleotide complementary to the toehold segment of the molecular complex and an RNAase H, for simultaneous combined or sequential use to control release of the targeting domain from the molecular complex according to the methods herein described.

According to a third aspect, an activatable molecular complex is described and related, activated complexes, compositions methods and systems. The activatable molecular complex comprises: a targeting domain and a sensor domain. In the activatable molecular complex, the sensor domain comprises: a protection segment comprising an RNA portion; an activation segment comprising a DNA portion complementary to the RNA portion of the protection segment; a displacement segment complementary to the protection segment; and a toehold segment complementary to a signal polynucleotide. The activatable molecular complex is configured to exhibit a first conformation and a second, activated, conformation wherein, in the first conformation the protection segment covalently attach the targeting domain, the displacement segment complementarily binds the RNA portion of the protection segment, and the toehold segment and at least a portion of the activation segment are presented for binding to complementary molecules; and in the second activated conformation the displacement segment and the toehold segment complementary bind the signal polynucleotide, the RNA portion of the protection segment complementary binds the DNA portion of the activation segment to provide an RNAase H binding site presented for binding, and the targeting domain is attached to the protection segment in a configuration cleavable upon cleavage of the RNAase binding site. The composition comprises one or more activatable complexes and a suitable vehicle. The method comprises contacting an activatable molecular complex, with a signal polynucleotide complementary to the toehold segment of the activatable molecular complex and an RNAase H for a time and under condition to allow release of the targeting domain from the molecular complex. The system comprises at least two of one or more activatable molecular complexes, a signal polynucleotide complementary to the toehold segment of the molecular complexes and an RNAase H, for simultaneous combined or sequential use to control release of the targeting domain from the molecular complex.

According to fourth aspect, an activated molecular complex is described and related compositions methods and systems. The activated molecular complex comprises a targeting domain and a sensor domain. The sensor domain comprises: a protection segment comprising an RNA portion; an activation segment comprising a DNA portion complementary to the RNA portion of the protection segment; a displacement segment complementary to the protection segment; and a toehold segment complementary to a signal polynucleotide. In the activated molecular complex the displacement segment and the toehold segment complementary bind the signal polynucleotide, the RNA portion of the protection segment complementary binds the DNA portion of the activation segment to provide an RNAase H binding site presented for binding, and the targeting domain is attached to the protection segment in a configuration cleavable upon cleavage of the RNAase H binding site. The related composition comprises one or more activated molecular complexes and a suitable vehicle. The related method to provide the activated molecular complex, comprises contacting the activatable molecular complex herein described in the first condition, with a signal polynucleotide complementary to the toehold segment to allow switching of the molecular complex from the first condition to the second activated condition of the molecular complex. The related method for controlled release of a targeting domain from an activated complex comprises: contacting the activated molecular complex with a signal polynucleotide complementary to the toehold segment and with an RNAase H for a time and under condition to allow release of the targeting domain from the activated molecular complex.

According to fifth aspect, a method for treating a disease in an individual through RNAse H assisted signal activated molecular delivery in cells, is described, and related compositions and systems. The method comprises administering to the individual an effective amount of one or more of the signal activatable constructs as described in the second aspect. The related pharmaceutical composition comprises one or more signal activatable constructs herein described with a pharmaceutical acceptable vehicle.

The constructs, systems, compositions and methods herein described allow in several embodiments to performed cell type specific molecular delivery.

The constructs, systems, compositions and methods herein described also allow in several embodiments integration of signal detection, signal transduction and targeting in a single compact molecular construct with easier delivery and/or administration as well as enhanced efficiency of signal transduction with respect to some approaches of the art.

The constructs, systems, compositions and methods herein described also allow in several embodiments intracellular information processing and controlling in which the presence of one set of biomolecules (e.g. protein or nucleic acid) is coupled with inhibition or activation of another set of biomolecules in the cells.

The methods and systems herein described can be used in connection with applications wherein cell-type specific modulation of cells is desired, including but not limited to medical application, biological analysis, research and diagnostics including but not limited to clinical, therapeutic and pharmaceutical applications, such as cell type specific drug delivery, cell type specific modeling or therapy, including but not limited to gene therapy and RNAi.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 1 shows a schematic illustration of a signal activatable construct according to an embodiment herein described. The left panel shows an inactive conformation of the signal activatable construct according to an embodiment herein described. The right panel shows a schematic representation of portions of segments (1)-(4) according to some embodiments herein described.

FIG. 22 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.

DETAILED DESCRIPTION

Figure 2A:
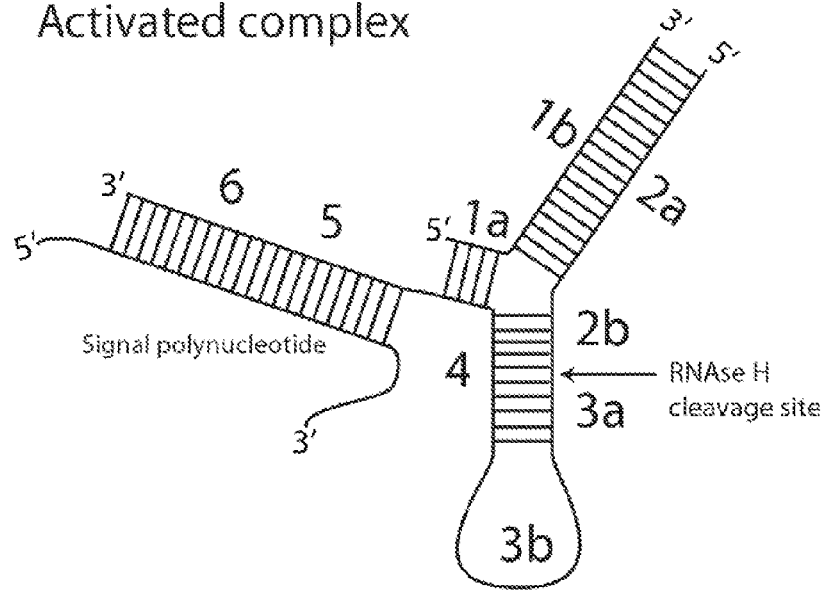
FIG. 2A shows a schematic illustration of an activated conformation of the signal activatable construct of FIG. 1 wherein the RNAase binding site is comprised of a DNA portion (4) of the activation segment complementary binding the RNA portion (3a) of the protection segment and an RNA portion (2b) of the targeting domain according to an embodiment herein described.

Herein described are signal activatable constructs for enzyme-assisted molecular delivery and related components, compositions, methods and systems.

The term "signal activatable construct" as used herein indicates a molecular complex that can have more than one conformation, and at least one of the conformations results from the binding of a signal molecule to the molecular complex. Typically, the conformation associated to the binding of a signal molecule to the molecular complex is also associated to a chemical and/or biological activity that characterizes the conformation as active with respect to the identified activity. Accordingly, signal activatable constructs herein described can have at least one active conformation and at least one inactive conformation with respect to the enzymatic activity of the enzyme assisted molecular delivery. Switching between an inactive conformation to an active conformation is triggered by binding of the signal molecule to the construct.

Signal activatable constructs and related components herein described comprise one or more polynucleotides. The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Exemplary functional groups that can be comprised in an analog include methyl groups and hydroxyl groups and additional groups identifiable by a skilled person.

Exemplary monomers of a polynucleotide comprise deoxyribonucleotide, ribonucleotides, LNA nucleotides and PNA nucleotides. The term "deoxyribonucleotide" refers to the monomer, or single unit, of DNA, or deoxyribonucleic acid. Each deoxyribonucleotide comprises three parts: a nitrogenous base, a deoxyribose sugar, and one or more phosphate groups. The nitrogenous base is typically bonded to the 1' carbon of the deoxyribose, which is distinguished from ribose by the presence of a proton on the 2' carbon rather than an —OH group. The phosphate groups is typically bound to the 5' carbon of the sugar. The term "ribonucleotide" refers to the monomer, or single unit, of RNA, or ribonucleic acid. Ribonucleotides have one, two, or three phosphate groups attached to the ribose sugar. The term "locked nucleic acids" (LNA) as used herein indicates a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. The locked ribose conformation enhances base stacking and backbone pre-organization. This significantly increases the thermal stability (melting temperature) of oligonucleotides. LNA oligonucleotides display unprecedented hybridization affinity toward complementary single-stranded RNA and complementary single- or double-stranded DNA. Structural studies have shown that LNA oligonucleotides induce A-type (RNA-like) duplex conformations. The term "polyamide polynucleotide", "peptide nucleic acid" or "PNA" as used herein indicates a type of artificially synthesized polymer composed of monomers linked to form a backbone composed of repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. In some embodiments, polynucleotides can comprise one or more non-nucleotidic or non nucleosidic monomers identifiable by a skilled person.

Accordingly, the term "polynucleotide" includes nucleic acids of any length, and in particular DNA, RNA, analogs thereof, such as LNA and PNA, and fragments thereof, possibly including non-nucleotidic or non-nucleosidic monomers, a each of which can be isolated from natural sources, recombinantly produced, or artificially synthesized. Polynucleotides can typically be provided in single-stranded form or double-stranded form (herein also duplex form, or duplex).

A "single-stranded polynucleotide" refers to an individual string of monomers linked together through an alternating sugar phosphate backbone. In particular, the sugar of one nucleotide is bond to the phosphate of the next adjacent nucleotide by a phosphodiester bond. Depending on the sequence of the nucleotides, a single-stranded polynucleotide can have various secondary structures, such as the stem-loop or hairpin structure, through intramolecular self-base-paring. A hairpin loop or stem loop structure occurs when two regions of the same strand, usually complementary in nucleotide sequence when read in opposite directions, base-pairs to form a double helix that ends in an unpaired loop. The resulting lollipop-shaped structure is a key building block of many RNA secondary structures. The term "small hairpin RNA" or "short hairpin RNA" or "shRNA" as used herein indicate a sequence of RNA that makes a tight hairpin turn and can be used to silence gene expression via RNAi.

A "double-stranded polynucleotide" refers to two single-stranded polynucleotides bound to each other through complementarily binding. The duplex typically has a helical structure, such as double-stranded DNA (dsDNA) molecule, is maintained largely by non-covalent bonding of base pairs between the strands, and by base stacking interactions.

The constructs and compolenents herein described are suitable in many embodiments for enzyme assisted molecular delivery. The term "molecular delivery" as used herein indicates any process by which controlled activation of molecular complexes regulates the release of a chemical compound for various purposes.

The term "enzyme-assisted" as used herein is defined to mean any chemical process where a protein or other chemical entity is used to catalyze or increase the rate of a chemical reaction. The protein used for this purpose can include, but is not limited to, chains of amino acids (natural or unnatural), that may or may not contain other chemical variations and can have a defined secondary structure. The chemical reaction can include, but is not limited to, reactions of RNA or portions of RNA, DNA or portions of DNA, and/or any nucleotide or derivative thereof. Typically, enzymes catalyze reactions through binding to specific or aspecific target molecular portions usually indicated as binding sites.

In several embodiments, the enzyme-assisted molecular delivery herein described is an RNAase H assisted molecular delivery. The term "RNAse H" as used herein refers to a non-specific endonuclease that is able to catalyze RNA cleavage via a hydrolytic mechanism. In particular RNase H's ribonuclease activity cleaves a 3'-O—P bond of RNA in a DNA:RNA duplex to produce 3' hydroxyl and 5' phosphate terminated products. RNAase H cleaves the RNA strand in DNA:RNA duplexes. The minimal substrate for RNAse H cleavage activity is usually a 5 to 7 base pair long stretch of duplex DNA:RNA. As used herein the term "RNAase H" comprises any enzymes whether naturally occurring or synthetically modified including any enzyme modified in one or more residues which substantially retain an endonucleasic activity such as the one herein described. Naturally occurring RNAase H enzyme which are members of the RNAse H family can be found in nearly all organisms, from archaea to prokaryote and eukaryote are identifiable by a skilled person. In human cells, RNAse H commonly cleaves the RNA sequence of a DNA: RNA duplex at a position that is 5 nucleotides from the 5' end of the RNA sequence forming the duplex. If the duplex is longer than 7 base pairs, RNAse H can cleave at additional positions to the 3' of the first cleavage site. The mammalian RNAse H class enzymes cleave the RNA portion of DNA:RNA duplexes. RNAse H class enzymes constitute the dominant mechanism of activity for many antisense oligonucleotide drugs. RNAse H can be typically active both in the cytoplasm and the nucleus.

In some embodiments, constructs herein described are signal activatable construct that comprise a sensor domain configured for providing different conformations upon binding of a signal polynucleotide through interrelation of various segments of the sensor domain. The term "signal polynucleotide" as used herein indicates a polynucleotide that is capable of acting as a signal molecule for the signal activated constructs and related components herein described. Accordingly, a signal polynucleotide herein described is capable of triggering a switch between an inactive conformation and an active conformation of the signal activated molecular construct upon binding to a segment of the signal activated construct.

The term "segment" as used herein indicates a portion of a signal activated construct having chemical and/or biological properties that are functional to changes in conformation of the signal activated construct or components thereof, and/or to a related ability to perform the enzyme assisted release herein described.

In some embodiments the sensor domain comprises a toehold segment, an activation segment, a protection segment and a displacement segment. Each of these domains comprises at least one polynucleotide portion configured so that i) the toehold segment is complementary to a signal polynucleotide; ii) the protection segment is complementary to the displacement segment; iii) the activation segment comprises a DNA portion complementary to an RNA portion comprised in the protection segment; and iv) the displacement segment is complementary to the signal polynucleotide.

The term "complementary" as used herein indicates a property of single stranded polynucleotides in which the sequence of the constituent monomers on one strand chemically matches the sequence on another other strand to form a double stranded polynucleotide. Chemical matching indicates that the base pairs between the monomers of the single strand can be non-covalently connected via two or three hydrogen bonds with corresponding monomers in the another strand. In particular, in this application, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA: RNA duplexes as well as intramolecular base paring duplexes formed by complementary sequences of a single polynucleotide strand (e.g. hairpin loop)

In some embodiments herein described of the sensors domain and related constructs, the protection segment complementary binds the displacement segment in an inactive conformation. In those embodiments, complementary binding of the signal polynucleotide to the toehold segment result in an activated conformation wherein the signal polynucleotide complementary binds the toehold segment and the DNA portion of the activation segment complementary binds the RNA portion of the protection segment to provide the enzyme binding site.

The term 'complementary bind", "base pair", "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

In particular in some embodiments, in the sensor domain and related constructs, complementary binding between the signal polynucleotide and the displacement segment is more thermodynamically stable than complementary base paring between the displacement segment and the protection segment, and complementary binding between the displacement segment and the protection segment is more thermodynamically stable than complementary base paring between the DNA portion of the activation segment and the RNA portion of the protection segment.

The term "thermodynamic stability" as used herein indicates a lowest energy state of a chemical system. Thermodynamic stability can be used in connection with description of two chemical entities (e.g. two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

In signal activatable constructs herein described the relative thermodynamic stability of the various segments of the sensor domain is configured to trigger a switch from an inactive conformation to an active conformation upon binding of a signal polynucleotide. Accordingly, switching from a conformation to another can be controlled based on a comparison of the free energy of the related systems. The term "free energy" as used herein is defined to mean a thermodynamic quantity that can be used to determine the spontaneity of a chemical reaction of transformation. Where the chemical transformation is the conversion of one polynucleotide conformation to another polynucleotide conformation, comparing the free energies of the polynucleotide conformations can be used to indicate which conformation will predominate. For example, free energy can be used to estimate thermodynamic stability of polynucleotide double-strand duplex and/or polynucleotide secondary structure that is more thermodynamically stable, but it is not limited to this use. Free energy can be estimated by computational methods, among other means.

In several embodiments, the inactivated conformation of the sensor domain or related signal activatable constructs, the meting temperature of double-stranded duplex formed by the protection segment and the displacement segment is at least about 25° C. so that the double-stranded duplex formed by the protection segment and the displacement segment is more thermodynamically stable than the three-way activation junction formed by the activation segment and portions of the first segment, the second segment and the protection segment. This is to ensure that in the absence of the signal polynucleotide, the construct adopt the inactive conformation, with the protection segment complementarily binds to the displacement segment, rather than associating with the activation segment. The strand melting temperature (Tm) of the double-stranded duplex formed by the protection segment and the displacement segment can be experimentally tested or measured (see e.g. Example 5).

In several embodiments of the signal activatable constructs herein described, in absence of a signal polynucleotide, the protection segment and the displacement segment form a first duplex through complementarily binding, wherein in the presence of the signal polynucleotide, the DNA portion of the activation segment and the RNA portion of the protection segment form a second duplex through complementary base pairing suitable for RNAse H cleavage.

In configurations of the protection segment, activation segment toehold segment and displacement segment in an inactive conformation suitable to transform to an activated conformation in presence of signal polynucleotide, are such that the binding of the signal polynucleotide to the toehold segment and the displacement segment has a melting temperature (Tm) of at least about 25° C. In some of those embodiments, sequence length and composition of toehold segment and displacement segment is such that binding of the signal polynucleotide to the toehold segment and displacement segment is at least as stable as the binding between the protection segment and the displacement segment to minimize partial displacement of the protection segment from the displacement segment upon binding of the signal polynucleotide.

For example. in some embodiments the toehold segment and the signal polynucleotide can have at least 3 consecutive base pairs to initiate binding to the signal polynucleotide and the strand displacement process, and the toehold typically comprise be at least 4 consecutive base pairs to allow functioning at the human body temperature of 37° C. Additionally, in some embodiments, sequences of the displacement segment and protection segment can be configured with respect to the complementarity of the displacement segment and signal polynucleotide so that up to every base-pair exchange is at least equal-energy, to minimize incomplete displacement process. For example, according to some embodiments, if at certain position of the duplex, the displacement segment and the protection segment have a GC base-pair, then the signal polynucleotide can also have a GC base pair with the displacement segment at the corresponding position; if the displacement segment and the protection segment have a 2'-O-methyl G base pairs with a C at certain position, also the signal polynucleotide can base pair to the displacement segment with a 2'-O-methyl G base pairs with a C. In some embodiments, the complementary binding between the displacement segment with the signal polynucleotide can be at least as stable, and possible more stable, than the complementarily binding between the displacement segment and the protection segment. Accordingly, mismatches between the displacement segment and the protection segment at certain position, can correspond to mismatches between the signal polynucleotide and the displacement segment. In some embodiments stabilizing modifications such as 2'-O-methyls can be localized in the displacement segment, since that displacement segment of the construct base pairs with both the signal polynucleotide and the protection segment. In determining the configuration, length and sequence the delivery conditions can also be considered (e.g. temperature and salts concentrations).

FIG. 1 shows an exemplary signal activatable construct according to an embodiment herein described, shown in an inactive form. In the illustration of FIG. 1 wherein the sensor domain comprises a protection segment (3), an activation segment (4), a displacement segment (5) and a toehold segment (6) and attaches a targeting domain formed by a duplex polynucleotide having a first segment (1) and a second segment (2) by covalent linkage.

The term "covalent binding" or "covalently linked" as used herein indicates connection between two segments through formation of a chemical bonding that is characterized by sharing of pairs of electrons between atoms, known as the covalent bond. Examples covalent binding can include, but are not limited to covalent bonds formed between any two of the following: RNA or portions RNA, DNA or portions of DNA, any nucleotide or derivative thereof, and/or enzyme.

In particular, in the illustration of FIG. 1, left panel, the toehold segment (6) comprises a polynucleotide configured to initiate binding to the signal polynucleotide (e.g. a signal polynucleotide of a cell of interest) covalently linked at the 5' terminus to the displacement segment (5) which comprise a polynucleotide that on its turn covalently links at the 3' terminus the 5' terminus activation segment (4) formed by a single stranded polynucleotide. The activation segment (4) binds at the 5' terminus, the 3' terminus of the protection segment (3), and the 5' terminus of protection segment (3) is covalently linked to the 3' terminus of the second segment (2). Covalent linkage between two segments of a construct herein described can occur directly between functional groups of the segments or indirectly e.g. through covalent binding of the two segments to opposite sides of a suitable linker. In the illustration of FIG. 1 left panel the protection segment (3) is also complementarily bound to the displacement segment (5) to form a stem loop structure.

In the illustration of FIG. 1, each segment comprises polynucleotidic portions complementary one to another to provide the construct schematically illustrated in FIG. 1 left panel. A schematic illustration of those portions is shown in FIG. 1, right panel, wherein the portions (1a) and (1b) of the first segment (1); portions (2a) and (2b) of second segment (2), portions (3a) and (3b) of protection segment (3) and portions (4a) and (4b) of activation segment (4) are schematically illustrated. In particular, in the embodiment exemplified by the illustration of FIG. 1, portions (3a) and possibly also (2b) define an RNA portion of the construct and (4a) and/or (4b) define the DNA portion complementary to the RNA portion defined by (3a) and possibly also (2b). In the embodiment exemplified by the illustration of FIG. 1, portion (1a) is complementary to portion (2b); portion (1b) is complementary to portion (2a), portions (3a) and (3b) are complementary to segment (5), portion (4a) is complementary to portion (3a), and portion (4b) is complementary to portions (3a) and (2b).

Figure 2B:
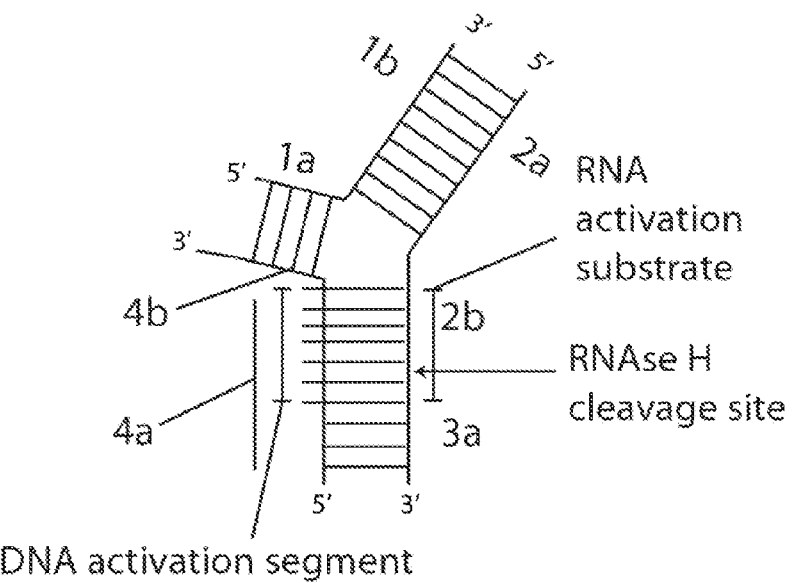
FIG. 2B shows a detailed view of a portion of the activated conformation of the signal activatable construct shown in FIG. 2A, showing DNA portion (4b) complementary binding the RNA portion (3a) of the protection segment and the RNA portion (2b) of the targeting domain.

The complementarity between the polynucleotidic portions of the various segments of the construct of FIG. 1 enables switching of the construct from an inactive conformation with respect to RNAase H assisted release of the targeting domain (1, 2) to an activated conformation in presence of a signal polynucleotide as shown in FIGS. 2A and 2B.

FIG. 2A shows an activated conformation of the signal activated construct according to the embodiment shown in FIG. 1. In the activated conformation, a signal polynucleotide binds to toehold segment (6) and displacement segment (5) through complementary base paring, which at the same time displace protection segment (3) from binding to displacement segment (5), and which also allows the displaced protection segment (3) to bind to activation segment (4). In particular, as shown in FIG. 2A, activation segment (4) binds to a portion of first segment (1), second segment (2) and third segment (3) through complementary binding, forming a three-way activation junction. In particular, in the illustration of FIG. 2A the DNA activation sequence (4a) binds to a RNA sequence (2b-3a) located at the junction of the second segment and the protection segment forming a DNA:RNA duplex suitable for RNAse H cleavage, leaving a portion of the protection segment (3b) in a loop; A additional portion (4b) of the activation segment (4) binds to the portion (1a).

FIG. 2B shows a detailed view of the RNAas H binding site of the activated conformation of the construct shown in FIG. 2A. The activation junction comprises portions (1a), (1b), (2a), (2b), (3a), (4a), and (4b), in which a DNA:RNA duplex formed by portion (4a) and portions (2b-3a), provides a suitable cleavage site for RNAse H.

In an activated conformation, such as the one illustrated in FIG. 2B when the displacement segment complementary binds to the signal polynucleotide, activation segment (4) complementarily binds to portions of first segment (1), second segment (2) and protection segment (3), forming a three-way activation junction. This kind of junction can have a melting temperature of at least about 15° C. In particular, in some embodiments, a three-way activation junction such as the one illustrated in FIG. 2B can comprise a DNA: RNA duplex of at least 5 consecutive base pairs that is composed of unmodified nucleotides. The melting temperature of the three-way activation junction of an activated construct such as the one exemplified in FIG. 2B can be experimentally tested or measured using standard methods after removing the displacement segment from the construct. In this particular, embodiment, formation of the three-way activation junction is associated to the correct placement of the DNA:RNA duplex, and hence, positioning of the cleavage site of RNAse H in the construct. Possible variations of this structure can be envisioned by a skilled person in view of the present disclosure. For example, phosphorothioate backbone modifications can be applied to the DNA activation sequence to enhance DNA stability without affecting RNAse H activity. The strand melting temperature (Tm) of the activation junction can be experimentally tested or measured (see e.g. Example 4).

Figure 2C:
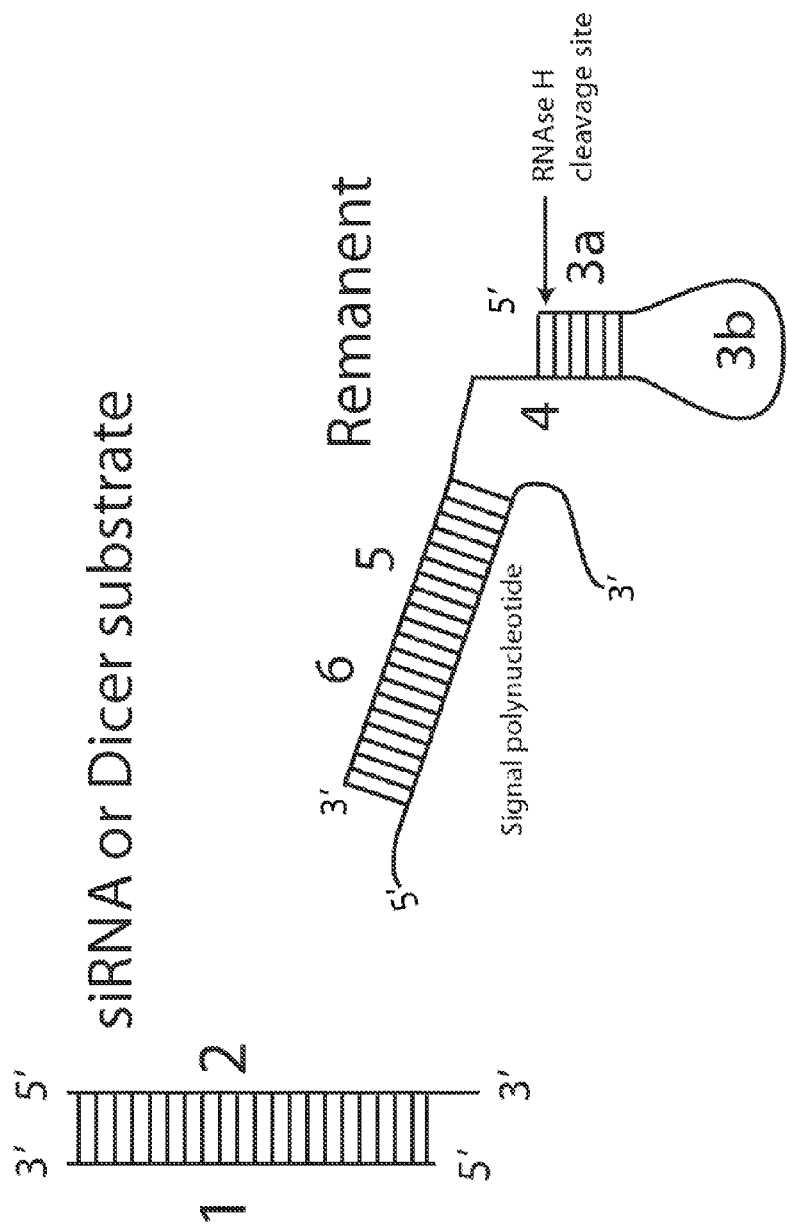
FIG. 2C shows products of the signal activated construct according to the embodiment shown in FIG. 2B following enzymatic cleavage of the activated construct.

FIG. 2C shows products of RNAse H cleavage of the activated construct shown in FIG. 2B. The targeting domain formed by a double-stranded duplex structure, which comprises first segment (1) and second segment (2), is released from a remanent comprising protection segment (3), activation segment (4), displacement segment (5), toehold segment (60 and the signal polynucleotide. In the illustration of FIG. 2C, the released targeting domain has a blunt end at the 3' of the first segment and an at least 2-base single stranded overhang at the 3' of the second segment and thus can be used as a siRNA or a suitable substrate for Dicer. A skilled person will understand that production of a targeting domain with a blunt end or a longer overhang or other configuration of the 3' terminus are possible based on the configuration and location of the RNAase H binding site on the molecular construct.

Figure 3A:
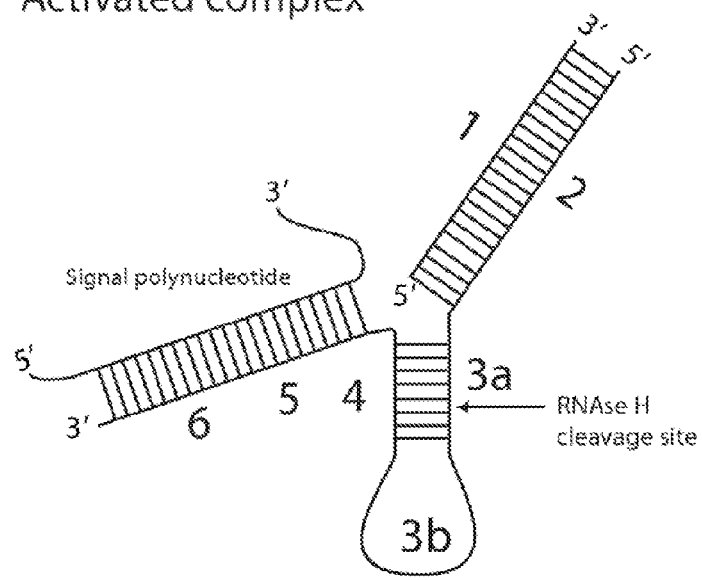
FIG. 3A shows an activated conformation of the signal activatable construct of FIG. 1 wherein the RNAase binding site is comprised of a DNA portion (4) of the activation segment complementary binding the RNA portion (3a) of the protection segment according to an embodiment herein described.

FIG. 3A shows an activated conformation of the signal activated construct according to the embodiment of FIG. 1. In the activated conformation, a signal polynucleotide binds to toehold segment (6) and displacement segment (5) through complementary base paring, which displaces protection segment (3) from binding to the displacement segment (5), and which also allows binding of the displaced protection segment (3) to activation segment (4). In particular, in the illustration of FIG. 3A, activation segment (4) binds a portion of protection segment (3) through complementarily binding, forming a two-way activation junction. In particular, DNA portion (4a) binds to the RNA portion (3a) located adjacent to the junction of the second segment and the protection segment forming a DNA:RNA duplex suitable for RNAse H cleavage, leaving a portion (3b) of the protection segment in a loop.

Figure 3B:
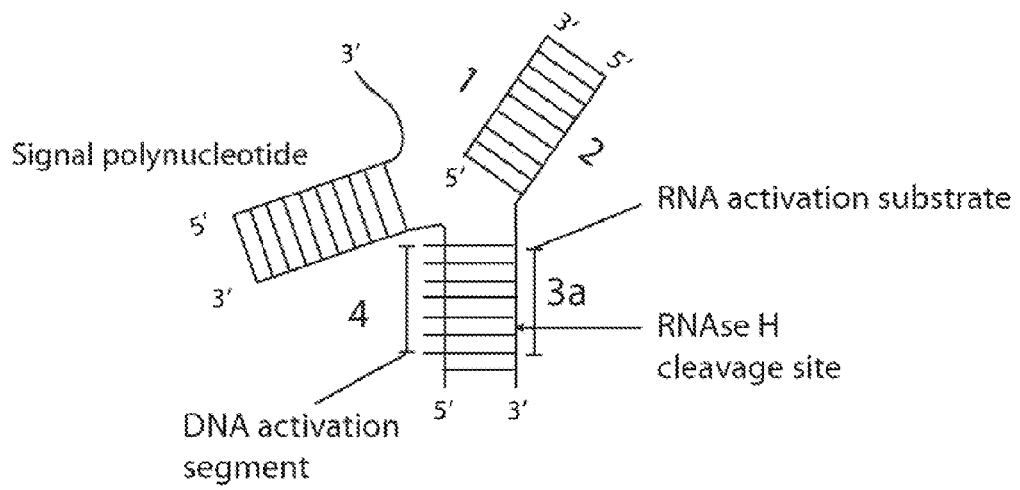
FIG. 3B shows a detailed view of a junction portion of the activated conformation of the signal activatable construct as shown in FIG. 3A.

FIG. 3B shows a detailed view of the activation junction of the activated conformation of the construct shown in FIG. 3A. The activation junction comprises portions (1a), (2b), (3a), and (4a), in which a DNA:RNA duplex formed by portion (4a) and portion (3a) provides a suitable cleavage site for RNAse H.

Figure 3C:
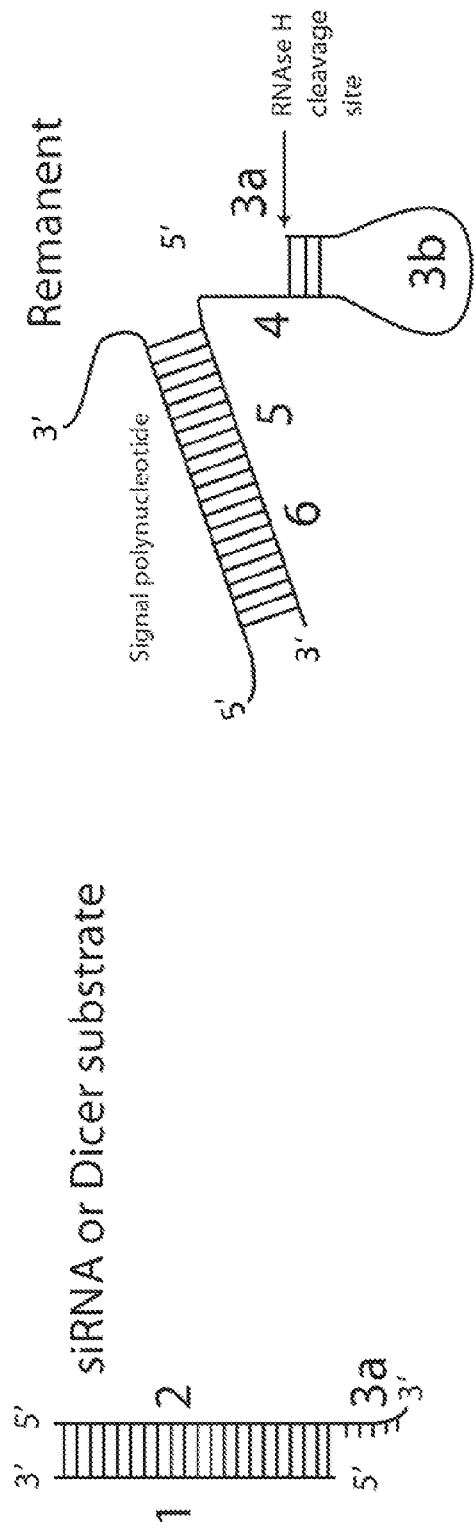
FIG. 3C shows products of RNAse H cleavage of the activated signal activatable construct according to the embodiment shown in FIG. 3B.

FIG. 3C shows products of RNAse H cleavage of the activated construct shown in FIG. 3B. The targeting domain of a double-stranded duplex structure, which comprises first segment (1), second segment (2) and portion (3a) of the protection segment (3), is released from a remanent comprising remaining portion (3b) of protection segment (3), activation segment (4), displacement segment (5), toehold segment (6) and the signal polynucleotide. In the illustration of FIG. 3C, the released double-stranded duplex has a blunt end at the 3' of first segment (1) and an at least 5-base single stranded overhang at the 3' of second segment (2) and therefore can be used as a siRNA or a suitable substrate for Dicer. Also in this case a skilled person will understand that production of a targeting domain with a blunt end or a longer overhang or other configuration of the 3' terminus are possible based on the configuration and location of the RNAase H binding site on the molecular construct.

In the exemplary embodiments of FIGS. 2 and 3 the signal activatable construct adopts thermodynamically stable inactive and active conformations depending on binding presence of a signal polynucleotide. In particular, the signal activatable construct adopts an inactive conformation in absence of a signal polynucleotide, and switch to an activated conformation upon binding of a signal polynucleotide.

Signal polynucleotides can be artificially synthesized in or typically are already present in the environment wherein activation of the construct is desired cytoplasm of cells and analogous biochemical environments, such as a cell lysate (see Example 2 and Example 3). Exemplary signal polynucleotides according to the present disclosure include but are not limited to a synthetic polynucleotide, RNA sequence present in cytoplasm or nuclei of cells, such as mRNA, non-coding RNA, microRNA, microRNA precursors, small interfering RNA, aptamers, tRNA, and by-products of abortive RNA transcription, RNA splicing or RNA degradation. The signal polynucleotide can be present in a free form or bound to RNA binding proteins such as RISC.

Figure 4:
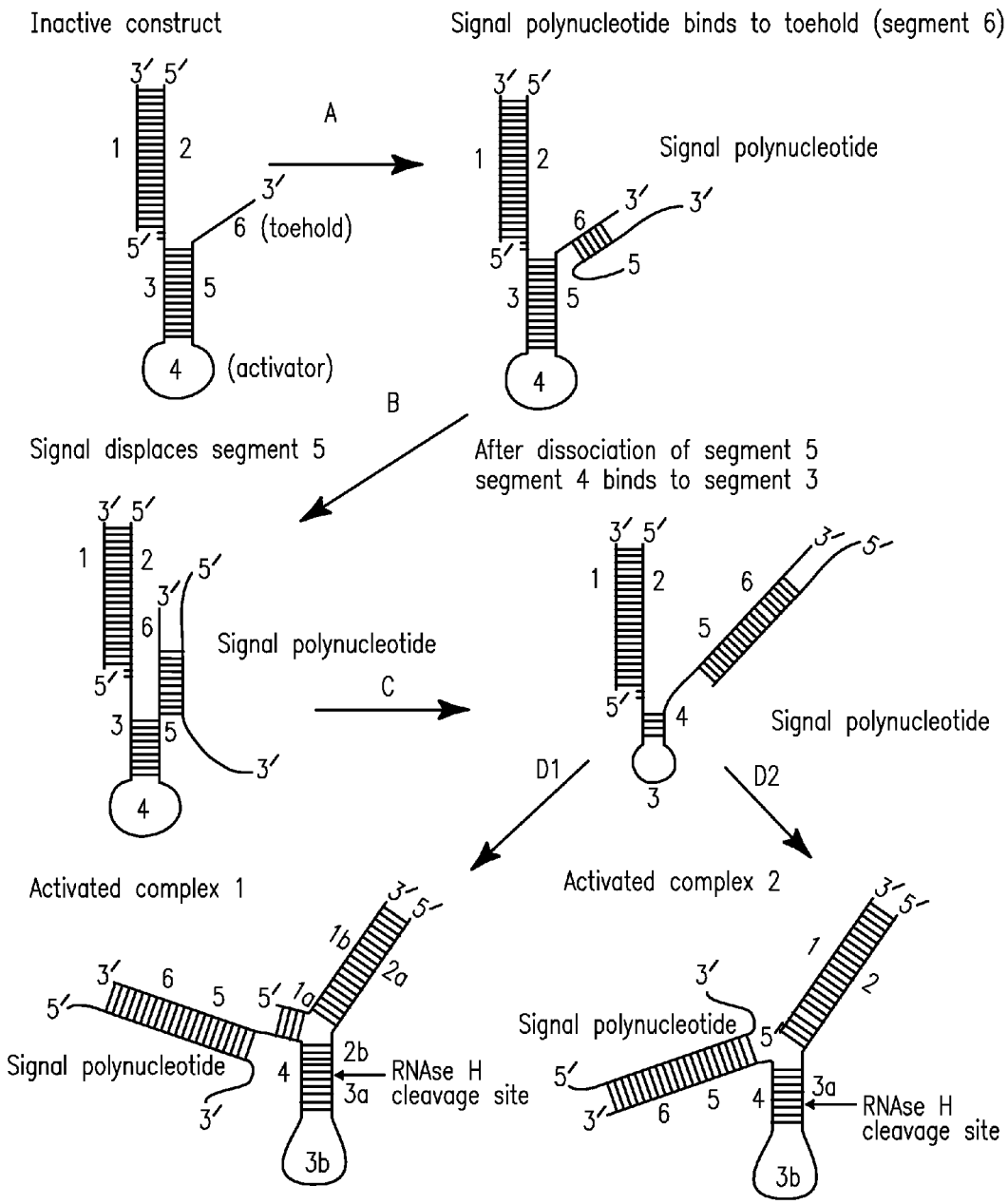
FIG. 4 shows an exemplary process of signal activation of the signal activatable construct herein described.

FIG. 4 shows exemplary processes of signal activated transformation of the construct following binding of a signal polynucleotide, which are provided for guidance purpose and are not intended to be limiting. In particular, in the illustration of FIG. 4 possible steps for obtaining conversion of the construct from the inactive conformation shown in FIG. 1 to the activated conformations as shown in FIGS. 2A and 3A are shown. In the illustration of FIG. 4, signal activation is initiated by binding of a signal polynucleotide to the toehold segment (6) of the sensor domain (3, 4, 5 and 6) (see FIG. 4, step A). The portion of the construct formed by the toehold segment (6) and the displacement segment (5) is at least partially complementary to the signal polynucleotide with a complementary base paring between them more energy favorable than that between the displacement segment and the protection segment. Therefore, binding between the signal polynucleotide to toehold segment (6) extends from toehold segment (6) into at least part of the displacement segment (5), which at the same time displaces the corresponding portion of the protection segment (3) from the complementary binding to the displacement segment (5) (see FIG. 4, step B). This process is commonly known as a strand displacement or branch migration reaction. Due to partial or complete displacement of the protection segment, the protection segment disassociate with the displacement segment, which allows the DNA activation sequence comprised in the activation segment (4) to base pair with the RNA portion located at or near the junction between the second segment (2) and the protection segment (3) (see FIG. 4, step C). The complementary base pairing between the protection segment and the displacement segment is more energy favorable than the complementary base pairing between the DNA portion of the activation segment (4) and the RNA portion of the protection segment (3). Therefore, only after the protection segment (3) is displaced by the signal polynucleotide, and disassociate from the displacement segment, the DNA activation sequence is able to base pair with the RNA activation substrate to form a DNA:RNA duplex, which serves as a suitable substrate for RNAse H (see FIG. 4, step D1 and D2 schematically illustrating the steps providing the activated construct of FIGS. 2 and 3 respectively).

The term "displacement", "strand displacement reaction" or "branch migration reaction" as used herein generally indicates the process in which two polynucleotide strands with partially or full complementarity hybridize, displacing in the process one or more pre-hybridized strand or sequence. The strand displacement process can be experimentally tested or measured according to techniques herein described (see e.g. Example 6) and identifiable by a skilled person.

In the illustration of FIGS. 1 to 4, the constructs depicted comprise a targeting domain formed by a double stranded polynucleotide, comprising a segment (1) and a segment (2) complementary bound one to the other. In several embodiments, the double stranded polynucleotide can be formed by RNA suitable for interfering in RNAi or other molecular system as will be understood by a skilled person upon reading of the present disclosure. In some of those embodiments, the RNA targeting domain can include various structural modifications that are functional to one or more desired properties of the RNA targeting domain to be released.

Figure 5A:
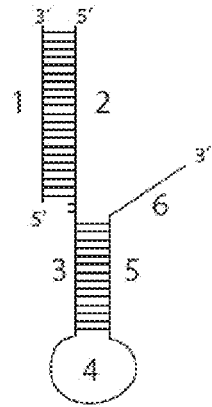
FIG. 5A shows a schematic illustration of the signal activatable construct according to an embodiment herein described, wherein the 3' terminus of a polynucleotide segment (1) complementary binds to the 5' terminus of polynucleotide segment (2), forming a blunt end of the targeting domain of the construct.
Figure 5B:
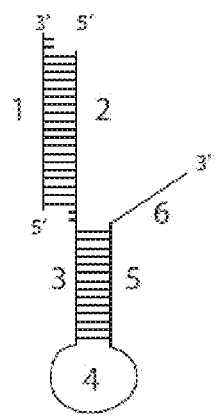
FIG. 5B shows a schematic illustration of the signal activatable construct according to an exemplary embodiment herein described, wherein the 3' terminus of a polynucleotide segment (1) has a single-stranded overhang of 2 nucleotides.

FIGS. 5A to 5D shows exemplary variations to the targeting domain in exemplary constructs illustrated in its inactive conformation. In the illustration of FIG. 5A the 3' terminus of segment (1) is base-paired with the 5' terminus of segment (2), forming a blunt end of the targeting domain of the construct. In the illustration of FIG. 5A, first segment (1) and second segment (2) are at least 17 nucleotides in length, and in particular can be 22 nucleotides in length. In the illustration of FIG. 5B, the 3' terminus of segment (1) has a single stranded overhang of at least one base, and in particular 2 nucleotides.

Figure 5C:
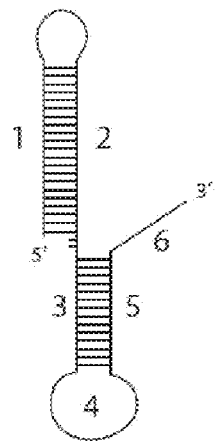
FIG. 5C shows a schematic illustration of the signal activatable construct according to an exemplary embodiment herein described, wherein the 3' terminus of a polynucleotide segment (1) is attached to the 5' terminus of polynucleotide segment (2) via a polynucleotide linker.
Figure 5D:
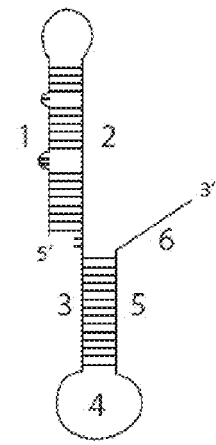
FIG. 5D shows a schematic illustration of the signal activatable construct according to an exemplary embodiment herein described, wherein the 3' terminus of polynucleotide segment (1) is attached to the 5' terminus of polynucleotide segment (2) via a polynucleotide linker, and wherein the complementary binding between polynucleotide segment (1) and polynucleotide (2) have mismatches and bulges schematically illustrated in a way that mimics endogenous mammalian microRNA.

In the illustration of FIG. 5C, the 3' terminus of segment (1) is connected with the 5' terminus of segment 2 via a polynucleotide linker. In the illustration of FIG. 5D, the 3' terminus of segment (1) is connected with the 5' terminus of segment (2) via a polynucleotide linker, and base pairing between segments (1) and (2) have mismatches and bulges in a way that mimics endogenous mammalian microRNA. Additional variations of the double stranded RNA structure and composition of the targeting domain (1, 2) of FIGS. 5A-5D and derivatives are identifiable by a skilled person upon reading of the present disclosure.

Although only polynucleotide targeting domains are shown in the illustration of FIGS. 5A-5D and in other figures of the present disclosure, in various embodiments of signal activatable construct herein described a targeting domain can comprise a molecule other than RNA or a polynucleotide configured to be delivered to a target with the cells in the presence of the signal polynucleotide. Exemplary types of cargo molecule that can be comprised in all or in part as a targeting domain according to the current disclosure include but are not limited to peptides, small, molecules aptamers, antibodies, and other chemical compound identifiable by a person skilled in the art.

In those embodiments, the targeting domain formed by the cargo molecule or attaching the cargo molecule, can be carried and delivered by constructs herein described wherein the segments of the sensor domain are arranged in various configurations which allow switching of the construct from an inactive conformation to an active conformation with respect to the enzyme assisted release of the targeting domain as will be understood by a skilled person upon reading of the present disclosure. For example in embodiments, wherein the targeting segment is configured for delivery of a cargo molecule, the cargo molecule can be covalently linked to the 5' terminus of the protection segment. In those embodiments wherein the cargo molecule comprises a cargo such as a polynucleotide aptamer, the cargo molecule can be non-covalently attached to the construct for example through complementarily binding to the second segment of the targeting domain or other base pairing segment linked to the 5' of the protection segment to be used to base pair to some portion of the cargo. In particular, in some of the embodiments wherein a duplex formed between the cargo molecule and the second segment of the targeting domain or other base pairing segment, the duplex can have a melting temperature of at least 15° C.

Figure 6A:
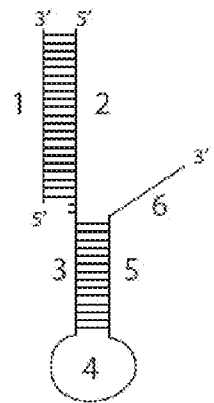
FIG. 6A shows a schematic illustration of the signal activatable construct according to an exemplary embodiment herein described, wherein polynucleotide toehold segment (6) is arranged as a single-stranded polynucleotide overhang at the 3' terminus of displacement segment (5).
Figure 6B:
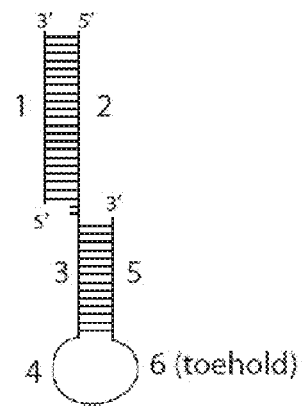
FIG. 6B shows a schematic illustration of the signal activatable construct according to an exemplary embodiment herein described, wherein toehold segment (6) is arranged at the 5' terminus of displacement segment (5) and at the 3' terminus of activation segment (4), and wherein the toehold segment (6) is in a loop of a stem-loop structure formed by protection segment (3), displacement segment (5), activation segment (4) and toehold segment (6).
Figure 6C:
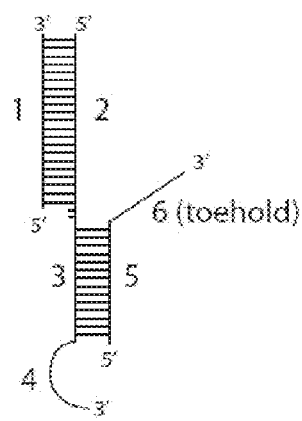
FIG. 6C shows a schematic illustration of the signal activatable construct according to an exemplary embodiment herein described wherein the sensor domain of the construct comprises multiple polynucleotide strands. In particular, in the schematic illustration of FIG. 6C activation segment (4) is arranged at the 3' terminus of protection segment (3), toehold segment (6) is arranged at the 3' end of displacement segment (5), wherein the 5' terminus of activation segment (4) is covalently attached to the 3' terminus of protection segment (3) and wherein the 3' terminus of activation segment (4) is not attached to any other segments of the construct and is presented for binding.
Figure 6D:
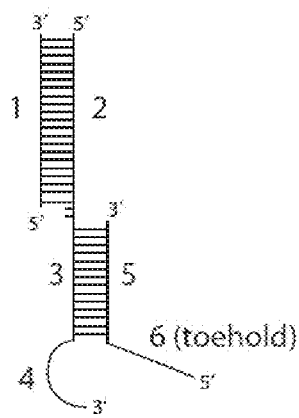
FIG. 6D shows a schematic illustration of the signal activatable construct according to an exemplary embodiment herein described, wherein the sensor domain of the construct comprises multiple polynucleotide strands. In particular, in the schematic illustration of FIG. 6D, activation segment (4) is arranged at the 3' terminus of protection segment (3), and toehold segment (6) is arranged at the 5' end of displacement segment (5). In the illustration of FIG. 6D, the 5' terminus of activation segment (4) is covalently attached to the 3' terminus of protection segment (3) and wherein the 3' terminus of activation segment (4) is not attached to any other segments of the construct and is presented for binding. In the illustration of FIG. 6D, the 3' terminus of toehold segment (6) is covalently attached to the 5' terminus of displacement segment (5) and wherein the 5' terminus of toehold segment (6) is not attached to any other segments of the construct and is presented for binding

For example FIGS. 6A to 6D and FIGS. 7A to 7B show exemplary variations of a sensor domain of the construct herein described depicted in its inactive conformation. In the illustration of FIG. 6A, toehold segment (6) comprising a toehold sequence for complementary binding with a signal polynucleotide, is arranged as a single-stranded overhang at the 3' terminus of the displacement segment (5), while activation segment (4) comprising a DNA activation sequence is arranged as a loop of a stem-loop structure formed by the protection segment (3), activation segment (4), and displacement segment (5). In the illustration of FIG. 6B, toehold segment (6) is in the loop of a stem-loop structure formed by protection segment (3), activation segment (4), toehold segment (6) and displacement segment (5). In the illustration of FIG. 6C, activation segment (4) comprising the DNA activation sequence is not covalently linked to, and is therefore disconnected from, displacement segment (5). Accordingly, in the illustration of FIG. 6C activation segment (4) and is therefore arranged as a single-stranded overhang at the 3' terminus of protection segment (3). In the illustration of FIG. 6D, toehold segment (6) comprising a toehold sequence capable of complementary binding a signal polynucleotide is arranged as a single-stranded overhang at the 3' terminus of displacement segment (5).

Figure 7A:
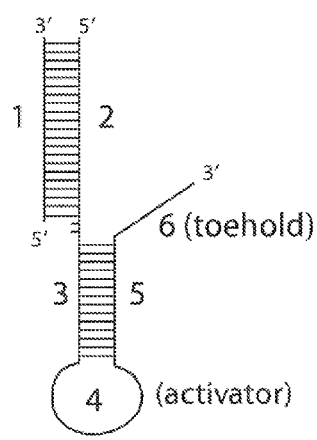
FIG. 7A shows a schematic illustration of the signal activatable construct according to an embodiment herein described, showing arrangement of activation segment (4) between the 3' terminus of protection segment (3) and the 5' terminus of displacement segment (5), and is located in the loop of a stem-loop structure formed by segments (3-5). In the illustration of FIG. 7A, toehold segment (6) is arranged as a single-stranded overhang at the 3' terminus of displacement segment (5).
Figure 7B:
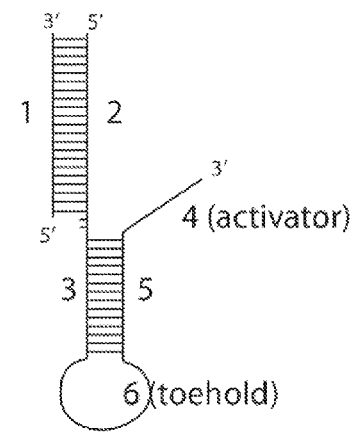
FIG. 7B shows a schematic illustration of the signal activatable construct according to an exemplary embodiment herein described, showing arrangement of toehold segment (6) between the 3' terminus of protection segment (3) and the 5' terminus of displacement segment (5), and is located in the loop of a stem-loop structure formed by segments (3-5). In the illustration of FIG. 7A, activation segment (4) is arranged as a single-stranded overhang at the 3' terminus of displacement segment (5).

In the illustration of FIG. 7A, toehold segment (6) is arranged as a single-stranded overhang at the 3' terminus of displacement segment, while activation segment (4) is arranged as a loop of a stem-loop structure formed by protection segment (3), activation segment (4), and displacement segment (5). In the illustration of FIG. 7B, activation segment (4) is arranged as a single-stranded overhang at the 3' terminus of displacement segment (5), while toehold segment (6) is arranged as a loop of a stem-loop structure formed by protection segment (3), activation segment (4), and displacement segment (5). In a construct such as the one exemplified in FIGS. 7A and 7B, portion (4d) is typically at least 2 consecutive non-wobble base pairs with portion 1a. In particular, (4d) can be at least 3 or 4 non-wobble pair bases with (1a) configured to enhance stability. In particular, (4d) can comprises 2'-O-methyl ribonucleotides, because 2'-O-methylation introduce thermodynamic stability to ribonucleotide base pairs, but not to bases pairs formed between ribonucleotides and deoxyribonucleotides.

Figures 7C, 7D:
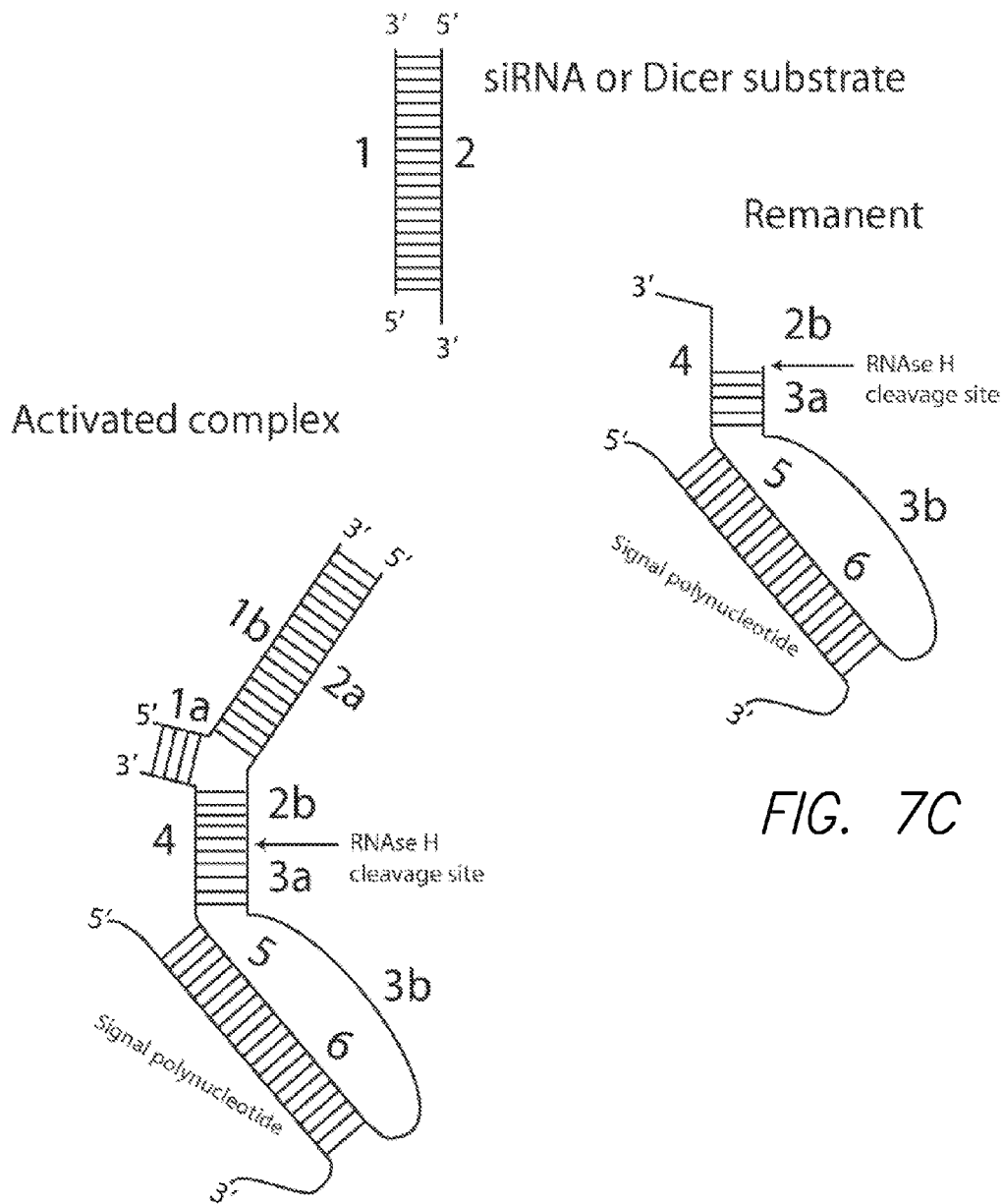
FIG. 7C shows a schematic illustration of an activated conformation of the signal activatable construct according to the embodiment shown in FIG. 7B.
FIG. 7D shows the products of RNAse H cleavage of the activated signal activatable construct according to the embodiment shown in FIG. 7B.

An exemplary schematic illustration of the conversion of the constructs of FIG. 7B upon binding of the signal polynucleotide is shown in FIG. 7C and FIG. 7D depicting the activated complex (see FIG. 7C) and products released following RNAase H processing of the activated construct (see FIG. 7D) respectively.

Additional exemplary configurations of signal activated constructs herein described and related exemplary arrangements of the segments is illustrated in FIGS. 8-16.

Figure 8:
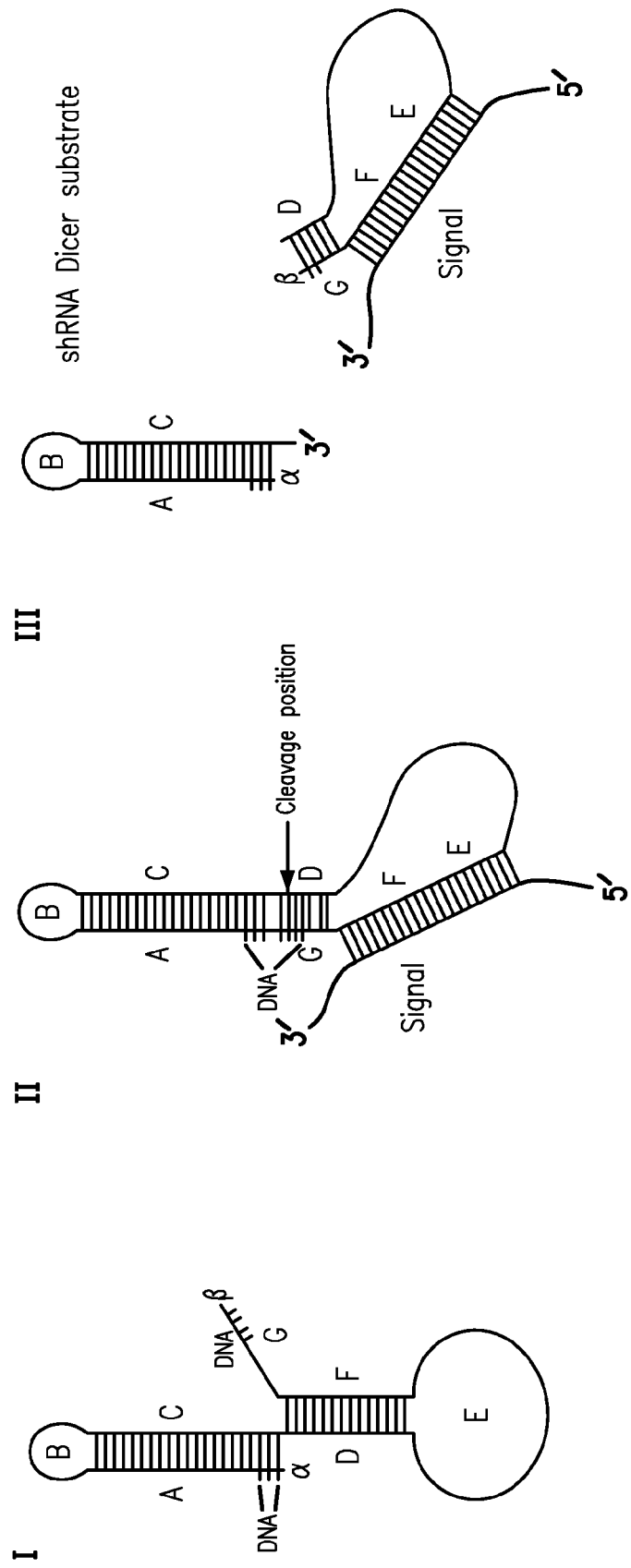
FIG. 8 shows a schematic illustration of an exemplary embodiment of the signal activatable construct according to the current disclosure, where a segment (A) of the targeting domain comprises a short DNA sequence as indicated, and wherein in the inactive conformation, the toehold segment (E) is arranged in a loop between the protection segment (D) and the displacement segment (F) and wherein the activation segment (G) is arranged as a single strand overhang at the 3' terminus of the displacement segment (E).

In the exemplary schematic illustration of FIG. 8, the targeting domain comprises first segment (A) and second segment (C); the sensor domain comprises protection segment (D), activation segment (G), displacement segment (F) and toehold segment (E). In particular, FIG. 8(I) shows the construct in an inactive conformation, wherein first segment (A) and second segment (C) are covalently linked and therefore connected via a polynucleotide linker (B) which forms a stem-loop structure with first segment (A) and second segment (C) base paring one with the other in the stem. The protection segment (D), toehold segment (E) and displacement segment (F) also form a stem-loop structure with protection segment (D) and displacement segment (F) which base pair one with the other in the stem, supporting a loop comprising toehold segment (E). In the illustration of FIG. 8(I), activation segment (G) is arranged as a single strand overhang at the 3' terminus of the displacement segment and the DNA binding portion (herein also DNA activation sequence) of activation segment (G) located proximate to the 3' single-stranded overhang is schematically illustrated in the figure. In the illustration of FIG. 8(I), toehold segment (E), which comprises a toehold sequence, is arranged as a loop of a stem-loop structure formed by protection segment (D), and displacement segment (F). Additionally, in this embodiment, the first segment comprises at one or more consecutive deoxyribonucleotides at the 5' terminus complementing one or more consecutive ribonucleotide located at the 3' terminus of second segment. FIG. 8(II) shows the construct of FIG. 8(I) in an activated conformation, wherein upon binding of a signal polynucleotide to toehold segment (E) and displacement segment (F), the DNA activation sequence comprised in activation segment (G) base pairs to the RNA portion located in protection segment (D), forming a DNA:RNA duplex, which is adjacent to the DNA:RNA duplex formed by first segment (A) and second segment (C), thus forming as a gapmer substrate for RNAse H. FIG. 8(III) shows products of RNAse H cleavage of the activated signal activated construct of FIG. 8(II). The targeting domain of a stem-loop structure, which comprises first segment (A), second segment (C) and polynucleotide linker (B) between segments (A) and (C) is released from a remanent comprising activation segment (G), protection segment (D), displacement segment (F), toehold segment (E) and the signal polynucleotide. The RNAse H cleavage creates an exposed 3' end with a proper —OH terminus of the second segment. Thus the released targeting domain becomes a small hairpin RNA (shRNA) substrate for Dicer or other RNAi loading pathway enzymes. In the exemplary illustration of FIG. 8(III), the 5' terminus of the first segment of the shRNA substrate comprises at least 1 DNA base.

Figure 9:
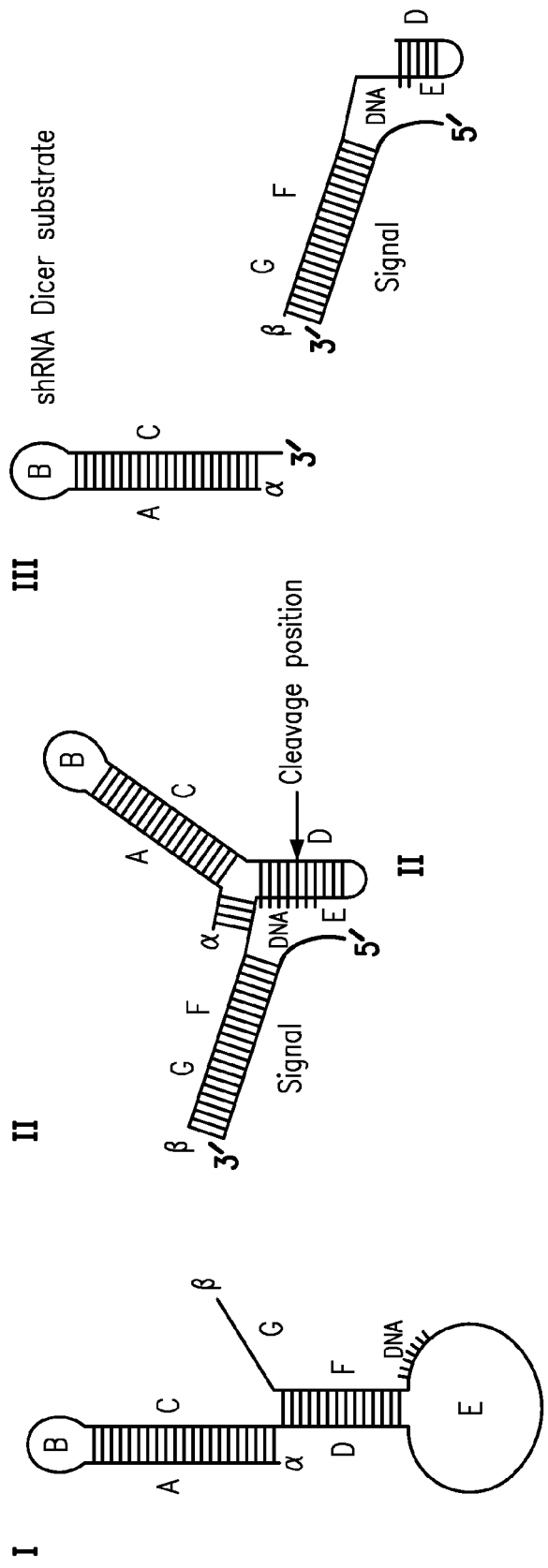
FIG. 9 shows a schematic illustration of an exemplary embodiment of the signal activatable construct showing a first segment (A) covalently attached to a second segment (B) of the targeting domain with a polynucleotide linker.

In the exemplary illustration of FIG. 9, the targeting domain comprises first segment (A) and second segment (C); and the sensor domain comprises protection segment (D), activation segment (E), displacement segment (F) and toehold segment (G). In particular, FIG. 9(I) shows the construct in an inactive conformation, wherein first segment (A) and second segment (C) are connected via a polynucleotide linker (B), and form a stem-loop structure and the DNA binding portion of activation segment (E) is adjacent to displacement segment (F) as schematically illustrated in the figure. FIG. 9(II) shows the construct of FIG. 9(I) in an activated conformation, following binding of a signal polynucleotide to a complementary portion of toehold segment (G). FIG. 9(III) shows products of RNAse H cleavage of the activated construct of FIG. 9(II), wherein the released targeting domain is a small hairpin RNA (shRNA) substrate for Dicer or other RNAi loading pathway enzymes.

Figure 10:
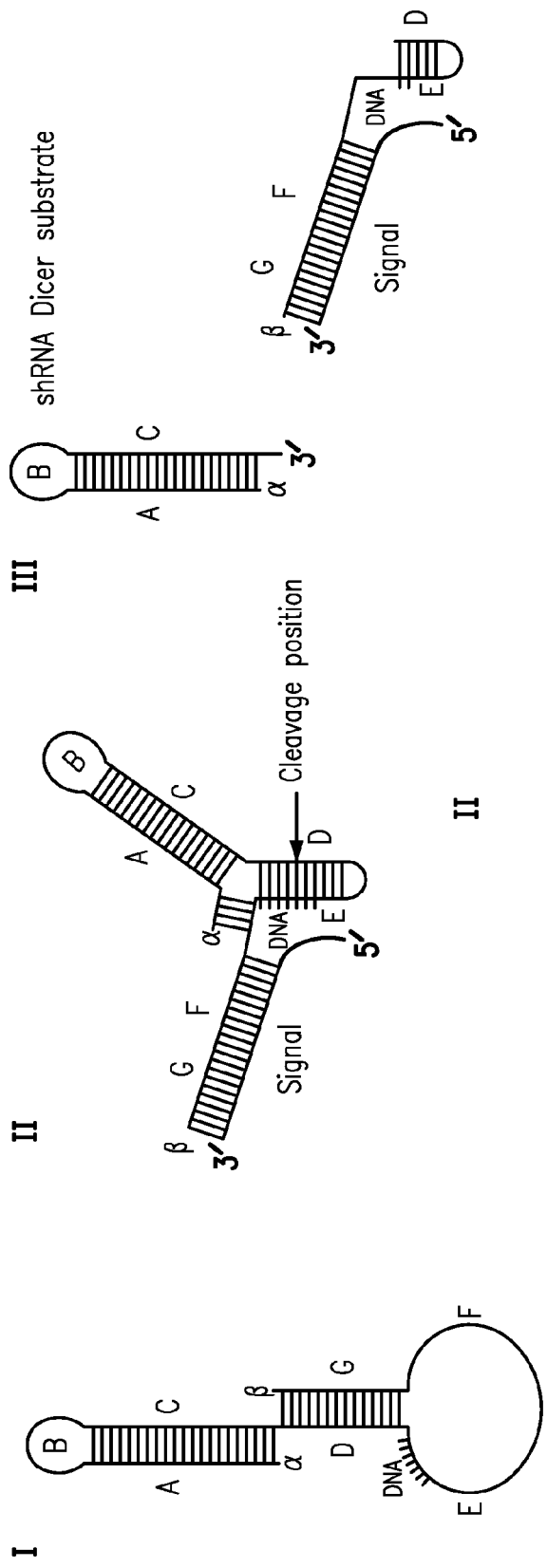
FIG. 10 shows a schematic illustration of an exemplary embodiment of the signal activatable construct wherein the toehold segment (F) and the activation segment (E), are arranged in a loop between the protection segment (D) and the displacement segment (G).

In the exemplary schematic illustration of FIG. 10 the targeting domain comprises first segment (A) and second segment (C) and the sensor domain comprises protection segment (D), activation segment (E), displacement segment (G) and toehold segment (F). In particular, FIG. 10(I) shows the construct in an inactive conformation, wherein first segment (A) and second segment (C) are connected via a polynucleotide linker (B), toehold segment (F) is in a loop structure adjacent and covalently linked to activation segment (E) and displacement (F), and the DNA binding portion of activation segment (E) is adjacent to the 3' terminus of protection segment (D) as schematically shown in the figure. FIG. 10(II) shows the construct of Figure (I) in an activated conformation following binding of a suitable signal polynucleotide to the toehold segment (F). FIG. 10(III) shows products of RNAse H cleavage of the activated construct of FIG. 10(II), wherein the released targeting domain is a small hairpin RNA (shRNA) substrate for Dicer or other RNAi loading pathway enzymes.

Figure 11:
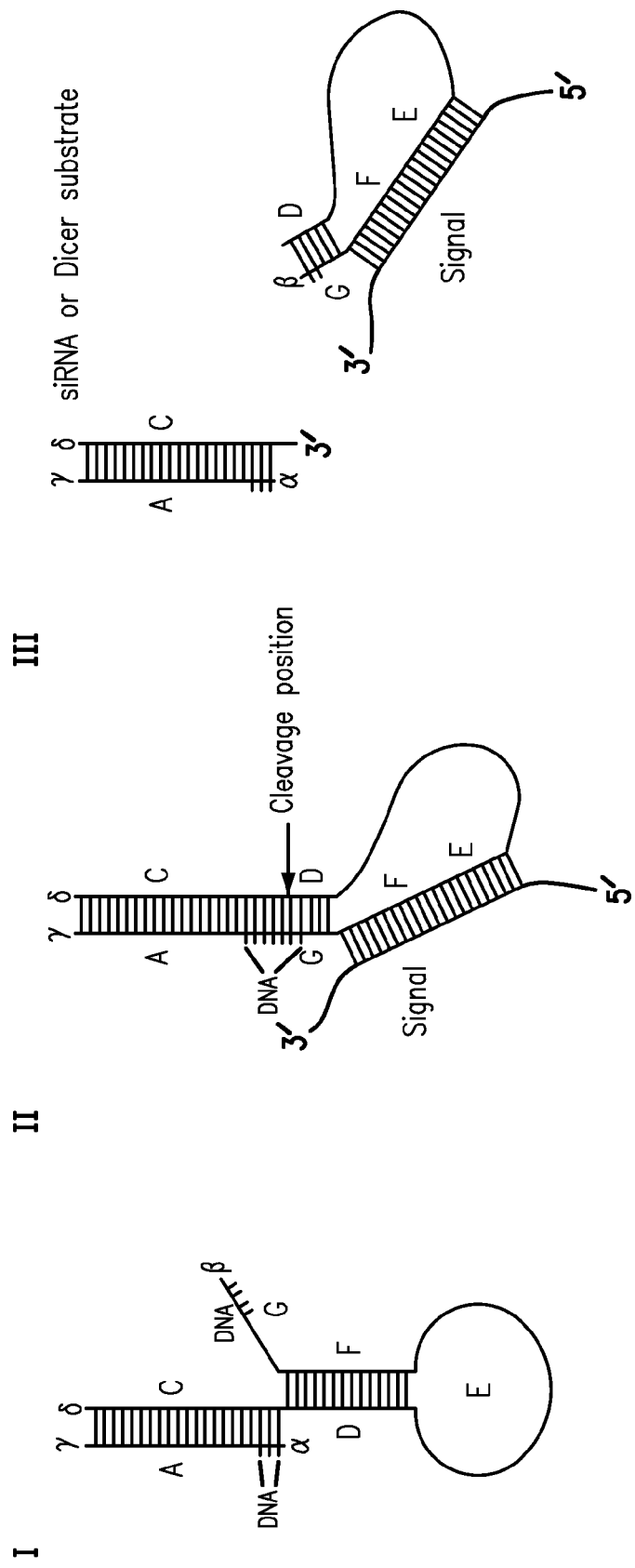
FIG. 11 shows schematic illustration of an exemplary embodiment of the signal activatable construct, where the 5' terminus of a first segment (A) of the targeting domain comprises a DNA portion and presents a terminus opposite to where the DNA portion is located for binding to a third molecule.

In the exemplary schematic illustration of FIG. 11, the targeting domain comprises first segment (A) and second segment (C); and the sensor domain comprises protection segment (D), activation segment (G), displacement segment (F) and toehold segment (E). In particular, FIG. 11(I) shows the construct in an inactive conformation, wherein DNA binding portion in activation segment (G) and in first segment (A) are schematically illustrated. FIG. 11(II) shows the construct of FIG. 11(I) in an activated conformation, wherein following binding of a signal polynucleotide to toehold segment (E), the DNA binding portion of activation segment (G) complementary binds a complementary RNA portion in protection segment (D) thus providing a binding site for RNAase H also formed by the DNA portion of first segment (A) and the complementary portion of second strand (B) as illustrated. FIG. 11(III) shows products of RNAse H cleavage of the activated construct of FIG. 11 (II), in which the released targeting domain comprise a double-stranded duplex which has a blunt end at the 3' of the first segment and an at least 2-base single stranded overhang at the 3' of the second segment and thus can be used as a siRNA or a suitable substrate for Dicer. A skilled person will understand that modifications of the construct can be performed to achieve a blunt end of the targeting domain or a 1-base overhang based on the configuration and location of the enzyme-binding site in the construct.

Figure 12:
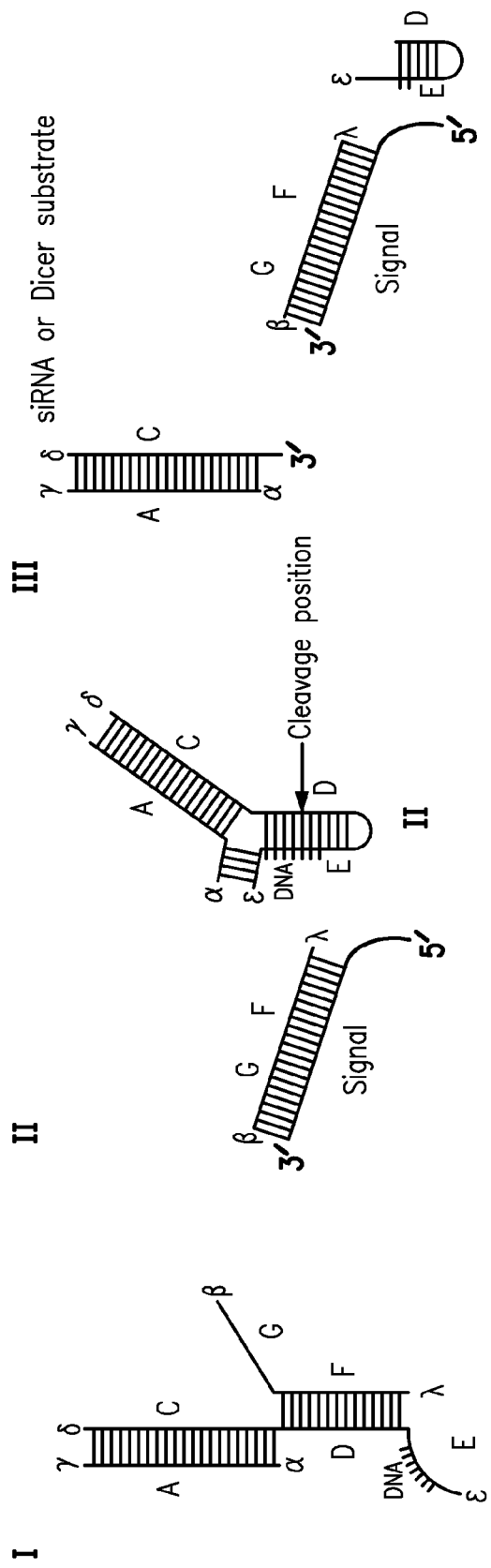
FIG. 12 shows schematic illustration of an exemplary embodiment of the signal activatable construct, where the activation segment (E) is arranged as a single strand overhang at the 5' terminus of the protection segment (D).

In the exemplary schematic illustration of FIG. 12, the targeting domain comprises first segment (A) and second segment (C); and the sensor domain comprises protection segment (D), activation segment (E), displacement segment (F) and toehold segment (G). In particular, FIG. 12(I) shows the construct in an inactive conformation, wherein activation segment (E) is disconnected from displacement segment (F), and is therefore arranged as a single-stranded overhang at the 3' terminus of protection segment (D), and wherein the DNA portion of activation segment (E) is schematically illustrated. FIG. 12(II) shows the construct in an activated conformation, wherein upon binding of the signal polynucleotide to toehold segment (G) and displacement segment (F), displacement segment (F) and the toehold segment (G) are displaced from the construct and the DNA portion of activation segment (E) base pairs to a RNA portion at the junction of second segment (C) and protection segment (D), forming a DNA:RNA duplex suitable for RNase H cleavage. In the illustration of FIG. 12(II), the portion of activation segment (E) flanking the DNA:RNA duplex complementarily binds to a portion of first segment (A) that is displaced from binding to a corresponding portion of second segment (C) by the DNA portion of activation segment (E) forming a three-way activation junction. FIG. 12(III) shows products of RNAse H cleavage of the activated construct of FIG. 12(II), wherein the targeting domain is formed by a double-stranded structure, comprising first segment (A) and second segment (C) released from a remanent comprising activation segment (E) and protection segment (D) as well as nu toehold segment (G) and displacement segment (F) complementary bound to a signal polynucleotide.

Figure 13:
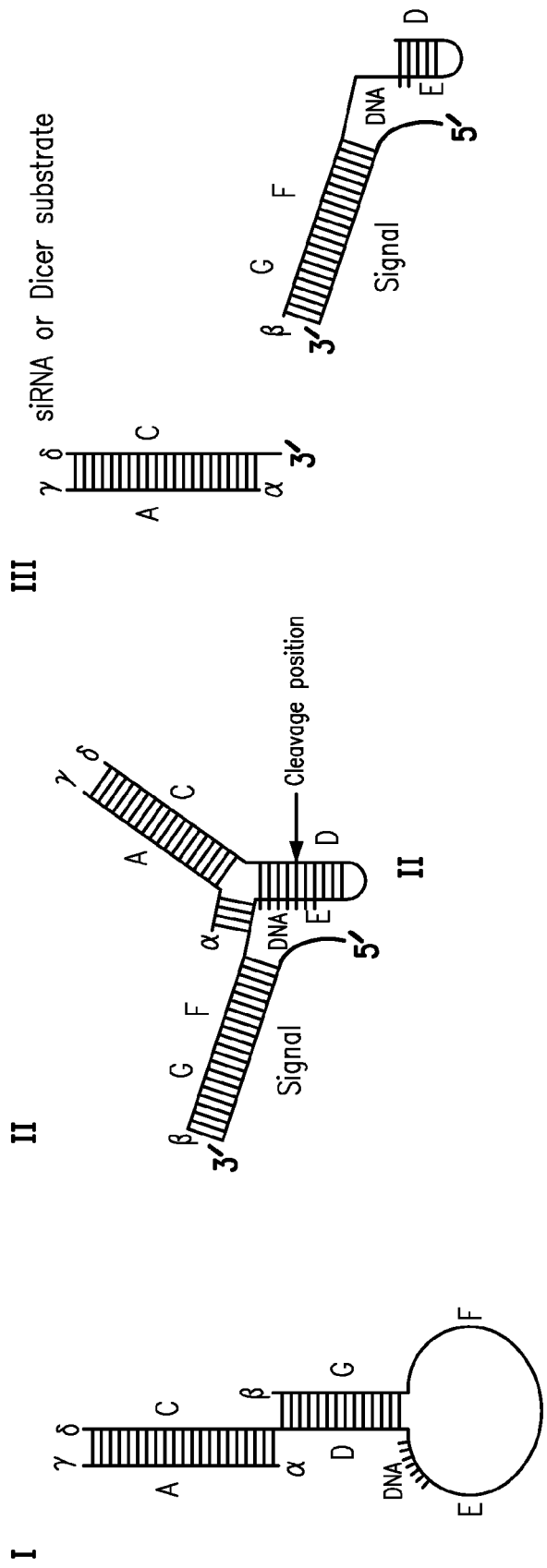
FIG. 13 shows schematic illustration of an exemplary embodiment of the signal activatable construct wherein the toehold segment (F) and the activation segment (E), are arranged in a loop between the protection segment (D) and the displacement segment (G) and wherein the 5' terminus of a first segment (A) of the targeting domain comprises a DNA portion and presents a terminus opposite to where the DNA portion is located for binding to a third molecule.

In the exemplary schematic illustration of FIG. 13, the targeting domain comprises first segment (A) and second segment (C); and the sensor domain comprises protection segment (D), activation segment (E), displacement segment (G) and toehold segment (F). In particular, FIG. 13(I) shows the construct in an inactive conformation wherein the DNA binding portion of activation segment (E) is adjacent to protection segment (D) as schematically illustrated. FIG. 13(II) shows the construct of FIG. 13(I) in an activated conformation, wherein upon binding of the signal polynucleotide to toehold segment (F) and displacement segment (G), protection segment (D) is displaced from displacement segment (G), and the DNA portion of activation segment (E) base pairs to a RNA sequence located at the junction of second segment (C) and protection segment (D), forming a DNA:RNA duplex suitable for RNase H cleavage. In the illustration of FIG. 13(II), the portion of activation segment (E) which is not comprised in the DNA:RNA duplex defining the RNAas H binding site complementarily binds to a portion of first segment (A) that is displaced from binding to a corresponding portion of the second segment by the DNA portion of activation segment (E) forming a three-way activation junction. FIG. 13(III) shows products of RNAse H cleavage of the activated signal activated construct. The targeting domain of a double-stranded structure, comprising the first segment and second segment is released from a remanent comprising activation segment (E), protection segment (D), displacement segment (G), toehold segment (F) and the signal polynucleotide. The released double-stranded duplex has a blunt end at the 3' of the first segment and an at least 5-base single stranded overhang at the 3' of the second segment and therefore can be used as a siRNA or a suitable substrate for Dicer.

Figure 14:
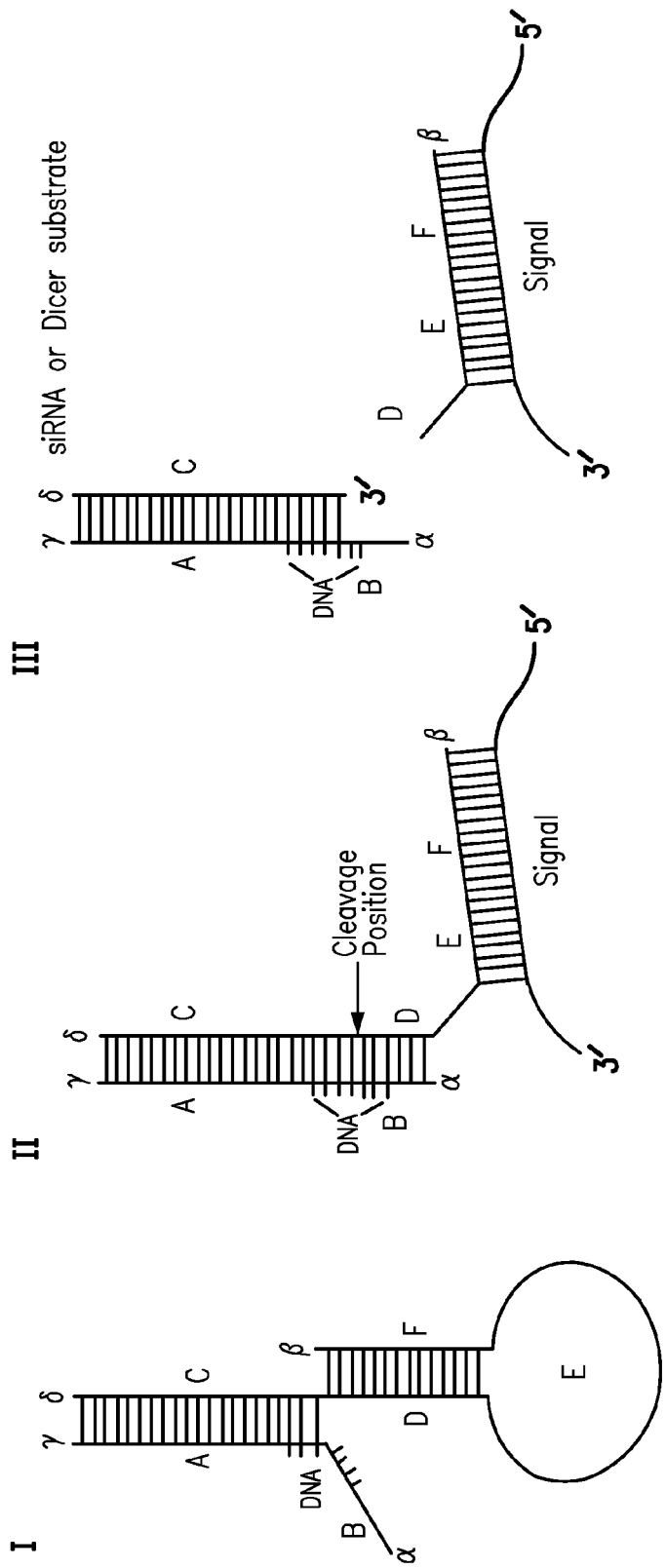
FIG. 14 shows schematic illustration of an exemplary embodiment of the signal activatable construct wherein the 5' terminus of first segment (A) of the targeting domain comprises a DNA portion as indicated and the activation segment (B) is arranged as a single strand overhang at the 5' terminus of first segment (A) with the DNA portion of the activation segment (B) adjacent to the DNA portion comprised in the first segment (A).

In the exemplary schematic illustration of FIG. 14, the targeting domain comprises first segment (A) and second segment (C); and the sensor domain comprises protection segment (D), activation segment (B), displacement segment (F) and toehold segment (E). In particular, FIG. 14(I) shows the construct in an inactive conformation, wherein first segment (A) comprises at one or more consecutive deoxyribonucleotides at the 5' terminus complementing one or more consecutive ribonucleotide located at the 3' terminus of second segment (C). In the illustration of FIG. 14(I), activation segment (B) is arranged as a single strand overhang at the 5' terminus of the first segment, and comprises a DNA activation sequence that is complementary to a corresponding RNA activation sequence located in protection segment (D). In the illustration of FIG. 14(I), toehold segment (E) is arranged as a loop between protection segment (D) and displacement segment (F). FIG. 14(II) shows the construct of FIG. 14(I), in the activated conformation, the toehold segment and the displacement segment base pairs with the signal polynucleotide, and the DNA activation sequence comprised in activation segment (B) base pairs to the RNA activation sequence located in protection segment (D), forming a DNA:RNA duplex which is adjacent to a DNA: RNA duplex formed by first segment (A) and second segment (C), thus forming a suitable substrate for RNAse H. FIG. 14(III) shows products of RNAse H cleavage of the activated construct of FIG. 14(II). In the illustration of FIG. 14(III), A double stranded polynucleotide comprising first segment (A), second segment (C) and activation segment (B) is released from a remanent comprising toehold segment (E), displacement segment (F), protection segment (D) and the signal polynucleotide. In the illustration of FIG. 14(III), the released targeting domain has a 5' overhang and can be used for attaching and delivering a cargo molecule.

Figure 15:
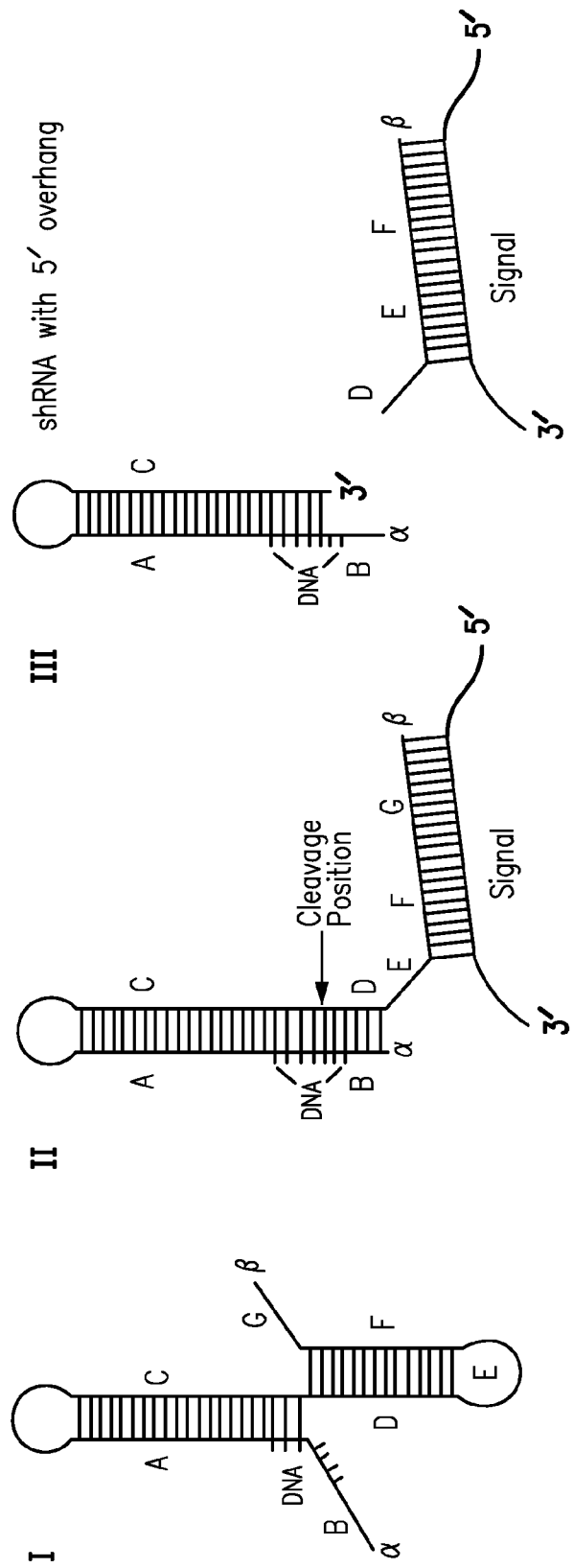
FIG. 15 shows schematic illustration of an exemplary embodiment of the signal activatable construct according to the current disclosure, where the 5' terminus of first segment (A) of the targeting domain comprises a short DNA sequence and the activation segment is arranged as a single strand overhang at the 5' terminus of the first segment with the DNA activation sequence arranged adjacent to the DNA sequence comprised in the first segment.

In the exemplary schematic illustration of FIG. 15 the targeting domain comprises first segment (A) and second segment (C); and the sensor domain comprises protection segment (D), activation segment (B), displacement segment (F) and toehold segment (G). In particular, FIG. 15(I) shows the construct in an inactive conformation, wherein first segment (A) and second segment (C) are connected with a polynucleotide sequence, toehold segment (G) is arranged as a single strand overhang at the 3' terminus of displacement segment (F) and protection segment (D) is connected with the displacement segment through a polynucleotide linker (E). FIG. 15(II) shows the construct in an activated conformation, which is structurally similar to the one as shown in FIG. 14 (II). FIG. 15(III) shows products of RNAse H cleavage of the activated signal activated construct, which are structurally similar to the ones shown in FIG. 14(III). In the illustration of FIG. 15(III), the released targeting domain has a hairpin structure and a 5' overhang and can be suitable for attaching and delivering a cargo molecule.

Figure 16:
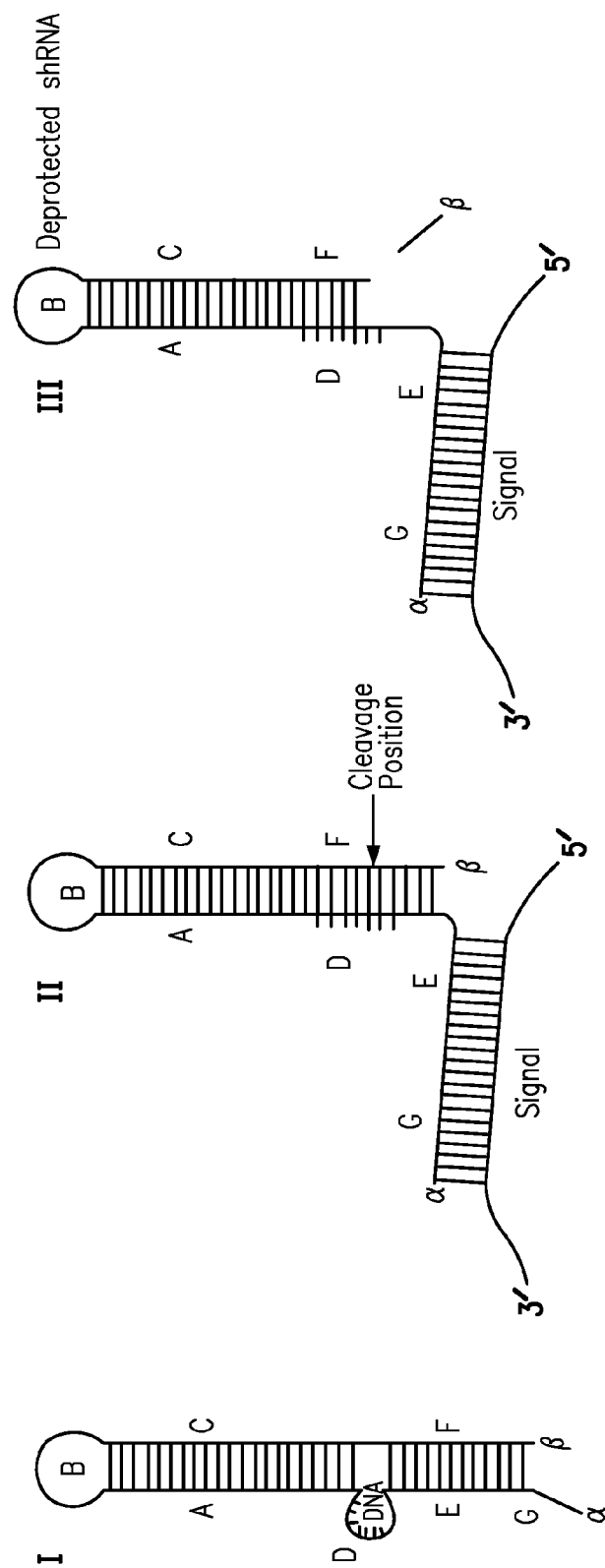
FIG. 16 shows schematic illustration of an exemplary embodiment of the signal activatable construct, wherein activation segment (D) is arranged as a bulge between the first segment (A) of the targeting domain and the displacement segment (E).

In the exemplary schematic illustration of FIG. 16, the targeting domain comprises first segment (A) and second segment (C); and the sensor domain comprises protection segment (F), activation segment (D), displacement segment (E) and toehold segment (F). In particular, FIG. 16(I) shows the construct in an inactive conformation, wherein first segment (A) is connected with second segment (C) with a polynucleotide linker (B). In the illustration of FIG. 16(I), first segment (A), second segment (C), protection segment (F) and displacement segment (E) form a stem loop structure with first segment (A) and second segment (C) base paring with each other in the stem, protection segment (F) and displacement segment (E) base paring with each other in the stem, and polynucleotide linker (B) in the loop. In the illustration of FIG. 16(I), activation segment (D) is arranged as a bulge between first segment (A) and displacement segment (E); toehold segment (F) is arranged as a single strand overhang at the 5' terminus of displacement segment (E). FIG. 16(II) shows the construct of FIG. 16(I) in activated conformation, wherein toehold segment (F) and displacement segment (E) complementary binds to a signal polynucleotide, and the DNA activation sequence comprised in activation segment (D) base pairs to a corresponding RNA activation portion located in protection segment (F) next to the junction of second segment (C) and protection segment (F), forming a DNA:RNA duplex which serves as a suitable substrate for RNAse H. FIG. 16(III) shows the products of RNAse H cleavage of the activated signal activated construct. In the illustration of FIG. 16(III), the cleaved product can be suitable for attaching and delivering a cargo molecule.

Figure 18A:
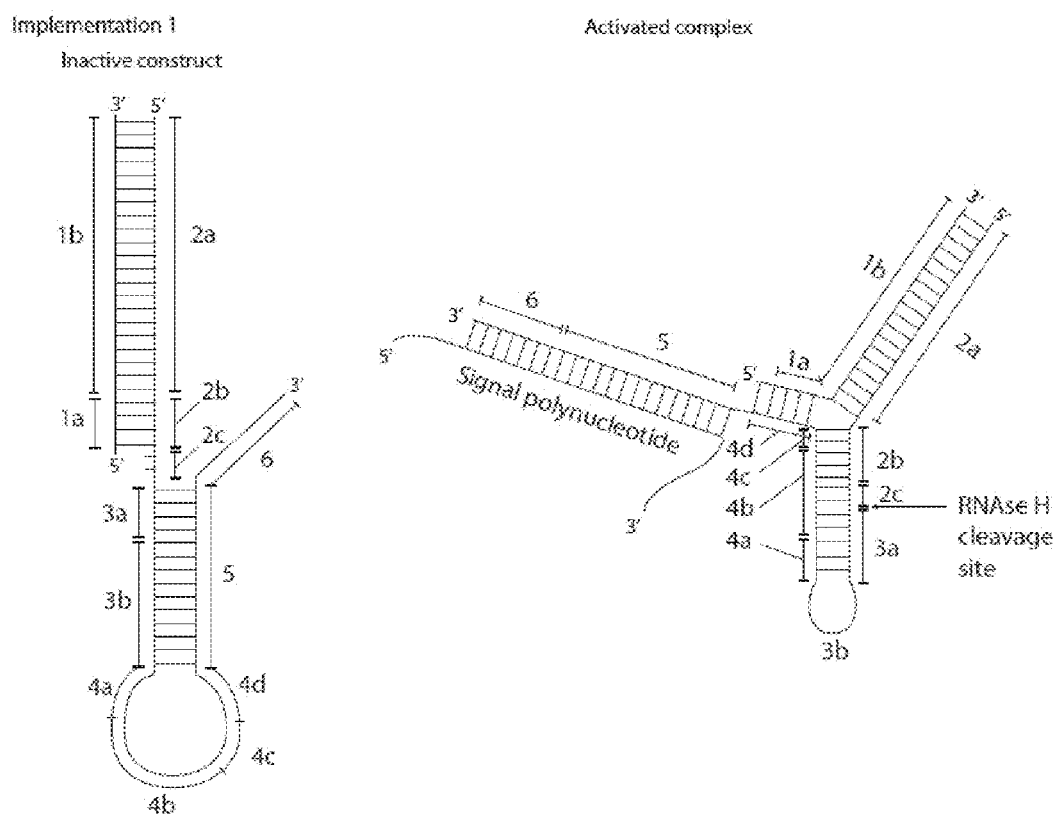
FIG. 18A shows the schematic illustration of the signal activatable construct according to an exemplary embodiment herein described. Left panel shows the construct in the inactive conformation, right panel shows the construct in the activated conformation.
Figure 18B:
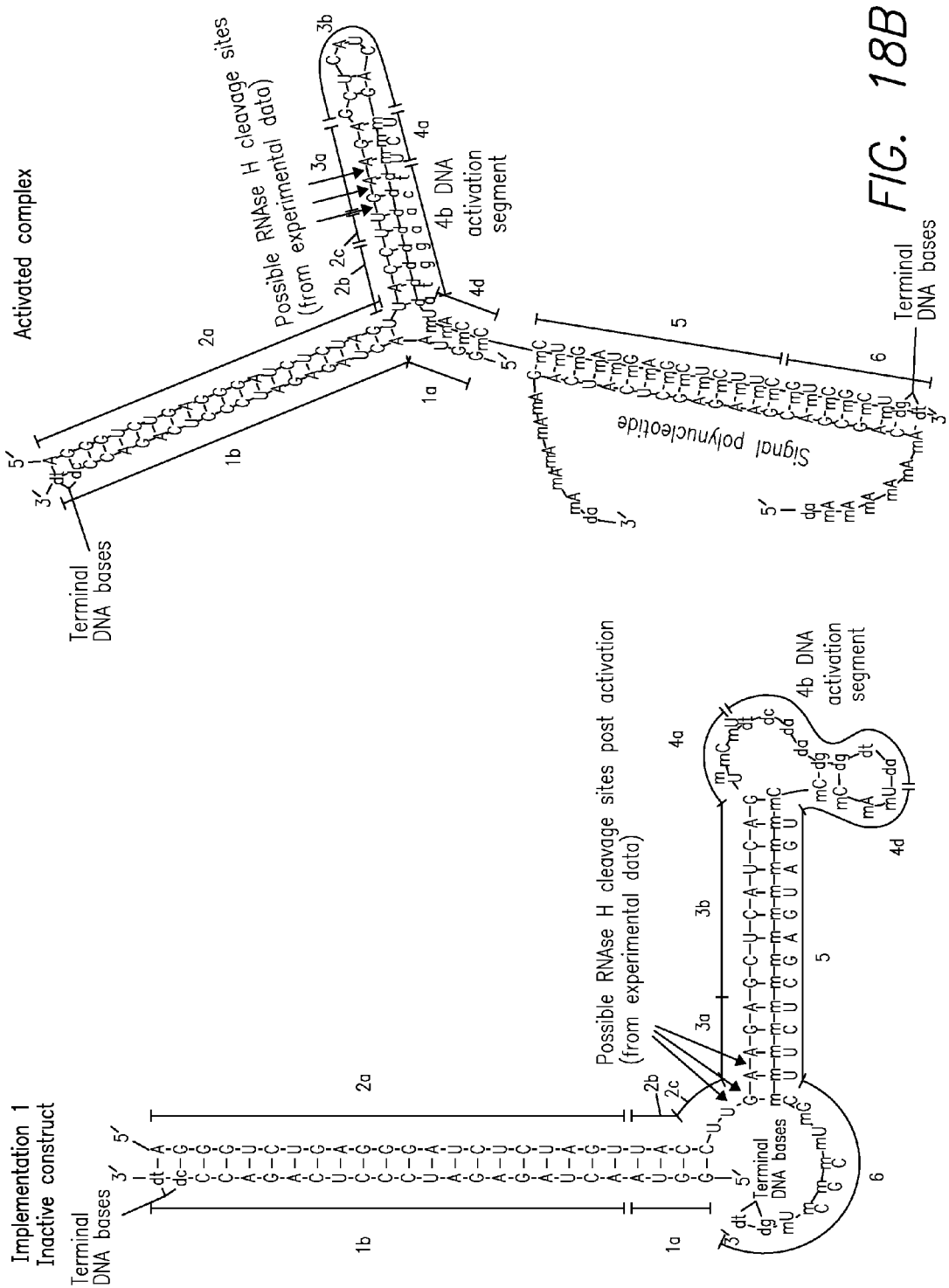
FIG. 18B shows the detailed sequence and structure of the signal activatable construct according to the embodiment as shown in FIG. 18A. Left panel shows the construct in the inactive conformation comprising the toehold, displacement and activation segments (SEQ ID NO: 3), bound to the first segment (1a and 1b) (SEQ ID NO: 1), right panel shows the construct in the activated conformation with the bound signal sequence (SEQ ID NO: 9) bound to the displacement and toehold segments (SEQ ID NO: 10).

FIG. 18A and 18B shows respectively a schematic illustration and detailed structure of an exemplary signal activated construct herein described. In the exemplary schematic illustration of FIGS. 18A and 18B, the construct comprises first segment (1) (SEQ ID NO; 1), second segment (2) (SEQ ID NO: 4), protection segment (3) (SEQ ID NO; 6), activation segment (4) (SEQ ID NO: 7), displacement segment (5)SEQ ID NO: 8), and toehold segment (6). In particular, first segment (1) (SEQ ID NO: 1) comprises portions (1a) and (1b) (SEQ ID NO: 2); second segment (2) (SEQ ID NO: 4) comprises portions (2a) (SEQ ID NO: 5), (2b) and (2c); protection segment (3) (SEQ ID NO: 6) comprises portions (3a) and (3b); activation segment (4) (SEQ ID NO: 7) comprises portions (4a) to (4d). The segments (2) to (6) comprise SEQ ID NO: 3.

FIG. 18A left panel shows the construct in the inactive conformation. In particular, (1b) complementarily binds to (2a); (1a) complementarily binds (2b); (3) inclusive of (3a-3b) complementarily binds to (5); (4) inclusive of (4a-4d) is arranged as a single-stranded loop; (6) is arranged as a single stranded overhang at the 3' terminus of (5). FIG. 18A right panel shows the construct of FIG. 18A left panel in activated conformation. In particular, in the illustration of FIG. 18A right panel a signal polynucleotide complementarily binds to (6) and (5), displacing (3) from complementarily binding to (5), and allowing (4) to complementarily bind to complementary portions of (1), (2) and (3), forming a three-way activation junction. In particular, 4d complementarily binds to 1a; 4a-4c complementarily binds to (2b), (2c) and (3a). In the illustration of FIG. 18A right panel (3b) is arranged as a single-stranded loop.

FIG. 18B shows the detailed sequence and structure of the construct shown in FIG. 18A. FIG. 18B left panel shows the construct in an inactive conformation. In particular, first segment (1a and 1b) (SEQ ID NO: 1) and second segment (2a-2c) (SEQ ID NO: 4) complementarily bind to each other to form a 25 base-pair double stranded duplex. In the illustration of FIG. 18B left panel, protection segment (3a-3b) (SEQ ID NO: 6) and displacement segment (5) (SEQ ID NO: 8) form a 14 base-pair double stranded duplex, activation segment (4a to 4d) (SEQ ID NO: 7) comprises a DNA activation (4b) sequence of 8 deoxylnucleotides, and is arranged as a single-stranded loop. In the illustration of FIG. 18B left panel, toehold segment (6) comprises 8 nucleotides, and is arranged as a single-stranded overhang at the 3' terminus of the displacement segment (5) (SEQ ID NO: 8). In particular, in the illustration of FIG. 18B left panel, first segment (1a-1b) (SEQ ID NO: 1) comprises 2 deoxylribonucleotides at its 3' terminus, displacement segment (5) (SEQ ID NO: 8) comprises 14 methylated ribonucleotides, and toehold segment (6) comprises 8 methylated ribonucleotides. In the illustration of FIG. 18B left panel in addition to the DNA activation sequence (4b), activation segment (4) (SEQ ID NO: 7) also comprises 7 methylated ribonucleotides. FIG. 18B right panel shows the construct of FIG. 18B left panel in an activated conformation. In particular, a signal polynucleotide (SEQ ID NO: 9) complementarily binds to toehold segment (6) and displacement segment (5) (SEQ ID NO: 10), which displace protection segment (3a-3b) (SEQ ID NO: 6) from displacement segment (5) (SEQ ID NO: 8), and allows activation segment (4a-4d) (SEQ ID NO: 7) to complementarily bind to complementary portions of first segment (1) (SEQ ID NO: 1), second segment (2) (SEQ ID NO: 4) and the protection segment (3) (SEQ ID NO: 6), forming a three-way activation junction. In particular, in the illustration of FIG. 18B right panel, (4d) complementarily binds to (1a); (4a) and (4b) complementarily binds to (2b), (2c) and (3a), forming a DNA: RNA duplex suitable for RNAse H cleavage. (3b) is arranged as single-stranded loop.

Figure 18C:
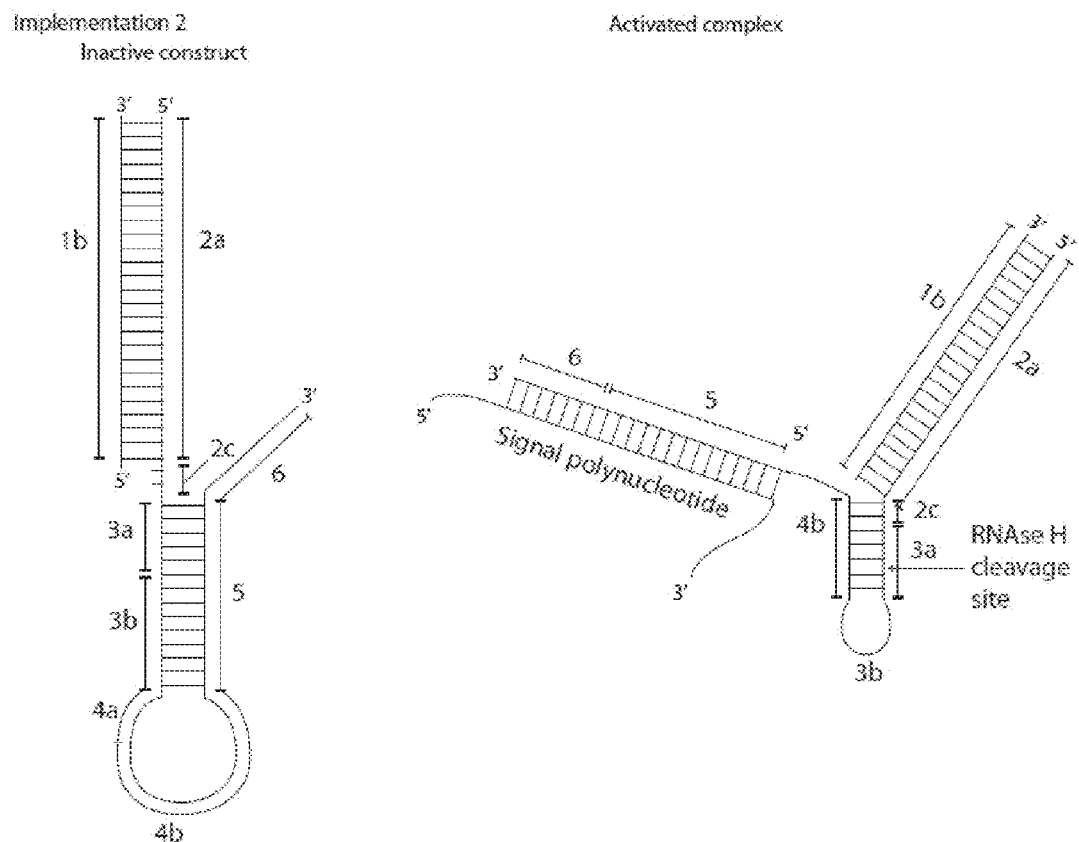
FIG. 18C shows the schematic illustration of the signal activatable construct according to an exemplary embodiment herein described. Left panel shows the construct in the inactive conformation, right panel shows the construct in the activated conformation.
Figure 18D:
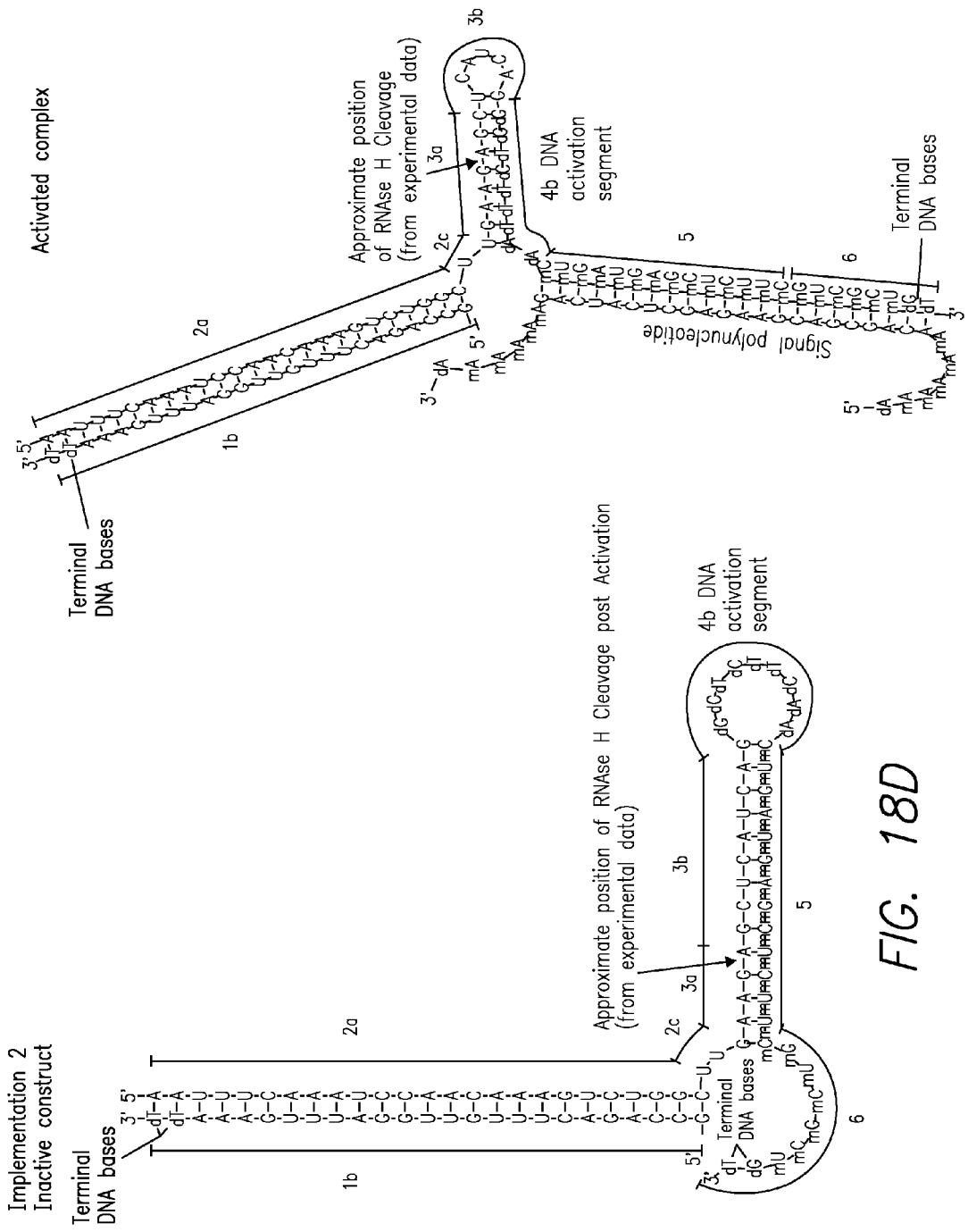
FIG. 18D shows the detailed sequence and structure of the signal activatable construct (SEQ ID NO: 11 and SEQ ID NO: 12) according to the embodiment as shown in FIG. 18C. Left panel shows the construct in the inactive conformation, right panel shows the construct in the activated conformation with the bound signal sequence (SEQ ID NO: 17) bound to the displacement and toehold segments (SEQ ID NO: 18).

FIGS. 18C and 18D shows respectively a schematic illustration and detailed structure of an exemplary signal activated construct herein described. In the exemplary schematic illustration of FIGS. 18C and 18D, the construct comprises first segment (1) (SEQ ID NO: 11), second segment (2) (SEQ ID NO: 13), protection segment (3) (SEQ ID NO: 15), activation segment (4), displacement segment (5) (SEQ ID NO: 16), and toehold segment (6). In particular, first segment (1) (SEQ ID NO: 11) comprises portion (1b) (SEQ ID NO: 11); second segment (2) (SEQ ID NO: 13) comprises portions (2a) (SEQ ID NO: 14) and (2c); protection segment (3) (SEQ ID NO: 15) comprises portions (3a) and (3b); activation segment (4) comprises portions (4a) and (4b). FIG. 18C left panel shows the construct in the inactive conformation. In particular, in the illustration of FIG. 18C left panel (1b) complementarily binds to (2a) segment (3) inclusive of (3a-3b) complementarily binds to (5); segment (4) inclusive of (4a-4b) is arranged as a single-stranded loop; segment (6) is arranged as a single stranded overhang at the 3' terminus of (5). FIG. 18C right panel shows the construct of FIG. 18C in activated conformation. In particular, in the illustration of FIG. 18C right panel, a signal polynucleotide complementarily binds to (6) and (5), thus displacing (3) from complementarily binding to (5), and allowing (4b) to complementarily bind to (3a). In the illustration of FIG. 18C right panel (3b) is arranged as a single-stranded loop. FIG. 18D shows a detailed sequence and structure of the construct of FIG. 18C. Left panel shows the construct in an inactive conformation comprising segment 1b (SEQ ID NO:11) and segments 2 through 6 (SEQ ID NO: 12). In particular, in the illustration of FIG. 18D left panel first segment (1b) (SEQ ID NO: 11) and second segment (2a and 2c) (SEQ ID NO: 13) complementarily bind to each other to form a 25 base-pair double stranded duplex and first segment (1b) (SEQ ID NO: 11) comprises 2 deoxylribonucleotides at its 3' terminus. In the illustration of FIG. 18D left panel, protection segment (3a-3b) (SEQ ID NO: 15) and displacement segment (5) (SEQ ID NO: 16) form a 14 base-pair double stranded duplex; activation segment (4b) comprises a DNA activation sequence (4b) of 9 deoxylnucleotides, and is arranged as a single-stranded loop. In the illustration of FIG. 18D left panel, toehold segment (6) comprises 8 nucleotides, and is arranged as a single-stranded overhang at the 3' terminus of displacement segment (5) (SEQ ID NO: 16). As shown in FIG. 18D left panel, displacement segment (5) (SEQ ID NO: 16) comprises 14 methylated ribonucleotides, and toehold segment (6) comprises 8 methylated ribonucleotides. FIG. 18D right panel shows the construct of FIG. 18D left panel in an activated conformation. In particular, in the illustration of FIG. 18D right panel a signal polynucleotide (SEQ ID NO: 17) complementarily binds to toehold segment (6) and displacement segment (5) (SEQ ID NO: 18), displacing protection segment (3a-3b) (SEQ ID NO: 15) from binding to displacement segment (5) (SEQ ID NO: 16), and allowing activation segment (4b) to complementarily bind to the terminal nucleotide of second segment (2) (SEQ ID NO: 13) and a portion of protection segment (3a) to form a DNA:RNA duplex suitable for RNAse H cleavage., while the residual potion of protection segment (3b) forms a single-stranded loop.

Figure 18E:
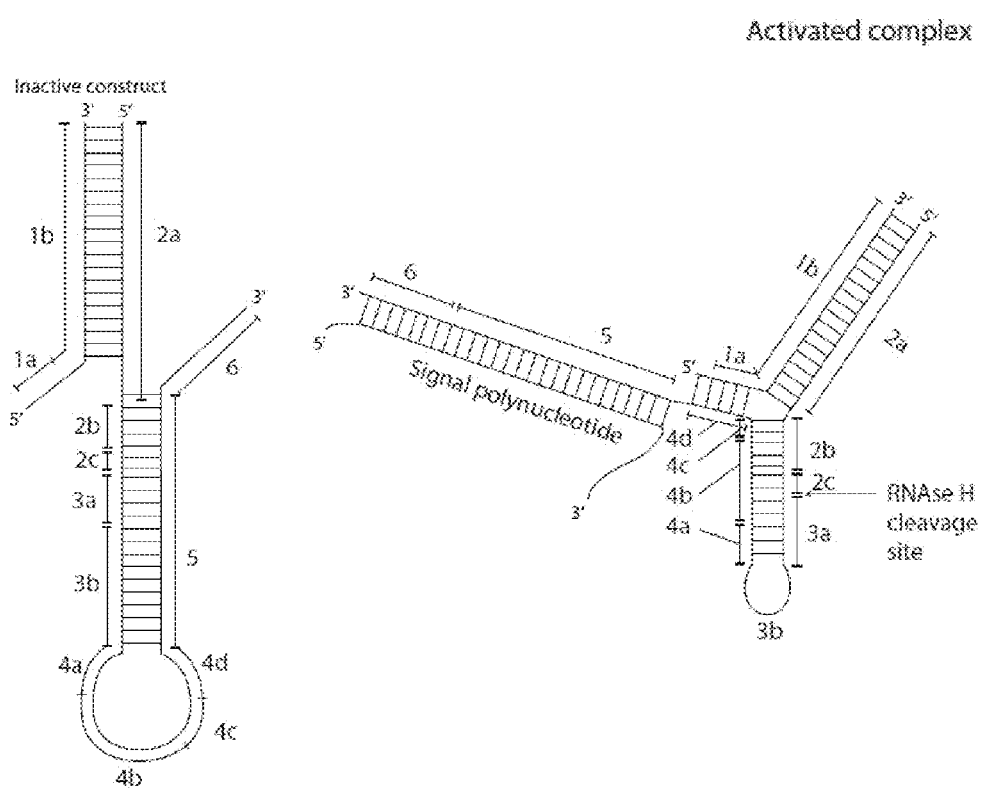
FIG. 18E shows the detailed sequence and structure of the signal activatable construct according an exemplary embodiment herein described. Left panel shows the construct in the inactive conformation, right panel shows the construct in the activated conformation.

FIG. 18E shows a schematic illustration of an exemplary signal activated construct herein described in an inactive conformation (left panel) and in an active conformation (right panel). In the exemplary schematic illustration of FIG. 18E, the construct comprises first segment (1), second segment (2), protection segment (3), activation segment (4), displacement segment (5), and toehold segment (6). In particular, in the illustration of FIG. 18E, first segment (1) comprises portions (1a) and (1b); second segment (2) comprises portions (2a), (2b), (2c); protection segment (3) comprises portions (3a) and (3b); activation segment (4) comprises portions (4a), (4b), (4c), and (4d). In the illustration of FIG. 18E, a signal polynucleotide can have an overlapping area with the targeting domain. FIG. 18E left panel shows the construct in an inactive conformation. In particular, displacement segment (5) complementarily binds to portions of second segment (2b and 2c) and protection segment (3a and 3b). In the illustration of FIG. 18E left panel, activation segment (4) is arranged as a single-stranded loop, toehold segment (6) is arranged as a single-stranded overhang at the '3 terminus of displacement segment (5). FIG. 18E right panel shows the construct of FIG. 18E left panel in an activated conformation. In particular, in the illustration of FIG. 18E right panel, a signal polynucleotide binds to toehold segment (6) and displacement segment (5), displacing both protection segment (3) and the portions (2b) and (2c) from displacement segment (5) and allowing portions (4c, 4b and 4a) of the activation segment (4) to complementarily bind to complementary portions (2b, 2c, 3a) of second segment (2) and protection segment (3). Additionally, in the illustration of FIG. 18E, portion (4d) complementarily binds to (1a), forming a three-way activation junction and portion (3b) is arranged in a loop.

Signal activatable constructs and related components herein described can be designed and manufactured based on techniques described herein and/or identifiable by the skilled person upon reading of the present disclosure. In particular the configuration of the segments of the constructs can be identified and designed based on calculation of the thermodynamic stability of the various conformation of the segments and constructs as a whole. For example, thermodynamic stability of polynucleotide conformation dependents on several factors identifiable by a skilled person, including its i) chemical composition (for example, DNA:RNA duplex is less than RNA: RNA duplex); ii) base composition (for example, G/C base paring is more stable than A/T base paring, which is approximately as stable as G/T, G/U wobble base pairing, and the formation of a stable RNA hairpin requires at least 3 G/C base pairs or at least 5 A/U, G/U base pairs); iii) nearest neighbors such as presence of mismatches, open ends, and junctions near a base-pair can substantially influence its energy contribution according to the second-nearest neighbor model (for example, the stacking of successive base-pairs is primarily responsible for the stability of DNA helices); iv) non-canonical base pairing (for example, RNA and DNA can form triple helix and quadraplex structures via Hoogsteen base-pairing, which is less stable base pairings than canonical base pairing); v) Geometry (e.g. polynucleotide sequences can only adopt secondary structures that are geometrically consistent or similar with the known tertiary structural characteristics of RNA and DNA helices); vi) Environmental factors, such as pH value, counter-ion concentration and temperature and additional factors identifiable by a skilled person.

Accordingly, designing the polynucleotide sequences comprised in the signal activatable construct can be performed identifying the combination of length, sequence, complementarity and substitutions that is associated with a desired relative thermodynamic stability resulting in the configuration herein described and the environment wherein the enzyme assisted molecular delivery is desired. For example, in several embodiments, in absence of a signal polynucleotide, an inactive conformation of the signal activatable construct typically has approximately 3 extra G/C base pairs or 5 extra A/U or G/U base pairs as compared to the activated conformation formed in presence of the signal polynucleotide. Specific sequences of desired signal polynucleotides can be identified by a skilled person based on environment (and in particular, specific cells and tissues) where delivery is desired. Also, the number of complementary base pairs between the protection segment and displacement segment is typically more than that between the protection segment and the activation segment. For applications where molecular delivery in cells is desired, polynucleotide sequences can be designed according to the corresponding physiological conditions, such as approximately, pH 7.3-7.4, about 150 millimolar potassium or sodium chloride or equivalent salt, and about 37° C.

For base pairing between unmodified DNA segments or between unmodified RNA segments, the base-pairing energies and the most stable secondary structure conformations can be estimated by computational methods known to and well established in the art. Several packages are available and published in documents also discussing in detail factors affecting the energy and stability of nucleic acid secondary structures. Exemplary publications describing the packages and factore comprise for i) *NUPACK web server*: J. N. Zadeh, et al., (2011); ii) *NUPACK analysis algorithms*: R. M. Dirks et al., (2007); R. M. Dirks et al., (2003); R. M. Dirks et al., (2004); iii) *NUPACK design algorithms*: J. N. Zadeh et al., (2011); iv) *mfold web server*: M. Zuker, (2003); A. Waugh et al., (2002); M. Zuker et al., (1998); v) UNAFold & mfold: N. R. Markham et al., (2008); M. Zuker, et al., (1999); M. Zuker, (1994); J. A. Jaeger et al., (1990); M. Zuker, (1989); vi) *Free energies for RNA*: D. H. Mathews et al., (1999); A. E. Walter et al., (1994); vii) *Methods and theory of RNA secondary structure prediction*: D. H. Mathews et al., (2007); D. H. Mathews et al., (2006); D. H. Mathews et al. $3^{rd}$ edition, John Wiley & Sons, New York, Chapter 7, (2005); D. H. Mathews et al., (2004); M. Zuker, (1984); M. Zuker et al., (1981); viii) *Exemplary mfold & UNAFold applications*: J.-M. Rouillard et al., (2003); J.-M. Rouillard, et al., (2002). In addition, since some polynucleotide structures typically fluctuate between an ensemble of secondary structure conformations, the composition of the relevant ensemble can be determined using computational methods known in the art (see for example, see Ye Ding et al., (2005), herein incorporated by reference in its entirety).

Accordingly, in several embodiments, design of a polynucleotide sequence of the sensor domain of the signal activatable construct herein described, can be performed for sequences or portions of sequences consisting of unmodified DNA and/or RNA base pairs, by computational methods and/or software packages to calculate the free energy of the sequence and the secondary structure conformation. In embodiments, wherein polynucleotide sequences comprise derivatives of nucleotides, such as chemically modified bases and analogues, and/or chimeric polynucleotide sequences composed of a mixture of deoxyribonucleotides and ribonucleotides, design can be performed by computationally designing unmodified RNA structures with the desired secondary structure conformations and thermodynamic stability, and then introducing one or more chemical modifications to achieve the desired thermodynamic stability. Exemplary chemical modifications comprise replacement of nucleotides that are needed to be base-paired to form a desired secondary structure with modified nucleotides that are known to increase thermodynamic stability (e.g. 2'-O-methyl modified nucleotides, LNA, PNA and Morpholino). Additional exemplary modifications comprise replacement of nucleotides that are not desired according to a certain thermodynamic stability with modified nucleotides to ensure that the resulting modified structures are likely to retain the desired secondary structure conformations and thermodynamic stability (e.g. replace a ribonucleotide base with a deoxyribonucleic base). A person skilled in the art will be able to identify other suitable modifications upon reading of the current disclosure.

The signal activatable construct designed according the present disclosure can be synthesized using standard methods for oligonucleotide synthesis well establish in the art, for example, see Piet Herdewijn, (2005), herein incorporated by reference in its entirety.

The synthesized oligonucleotide can be allowed to form its secondary structure under a desirable physiological condition, (e.g. 1× phosphate buffered saline at pH 7.5 with 1 mmolar concentration $MgCl_2$ at 37° C.). The formed secondary structure can be tested using standard methods known in the art. For example, see Stephen Neidle, (2008), herein incorporate by reference in its entirety. The designed construct can be further modified, according to the test result, by introducing or removing chemical modifications, mismatches, wobble pairings, as necessary, until the desired structure is obtained. Exemplary detailed structures of two constructs are shown in FIG. 18A FIG. 18B (SEQ ID NO: 1 and SEQ ID NO: 3) and FIG. 18D (SEQ ID NO: 11 and SEQ ID NO: 12).

In some embodiments, in presence of a signal polynucleotide, the free energy of the construct in an activated conformation is at least about 5 kcal/mol lower than that of the construct in an inactive conformation.

In some embodiment, the free energy of complementary base-paring between the protection segment and the displacement segment is at least about 10 kcal/mol lower that the free energy of complementary base-pairing between the DNA activation sequence and the RNA activation substrate.

In some embodiment, the targeting domain comprises a first segment and a second segment, wherein the first segment and the second segment form a polynucleotide duplex through complementarily binding with each other; and the 3' terminus of the second segment is adjacently connected with the protection segment of the sensor domain.

In some embodiments, the first segment, second segment, protection segment, activation segment, displacement segment and toehold segment of the signal activatable construct are mainly composed of RNA and/or RNA derivatives. In those embodiments, the activation segment also comprises a DNA portion complementary to a corresponding portion of the protection segment defining the RNAase H binding site.

The term "derivative" as used herein with reference to a first compound (e.g. RNA or ribonucleotide) indicates a second compound that is structurally related to the first compound and is derivable from the first compound by a modification that introduces a feature that is not present in the first compound while retaining functional properties of the first compound. Accordingly, a derivative of a molecule of RNA, usually differs from the original molecule by modification of the chemical formula that might or might not be associated with an additional function not present in the original molecule. A derivative molecule of RNA retains however one or more functional activities that are herein described in connection with complementary base paring with other nucleotides. Typically, ribonucleotides and deoxyribonucleotides can be modified at the 2', 5', or 3' positions or the phosphate backbone chemistry is replaced. Exemplary chemical modifications of a ribonucleotide according to the current disclosure include 2'-o-methyl RNA, 2'-Fluoro RNA, locked nucleic acid (LNA), peptide nucleic acid (PNA), morpholino, phosphorothioate oligonucleotides, and the like that are identifiable by a skilled person (see e.g. "Modified Nucleosides: in Biochemistry, Biotechnology and Medicine. Piet herdewijn (Editor), Wiley-VCH, 2008, herein incorporated by reference in its entirety). Also applicable are nucleosides which are not normally comprised in DNA and RNA polynucleotides, such as inosine. In some embodiments, a single oligonucleotide can be composed of more than one type of the above derivatives.

In particular, according to several embodiment herein described, the first segment and the second segment in the targeting domain comprise unmodified ribonucleotides. In other embodiments, the first segment and the second segment in the targeting domain can comprise modified ribonucleotides, such as 2'-O-methyl modification, 2'-fluoro modification, 2'-amino modification or LNA; the exposed 3' terminus of the first segment can have modifications configured to block processing by the endonucleases enzyme Dicer. For example, 3' terminus of the first segment can have at least 1, and in particular 2 deoxyribonucleotides.

In some embodiments, the protection segment can comprises unmodified ribonucleotides and/or some modified ribonucleotides, such as 2'-O-methyl modification, 2'-fluoro modification, 2'-amino modification or LNA. In particular, in some embodiments, the two nucleotides immediately flanking the desired RNAse H cleavage site within the RNA activation sequence can be formed by unmodified ribonucleotides.

In some embodiments, the activation segment comprises the DNA activation sequence formed by unmodified deoxyribonucleotides.

In some embodiments, the displacement segment and the toehold segment can comprise modified ribonucleotides or derivatives, such as 2'-O-methyl modification, 2'-fluoro modification, 2'-Amino modification or LNA; the exposed terminus of the toehold segment can also have modifications configured to block processing by endonucleases enzyme Dicer. For example, the exposed terminus of the toehold segment can comprise at least one, and in particular two, phosphorothioate deoxyribonucleotides.

In several embodiments, the toehold segment can comprise a polynucleotide sequence (herein also toehold sequence) that is at least 3 nucleotides in length and is fully complementary to at least a portion of the signal polynucleotide. This configuration of the toehold segment is expected to allow binding of a signal polynucleotide to bind to the signal activatable construct and initiate the branch migration process. A smaller toehold sequence is expected to result in better sequence specificity for signal discrimination, while a longer toehold sequence is expected to result in an increased ability to bind to the signal polynucleotides to form a desired secondary structure with respect to the ability of a shorter toehold segment. In some embodiments, the toehold segment can be arranged in single-stranded form and free of secondary structure. In particular, in some of those embodiments, the toehold sequence can be 4 to 12 nucleotides in length. In some embodiments, the toehold segment is composed of unmodified ribonucleotide. In particular, in other embodiments, the toehold segment comprises modified nucleotide configured for improved nuclease resistance. Exemplary modifications include but are not limited to 2'-O-methyl modification, 2'-Fluoro modifications, inclusions of LNA and PNA, and the like that are identifiable by a skilled person.

In some embodiments, the signal can be a single signal polynucleotide of a length shorter than 30 nucleotides, the toehold segment and the displacement segment is fully complementary to the signal polynucleotide. In other embodiments, the signal can be formed by multiple homologous signal polynucleotides. In these embodiments, the signal polynucleotides can be tested with a sensor design. Mismatches and wobble pairings or permissive bases such as inosine can be placed at positions in the 3:5 duplex corresponding to the variable sequences. In particular, in several embodiments, the Tm for the duplex formed by the signal polynucleotides with the toehold segment and the displacement segment is typically at least 25° C. and is typically at least equal to the operating temperature under which the construct will be used. In some embodiments, the 3' terminus of the sensor domain can have Dicer blocking groups which are identifiable by a skilled person.

In some embodiments, where the toehold segment is arranged as or within a single-stranded loop (see exemplary embodiments in FIGS. 6B, 7B, 10, 13), the loop can be sufficiently large to avoid topological constraints that present a kinetic barrier to displacement of the protection segment from binding to the displacement segment by the signal polynucleotide. To test whether the loop is as large as desired, the strand displacement process of the construct can be tested using the methods such as the one described in Example 6. Further, in some embodiments the signal polynucleotide used in the experiment, can be selected to approximate the expected state of the signal in the cell. In particular, in embodiments wherein the signal polynucleotide is expected to be a short oligonucleotide or RNA segment, such as a miRNA, a short oligonucleotide of the same sequence as the signal polynucleotide can be used in experiments to simulate the topological constraints imposed by having the toehold segment in a hairpin loop. In embodiments wherein the signal is an mRNA sequence, a polynucleotide having the same sequence as the mRNA as the signal nucleotide can be used to simulate the topological constraints imposed by having the toehold segment in a hairpin loop. In embodiments wherein the region known to bind to the toehold segment is in a hairpin loop, the signal nucleotide used in the displacement experiment can have the toehold sequence in a hairpin loop to simulate the topological constraints imposed by having the toehold segment in a hairpin loop.

In embodiments wherein strand displacement does not occur, the size of the hairpin loop can be increased to decrease the topological constraint by increasing the loop size. For example, in some embodiments, the size can be increased using an unstructured polynucleotide or polymer linker between the toehold segment and the other segments (e.g. either between the toehold segment and the activation segment or, usually less favorably, between the toehold segment and the displacement segment). In particular in various embodiments, the loop can have at least about 20 unstructured nucleotides.

Single stranded regions in the hairpin loop and in other areas can be protected by chemical modifications if not conflicting with other design objectives. 2'-O-methyl, 2'-fluoro, LNA, 2'-amino and other modified RNA nucleosides can replace RNA. Phosphorothioate deoxyribonucleotides can replace unmodified deoxyribonucleotides for RNAseH segment.

In some embodiment, wherein the sensor domain comprises more than one polynucleotides (see exemplary embodiments in FIGS. 6C, 6D, 12), the melting temperature of the duplex formed by the displacement segment and the protection segment is at least 5° C. above the expected operating temperature under which the construct is used, (e.g. 37° C. for the use in human cells) in order to prevent spurious activation.

In some embodiments, the toehold segment can be connected to the displacement segment through covalent linkage. In particular, in some embodiments, the toehold segment can be arranged to the 3' terminus of the displacement segment (see exemplary embodiments in FIGS. 6B, 10(I), 11(I), 13(I), 15(I), 16(I)). In other embodiments, the toehold segment can be arranged at the 5' terminus of the displacement segment (see exemplary embodiments in FIGS. 1A, 5A-5D, 6A, 6C, 8(I), 9(I), 12(I), 15 (I)). In some embodiments, the toehold segment can be arranged as a single strand terminal sequence of the sensor domain (see exemplary embodiments in FIGS. 1A, 5A-5D, 6A, 6C, 6D, 12(I), 15 (I), 16(I)); in other embodiments, the toehold segment can be provided as a single strand middle sequence of the sensor domain, which can be arranged within a loop structure of the sensor domain (see exemplary embodiments in FIGS., 6B, 8(I), 10 (I), 11(I), 13(I), 14(I)). In particular, in some embodiments, where the toehold domain can be arranged within a loop structure of the sensor domain, the loop can comprise at least 20 nucleotide unmodified nucleotides, which in some cases can be ribonucleotides. In some embodiments, the toehold segment can be at least 3 nucleotides in length. In particular, in some embodiments, the toehold segment can be at least 4 nucleotides in length.

In some embodiments, the activation segment can be kept to the minimum length necessary for efficient formation of an activation junction to kinetically minimize spurious activation usually associated with binding of a large terminal loop in the sensor domain to a partially deprotected activation site as a result of partial displacement of (5) by a partially complementary polynucleotide that is not the intended signal polynucleotide. Accordingly, the activation segment can be at least 5 nucleotides in length, and in particular less than 10 nucleotides in length. Additional lengths of the loop can be identified by a skilled person taking into account that the possibility of having complementary binding of a strand to the loop that result in displacement of the displacement segment from the protection segment in view of a desired experimental design In particular, in some embodiments herein described, the activation segment can be covalently linked to the protection segment. In particular, in some embodiments, the activation segment links the 3' terminus of the protection segment and the 5' terminus of the displacement segment, and can be arranged as a loop between the protection segment and the displacement segment (see exemplary embodiments in FIGS. 1A, 7A, 9(I), 10 (I), 13(I)). In some embodiments, the activation segment can be arranged as a single strand overhang at the 3' terminus of the protection segment (see exemplary embodiments in FIG. 12 (I)).

Alternatively, in some embodiments, the toehold segment links the 3' terminus of the protection segment and the 5' terminus of the displacement segment, and is arranged as a loop between the protection segment and the displacement segment, and the activation segment is arranged at the 3' terminus of the displacement segment (see e.g. FIGS. 7B, 7C and 7D). In particular FIG. 7B shows a schematic illustration of the signal activatable construct in an inactive conformation, where the toehold segment (segment 6) is arranged at the 3' terminus of protection segment (segment 3) and the 5' terminus of the displacement segment (segment 5), and is located in the loop of a stem-loop structure formed by the protection segment and the displacement segment. In the illustration of FIG. 7B, the activation segment (activator) is arranged as a single-stranded overhang at the 3' terminus of the displacement segment. FIG. 7C shows schematic illustration of an activated conformation of the signal activatable construct according to the embodiment as shown in FIG. 7B. In this activated conformation, portions (1b) and (2a) form a double-stranded duplex through base paring, portions (2b), (3a), (3b), (4a) and segment (5), (6) form a stem-loop structure with portion (4a) base paring with both (2b) and (3a) in the stem and portion (3b), segment (5) and (6) in the loop. Portion (4b) binds to portion (1a) and a signal polynucleotide binds to segment (5) and (6) through base paring. The DNA activation sequence of segment 4 base-pairs with the RNA sequence located at the junction of segment (2) and (3) to form a DNA:RNA duplex which serves as a suitable substrate for RNAse H.

In some embodiments, the activation segment is arranged at the 5' terminus of the first segment. In particular, in some embodiments, the activation segment is arranged as a single strand overhang at the 5' terminus of the first segment (see exemplary embodiments shown in FIG. 14 and FIG. 15). In some embodiments, the activation segment can be arranged as a single strand bulge loop between the first segment and the displace segment (see e.g. FIG. 16). In any of those arrangements, the 3' terminus of the second segment can be connected with the protection segment, and the RNA activation sequence can located in the protection segment next to the junction of the second segment and the protection segment. In those embodiments, the activated conformation, the DNA activation sequence binds to both the RNA activation sequence and an adjacent RNA sequence of at least 3 nucleotides located at the 3' terminus of the second segment to form a DNA:RNA duplex which serves as a suitable substrate for RNAase H. Accordingly, in some of those embodiments, a corresponding portion of at least 3 nucleotides in the first segment (portion (1a)) is displaced from binding to the at least 3 nucleotides of the 3' terminus of the second segment (portion (2b)) by the DNA activation sequence. To stabilize the activated conformation, in some embodiments, the activation segment can also comprises a portion of at least 3 nucleotides (portion (4b)) that is complementary to the displaced portion of the first segment (portion (1a)), thus to form a 3-way junction structure in the activated conformation (see exemplary embodiments of shown in FIGS. 2A, 7C, 9(II), 10(II), 12(II), 13(II)). Since a DNA:RNA duplex is usually energetically less stable than an RNA-RNA duplex, in this embodiment, nucleotides in the portion (4b) can be chemically modified to increase the stability of the 3-way junction. Exemplary chemical modifications include but are not limited to 2'-O-methylation, 2'-Fluoro modifications, inclusion of LNA or PNA nucleotides. In particular, in this embodiment, the RNA activation sequence has at least 2 nucleotides in the protection segment (portion 3a). FIG. 2B shows a detailed view of the junction portion of the activated conformation of the signal activatable construct. In the illustration of FIG. 2B, portions (2b), (3a), (3b) and (4a) form a stem-loop structure, with portion (4a) base-paring with portion (2b) and (3a) in the stem and portion (3b) in the loop. In the illustration of FIG. 2B base paring of portion (4a) and (2b) displaces a corresponding region of portion (1a) from binding to portion (2b), which base pairs with portion (4b). In the illustration of FIG. 2B, the DNA activation sequence of segment (4) base-pairs with the RNA sequence located at the junction of segment (2) and (3) to form a DNA:RNA duplex which serves as a suitable substrate for RNAase H.

In some embodiments, in absence of a signal polynucleotide, the displacement segment and the protection segment form a double-stranded duplex. In particular, the double-stranded duplex formed by the displacement segment and the protection segment can have up to 30 consecutive base pairs, if the duplex comprises only unmodified ribonucleotides. In other embodiments, the double-stranded duplex formed by the displacement segment and the protection segment can be longer than 30 base pairs, if the duplex comprises mismatches and/or modified ribonucleotides. In particular, mismatches and/or modifications are expected to contribute to preventing activation of innate immune system and/or increase stability. Exemplary modifications to the first and the second segments include but are not limited to 2'-O-methylation, 2'-Fluoro modifications, 2'-amino modifications, and inclusion of LNA or PNA nucleotides. In particular 2'-O-methylation can be used to passivate against innate immune activation. In some embodiments, the displacement segment is at least 12 nucleotides in length. In some embodiments, the displacement segment can be at least 14 nucleotides in length.

In some embodiments, the construct is configured to minimize immune responses. In these embodiments, each consecutive 30 base pairs duplex can have at least 5% 2'-O-methyl modifications (Molecular Therapy (2006) 13, 494-505, herein incorporated by reference in its entirety) or one or two mismatches. In other embodiments, the construct is configured to stimulate immune responses. In these embodiments, the construct can comprises at least one consecutive 30 base-pair duplex with no 2'-O-methyl modifications when the construct is in the activated conformation. For example, the total length of the toehold segment and the displacement segment can be at least 30 nucleotides without 2'-O-methyl modifications, and will be perfectly base paired with the signal polynucleotide sequence.

In some embodiments, the signal polynucleotide can have an overlapping area with the targeting domain. In some of those embodiments, the displacement segment can complementarily bind to portions of the second segment and the protection segment (see exemplary embodiments in FIG. 18E). In particular, in the inactive conformation, the displacement segment can complementarily bind to portion (2c), and the signal polynucleotide displaces both the protection segment and the portion (2c) from binding to the displacement segment. Thus, the melting temperature of the double-stranded duplex formed by the signal polynucleotide and the displacement segment can be at least about 25° C. Accordingly, the experiment to characterize the strand displacement reaction as described in Example 6 can use a construct comprising both the sensor domain and the targeting domain. In particular, the fluorophore quencher pair can be placed at multiple positions along the duplex formed by the displacement segment and the second segment or the displacement segment and the protection segment to allow assessment of strand displacement.

In an activated conformation of the activatable construct herein described or related component (e.g. sensor domain), a DNA portion comprised in the activation segment (herein also DNA activation sequence or portion) binds to an RNA portion comprised in the protection segment (herein RNA activation sequence) through complementary base paring to form a RNAase H binding site.

In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. Accordingly, the DNA:RNA duplex formed in the activated conformation according to the current disclosure can be at least 5 nucleotides, and in particular 7-8 nucleotides. In particular, in some embodiments, the DNA activation sequence is no longer than 10 nucleotides. In particular, in several embodiments, an RNAase H cleavage site comprises a DNA:RNA duplex of at least 5 consecutive base pairs, in particular, the DNA: RNA duplex has 7 consecutive base pairs. In some embodiments, cleavage rate is expected to increase if 8 or more consecutive base pairs are present in the duplex, but there will be multiple cleavage sites. Higher Tm of the DNA:RNA duplex is expected to generally improve cleavage efficiency. In some embodiments, Tm can be greater than or equal to the expected operating temperature. For example, when working at room temperature, Tm can be about 25° C. or more. In another example when operating in human cells, Tm can be 37° C. or more. In particular, Tm can be not lower than about 15° C. In the DNA:RNA duplex, deoxyribonucleotides can be replaced with phosphorothioate deoxyribonucleotides. The nucleotides flanking the DNA activation sequence in the activation segment can be unmodified ribonucleotides to keep the highest RNAase cleavage efficiency. Alternatively, flanking nucleotides can also be modified ribonucleotides, such as 2'-O-methyl ribonucleotides, 2'-Fluoro ribonucleotides, or LNA.

In other embodiments, the 3' terminus of the second segment can be connected with the protection segment, and the RNA activation sequence can be located in the protection segment near or next to the junction of the second segment and the protection segment (see exemplary embodiments shown in FIG. 3A). FIG. 3B shows a detailed view of the junction portion of the activated conformation of the signal activatable construct. In the illustration of FIG. 3B, segment (3) to (4) form a stem-loop structure with segment (4) base paring with portion (3a) in the stem and portion (3b) in the loop. The DNA activation sequence of segment 4 base-pairs with the RNA activation sequence located in segment (3) near or next to the junction of segment (2) and (3) to form a DNA:RNA duplex which serves as a suitable substrate for RNAse H.

FIG. 7D shows the products of RNAse H cleavage of the activated signal activatable construct according to the embodiment shown in FIG. 7B. A double-stranded RNA molecule comprising segment (1) and (2) is released from a remanent comprising segment (3) to (6) and the signal polynucleotide. The released double-stranded RNA molecule has a blunt end at the 3' of segment (1) and an at least 2-base single-stranded overhang at the 3' of segment (2) and therefore can be used as a siRNA or a suitable substrate for Dicer. Other exemplary embodiments can be also found in FIGS. 8 and 11.

In some embodiments, the sensor domain is configured to avoid immune activation in the cell, wherein the sensor domain forms a double strand duplex with the signal polynucleotide of no longer than about 30 bp. In other embodiments, the sensor domain is configured to induce immune activation in the cell, wherein the sensor domain forms a double strand duplex with the signal polynucleotide of longer than about 30 bp.

In some embodiments where the double-stranded duplex formed by the displacement segment and the protection segment is longer than 16 base pairs, and in particular, the exposed 3' terminus of the double-stranded duplex comprises modifications configured to block processing of Dicer.

In some embodiments, the targeting domain is configured to interfere with a target intracellular process of the cells through RNAi in presence of the signal polynucleotide. Accordingly suitable targeting domain include siRNA, microRNA and additional duplex structure suitable to be used in connection with RNA interfering.

The term "RNA interfering" or "RNAi" as used herein refers to a mechanism or pathway of living cells that controls level of gene expression that has been found in many eukaryotes, including animals. The RNAi pathway has many important roles, including but not limited to defending cells against parasitic genes such as viral and transposon genes, directing development and regulating gene expression in general. The enzyme Dicer, which is an endoribonuclease in the RNAse III family, initiates the RNAi pathyway by cleaving double-stranded RNA (dsRNA) molecules into short fragments of dsRNAs about 20-25 nucleotides in length. Dicer contains two RNase III domains and one PAZ domain; the distance between these two regions of the molecule is determined by the length and angle of the connector helix and determines the length of the siRNAs it produces. Dicer cleaves with the highest efficiency dsRNA substrates 21 bp and longer with a two-base overhang at the 3' end.

The small fragments of dsRNAs produced by Dicer are known as small interfering RNA (siRNA). The term "small interfering RNA" or "siRNA", sometimes also known as short interfering RNA or silencing RNA, refers to a class of dsRNA molecules which is typically 20-25 nucleotides in length and plays a variety of roles in biology. The most notable role of siRNA is its involvement in the RNAi pathway. In addition to its role in the RNAi pathway, siRNA also acts in RNAi-related pathways, including but not limited to several antiviral pathways and shaping chromatin structure of a genome.

Each siRNA is unwound into two single-stranded (ss) ssRNAs, namely the passenger strand and the guide strand. The passenger strand is degraded, while the guide strand is incorporated into a multiprotein complex, known as the RNA-induced silencing complex (RICS). RICS uses the incorporated ssRNA as a template for recognizing a target messenger RNA (mRNA) molecule that has complementary sequence to the ssRNA. Upon binding to the target mRNA, the catalytic component of RICS, Argonaute, is activated, which is an endonuclease that degrades the bound mRNA molecule.

Similar to siRNAs, microRNAs (miRNAs) also mediate the RNAi pathway. The term "microRNA" or "miRNA" as used herein indicates a class of short RNA molecules of about 22 nucleotides in length, which are found in most eukaryotic cells. miRNAs are generally known as post-transcriptional regulators that bind to complementary sequences on target mRNA transcripts, usually resulting in translational repression and gene silencing.

miRNAs are encoded by miRNA genes and are initially transcribed into primary miRNAs (pri-miRNA), which can be hundreds or thousands of nucleotides in length and contain from one to six miRNA precursors in hairpin loop structures. These hairpin loop structures are composed of about 70 nucleotides each, and can be further processed to become precursor-miRNAs (pre-miRNA) having a hairpin-loop structure and a two-base overhang at its 3' end.

In the cytoplasm, the pre-miRNA hairpin is cleaved by the RNase III enzyme Dicer. Dicer interacts with the 3' end of the hairpin and cuts away the loop joining the 3' and 5' arms, yielding an imperfect miRNA:miRNA duplex about 22 nucleotides in length. Overall hairpin length and loop size influence the efficiency of Dicer processing, and the imperfect nature of the miRNA:miRNA base pairing also affects cleavage. Although either strand of the duplex can potentially act as a functional miRNA, only one strand is usually incorporated into RICS where the miRNA and its mRNA target interact.

In several embodiments herein described suitable to deliver RNAai related molecule, in the inactive conformation, the 3' terminus of the second segment is protected from being processed by RNAi loading pathway enzymes (e.g. Dicer) by the presence of the sensor domain. Also, the sensor domain itself has a secondary structure such as the stem-loop structure as shown in FIG. 1, as well as chemical modifications to the nucleotides that make it incompatible with processing by RNAi loading pathway enzymes. In the inactive conformation, base-pairing of the protection segment and displacement segment prevents binding of the DNA activation sequence comprised in the activation segment from binding to the RNA activation sequence located at the junction between the second segment and the protection segment (see exemplary embodiments shown in FIGS. 1, 2A, 9(I), 10(I), 12(I), 13(I)) or in the protection segment near or next to the junction between the second segment and the protection segment (see exemplary embodiments shown in FIG. 3A). To promote construct stability and/or to prevent loading into the RISC complex, the exposed 5' end of the one or more polynucleotide of the construct can have one or more chemically modified nucleotides, while the exposed 3' end of the one or more polynucleotide of the construct can contain a modified organic group, including but not limited to, fluorescein, cytidine biphosphate, propanediol, puromycin, which prevents binding of the PAZ domain of RNAi loading pathway enzymes, such as Dicer.

In those embodiments, wherein the targeting segment is configured for interfering a target intracellular process through RNAi, the double-stranded duplex typically formed by the first segment and the second segment can have a melting temperature (Tm) of at least about 25° C. In particular, the 5' terminal nucleotide of the first segment can be base paired to the second segment. In some embodiments, double-stranded duplex formed by the first segment and the second segment are stable under conditions of the environment where delivery will be performed. In some embodiments, the RNAi targeting domain does not have overhangs, especially at the 5' terminus of the first segment. In some embodiments where the first segment has a 5' overhang, the 5' overhangs is expected to interfere under certain conditions with PAZ domain binding to the 3' terminus of the second segment upon activation. In some embodiments, the RNAi targeting domain can have a 2-nucleotide 3' overhang on the second segment to maximize RNAi efficiency. In embodiments where RNAai is performed in mammals the double-stranded duplex typically formed by the first segment and the second segment can have a melting temperature (Tm) of at least about 37° C.

In some embodiments, a double-stranded polynucleotide duplex with a 3' overhang of 2 nucleotides in length is most efficiently bound by the PAZ domain of the endonucleases enzyme Dicer (Jin-Biao Ma, et al, 2004). In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. Accordingly, the DNA:RNA duplex formed in the activated conformation according to the current disclosure is at least 5 nucleotides, and in particular 7-8 nucleotides.

Therefore, in some embodiments, the RNAse H cleavage activity produces a 2 base single-stranded overhang at the 3' of the second segment. Accordingly, in an embodiment, the RNA activation sequence is located adjacent to the junction between the second segment and the protection segment and is 2-5 nucleotides in length, wherein in the activated conformation, the DNA activation segment base pairs to the RNA activation sequence and an additional 3 consecutive ribonucleotides in the second segment, which is adjacent to the RNA activation sequence (see e.g. FIG. 2C). FIG. 2C shows the products of RNAse H cleavage of the exemplary activated conformation shown in FIG. 2B. A double-stranded RNA molecule comprising segment (1) and (2) is released from a remanent comprising segment (3) to (6) and the signal polynucleotide. The released double-stranded RNA molecule has a blunt end at the 3' of segment (1), a stem of at least 21 base pairs and an at least 2-base single-stranded overhang at the 3' of segment (2) and therefore can be used as a siRNA or a suitable substrate for Dicer.

Alternatively, in some embodiments, the RNAse H cleavage activity produces single-stranded overhang at the 3' of the second segment longer than 2 nucleotides. Reference is made to FIG. 3C. FIG. 3C shows the products of RNAse H cleavage of the exemplary activated conformation shown in FIG. 3B. A double-stranded RNA molecule comprising segment (1) and (2) and at least partially portion 3a is released from a remanent comprising at segment (4) to (6), portion (3b), at least partially portion 3a and a signal polynucleotide. The released double-stranded RNA molecule has a blunt end at the 3' of segment (1) and an at least 5-base single-stranded overhang at the 3' of portion 3a and therefore can be used as a siRNA or a suitable substrate for Dicer.

In those embodiments where the targeting domain is configured to interfere with a target intracellular process of the cells through RNAi, the first segment and the second segment are at least 16 nucleotides in length. In particular, in some embodiments, they are no short than 22 nucleotides. In particular, in some embodiments, the second segment is at least 2 nucleotides longer than the first segment. Accordingly, in some embodiment, the double-stranded duplex formed by the first segment and second segment has a 2-base single strand overhang at the 3' terminus of the second segment.

In particular, in some embodiments, the double-stranded duplex formed by the first segment and the second segment are no longer than 30 consecutive base pairs, if the duplex comprises only unmodified ribonucleotides. In other embodiments, the double-stranded duplex formed by the first segment and the second segment can be longer than 30 base pairs, if the duplex comprises mismatches and/or modified ribonucleotides. The mismatches and/or modifications are likely to prevent activation of innate immune system. Exemplary modifications to the first and the second segments include but are not limited to 2'-O-methylation, 2'-Fluoro modifications, 2'-amino modifications, and inclusion of LNA or PNA nucleotides. In particular, 2'-O-methyl, 2'Fluoro, 2'amino, LNA and PNA are expected to improve stability of the structure.

Further, in these embodiments, at least one at least one strand of the duplex is configured for interfering a target intracellular process through RNAi. In some embodiments, the at least one strand is at least partially complementary to a target gene sequence for silencing that gene through RNAi. In other embodiments, the at least one strand is at least partially complementary to a common sequence shared by multiple genes or members of a gene family. In other embodiments, the at least one strand is configured to be incorporated into a protein complex to activate the complex and/or the substrate of the complex or to initiate a cascade of activation of downstream effectors of the complex. In some embodiments, from 2 to 8 bases of the at least one strand incorporated into RISC is complementary with a target gene forming. a "seed region" usually considered particularly important for RNAi activity as will be understood by a skilled person.

According to several embodiments, the duplex formed by the first segment and second segment has a blunt end at the 3' end of the first segment (see also exemplary embodiments in FIGS. 1A, 5A, 11(I), 12(I), 13(I), 14(I)). The duplex formed by the first segment and the second segment is at least 21 bp long. In particular, the first 21 nucleotide from the 3' terminus of segment 2 or the 5' terminus of segment 1 is configured for interfering a target intracellular process through RNAi, and the $21^{st}$ and $22^{nd}$ nucleotides from the 5' terminus of the first segment and from the 3' terminus of the second segment are unmodified RNA nucleotides so as to allow efficient Dicer processing after signal activation of the signal activatable construct.

In other embodiments, the 3' terminal region of segment 1 comprises modifications to inhibit RNAi loading pathway enzyme processing from the 3' terminus of the first segment. In particular, in some embodiments, the last at least 1 base at the 3' terminal region of the first segment is a DNA modified DNA base. In particular, the last 2 nucleotides at the 3' terminal region of the first segment is a DNA modified DNA base. In other embodiments, the 3' terminal region of segment 1 is chemically modified. Exemplary modifications includes but are not limited to 3'-O-propanediol modifications, 3'-O-fluorescin modifications, 3'-puromycin modifications, 3'-inverted dT modifications, inverted Dideoxy-T modifications and the like that are identifiable by a skilled person in the art.

In some embodiments, the double-stranded duplex formed by the first segment and the second segment have additional modifications at the 3' terminus of segment 1 and/or the 5' terminus of segment 2 to further prevent processing of the inactivate construct by RNAi loading pathway enzymes, such as Dicer. In particular, in some embodiments, the duplex has a single strand overhang of at least 1 base at the 3' terminus of the first segment (see exemplary embodiments shown in FIG. 5B) or at the 5' terminus of the second segment. In some embodiments, the 3' terminus of the first segment has additional secondary structures, such as a terminal polynucleotide hairpin with 4-15 bp long stem. In some embodiments, the 3' terminus of segment 1 is connected with a synthetic polynucleotide structure, such as a DNA or RNA multi-crossover tile, a DNA or RNA origami, a DNA or RNA crystal, and other structures identifiable by a person skilled in the art.

In some embodiments the first segment comprises one or more consecutive deoxyribonucleotides at the 5' terminus complementing one or more consecutive ribonucleotide located at the 3' terminus of second segment, and the one or more consecutive ribonucleotide is adjacent to the RNA activation sequence comprised in the protection segment of the sensor domain. Reference is made to FIGS. 8, 11.

In some embodiments, the 3' terminus of the first segment is linked to the 5' terminus of the second segment via polynucleotide linker (see exemplary embodiments in FIGS. 5C, 5D, 8, 9, 10, 14, 15, and 16). In these embodiments, the duplex formed by the first segment and the second segment is at least 19 bp long. In particular, the first 21 nucleotide from the 3' terminus of segment 2 or the 5' terminus of segment 1 is configured for interfering a target intracellular process through RNAi, and the 20 and $22^{nd}$ nucleotides from the 5' terminus of the first segment and from the 3' terminus of the second segment are unmodified ribonucleotides so as to allow efficient Dicer processing after signal activation of the signal activatable construct.

In particular, in some embodiments, at least one of the first segment and the second segment comprises a sequence homologous to an endogenous microRNA sequence. More particularly, in some embodiment, the first segment and the second segment have the exact same sequence and structure as a known or predicted mammalian pre-miRNA. In some embodiments, at least one of the first segment and the second segment has the same sequence as a known or predicted mammalian miRNA. In some embodiments, the double-stranded duplex formed by the first and the second segment comprises mismatches and/or bulges configured to mimic a known or predicted mammalian miRNA (see Exemplary embodiments shown in FIG. 5D). In some embodiments at least one of the first segment and the second segment is homologous to the sequence of a known or predicted mammalian miRNA. The term "homologous" or "homology" used herein with respect to biomolecule sequences as indicates sequence similarity between at least two sequences. In particular, according to the current disclosure, a homologous sequence of a mammalian miRNA can have the same sequence located at base position 2-7 from the 5' terminus of the guide strand of the miRNA.

In some embodiments, the targeting domain is configured to deliver a cargo molecule other than a polynucleotide in the presence of the signal polynucleotide. In these embodiments, the targeting domain can also comprise a double-stranded polynucleotide duplex as part of the cargo. Reference is made to the constructs illustrated in FIG. 5B, FIG. 14, FIG. 15 and FIG. 16 which can be adapted to also include a molecule such as peptide, small molecule, aptamers and additional molecules identifiable by a killed person The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e.g. inhibition or activation of a target) or exogenous (e.g. cell signaling), which are used as a tool in molecular biology, or which are suitable as drugs in medicine. Small molecules can also have no relationship to natural biological molecules. Typically, small molecules have a molar mass lower than 1 kg·mol$^{-1}$. Exemplary small molecules include secondary metabolites (such as actinomicyn-D), certain antiviral drugs (such as amantadine and rimantadine), teratogens and carcinogens (such as phorbol 12-myristate 13-acetate), natural products (such as penicillin, morphine and paclitaxel) and additional molecules identifiable by a skilled person upon reading of the present disclosure.

The terms "peptide" and "oligopeptide" usually indicate a polypeptide with less than 50 amino acid monomers, wherein the term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived.

In an embodiment, a target domain can be attached to a sensor domain herein described with methods and approaches identifiable by a skilled person. In particular, attachment can be performed at a portion of the protection domain configured for binding the target domain (e.g. presenting a suitable functional group) and presented for binding in the sensor domain. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. The term "present" as used herein with reference to a compound or functional group indicates attachment performed to maintain the chemical reactivity of the compound or functional group as attached. Accordingly, a functional group presented on a segment, is able to perform under the appropriate conditions the one or more chemical reactions that chemically characterize the functional group. Exemplary target binding portion herein described comprise a monomer presented in the 5' terminus of the protection domain. A skilled person will be able to identify additional suitable portions, including intermediate compound or functional groups used to covalently attach the target domain with the protection domain at any suitable portion. In particular the target binding portion of the protection segment and the activation domain are typically attached of the RNA portion of the protection segment.

In some embodiments, a system for intracellular information processing and controlling of cells is described. The system comprising two or more signal activatable constructs as described for simultaneous combined or sequential use in the cells, in which the targeting domain of at least one construct of the two or more constructs is configured to release a second signal in the presence of the signal polynucleotide, and the second signal is configured to activate one or more construct of the two or more constructs.

In some embodiments, one or more signal activatable constructs and/or component thereof including sensor domains can be used in a method for RNAse H assisted signal activated molecular delivery in cells. The method comprises delivering to the cells an effective amount of one or more of the signal activatable construct described herein possibly preceded by contacting the sensor domain with a suitable targeting domain to provide the construct.

As disclosed herein, the signal activated constructs and related components herein described can be provided as a part of systems for enzyme assisted molecule delivery, including any of the deliveries described herein. The systems can be provided in the form of kits of parts. In a kit of parts, the signal activated constructs and related components and other reagents to perform enzyme-assisted delivery can be comprised in the kit independently. The signal activated constructs and related components can be included in one or more compositions, and each construct or component can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of molecule delivery can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, one or more signal activated constructs and/or related components, (e.g. sensor domain)

herein described are comprised in a composition together with a suitable vehicle. The term "vehicle" as used herein indicates any of various media acting usually as solvents, carriers, binders or diluents for signal activated constructs and related components that are comprised in the composition as an active ingredient. In particular, the composition including the signal activated constructs and related components can be used in one of the methods or systems herein described.

In some embodiments, a composition for RNAse H assisted signal activated molecular delivery in can comprise one or more of the signal activatable construct as described together with a suitable vehicle. In some embodiments, the vehicle is suitable for delivering the signal activatable construct to cells. Exemplary suitable vehicles according to the current disclosure include but are not limited to nanoparticle, such as cyclodextrin, gold nanoparticle and dendrimer; liposome and liposome analogues; conjugated aptamer; conjugated antibody; conjugated cell penetrating peptide or peptide analogue; carbon nanotubes; conjugated fatty acids and quantum dots.

In some embodiments, the signal activated constructs and related components herein described are comprised in pharmaceutical compositions together with an excipient or diluent.

The term "excipient" as used herein indicates an inactive substance used as a carrier for the active ingredients of a medication. Suitable excipients for the pharmaceutical compositions herein described include any substance that enhances the ability of the body of an individual to absorb the signal activated constructs and related components herein described or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, disclosed are pharmaceutical compositions which contain at least one signal activated constructs and related components as herein described, in combination with one or more compatible and pharmaceutically acceptable vehicles, and in particular with pharmaceutically acceptable diluents or excipients. In those pharmaceutical compositions the signal activated constructs and related components can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individual" as used herein in the context of treatment includes a single biological organism, including but not limited to, animals and in particular higher animals and in particular vertebrates such as mammals and in particular human beings.

A skilled person will be able to identify, cargo molecules to be used as active agents in the treatment and design a corresponding signal activatable construct to be administered according to the feature of the construct and the desired effect. In particular, in applications wherein signal activatable construct is desired system administration of the agent can be performed. In embodiments, where an activated construct is instead used, topical administration to the specific target cell and tissue can be performed.

Further advantages and characteristics of the present disclosure will become more apparent hereinafter from the following detailed disclosure by way or illustration only with reference to an experimental section.

EXAMPLES

The synthesized signal activatable constructs herein disclosed are further illustrated in the following examples, which are provided by way of illustration and are not intended to be limiting.

Example 1

Preparation of a Human Cell Lysate Having Endogenous Dicer Activity

A human cell lysate is prepared by the procedure as described below:

A human cell lysate is prepared by the procedure as described. Cells were grown in a 10 cm dish. Plates were prechilled on ice in a cold room. Media were removed and the plates were washed twice with cold PBS. Excess PBS was removed. The plates were kept on ice throughout the process.

½ volume of ice-cold LSLB+P buffer (see below) was then added to the plates; the cells were scraped up and transferred to a microfuge tube. The step was repeated with ½ volume of buffer and ½ volume of buffer was add to the first ½ volume. Cells were scraped from plates and collected in a 1.5 ml microfuge tube. Samples were let sit on ice for 30 minutes. 1 and 3 samples were freezed in dry ice (samples 2 and 4 were left on ice, inverting occasionally). Samples 1 and 3 were rapidly thawed in cool water bath in cold room at circa 12° C.

All samples were then run through a series of (chilled) needles of decreasing size (22, 25 & 27), and resistance was felt with 25 and 27 gauges. The step was performed 4× for each gauge to insure cells are thoroughly lysed and separate syringe/needles was used for each sample. Lysates were spun at 4° C. in a microfuge at 12,000 rpm for 7 minutes to pellet cell debris. Supernatant/lysate aliquots were removed to new tubes on ice, frozen on dry ice, and then stored at −80° C.

Figure 17:
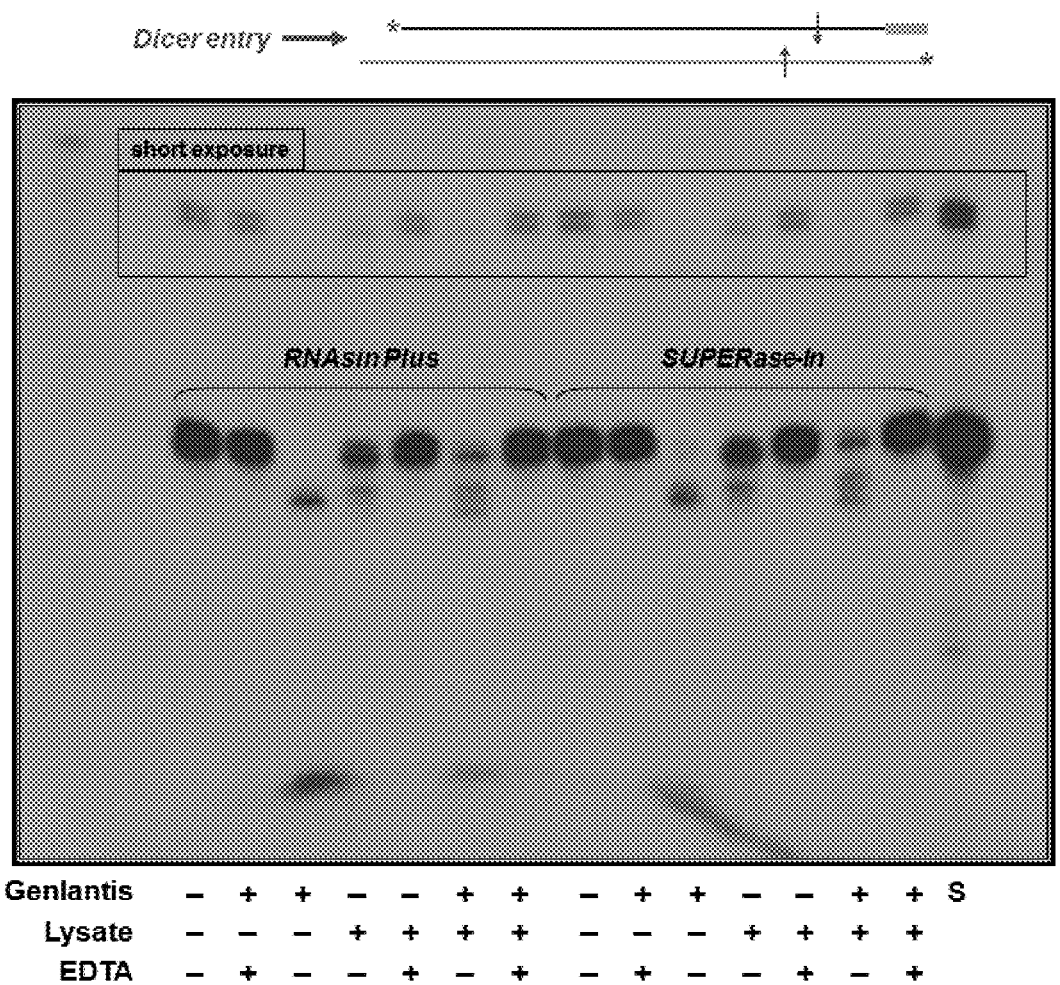
FIG. 17 shows the cleavage of a synthesized human Dicer substrate by a human cell lysate preparation. Top shows double-stranded duplex of polynucleotides labeled at their 5' termini (marked by asterisk) and having a 3' overhang suitable for Dicer binding. Bottom shows a polyacrylamide gel showing radioactively labeled polynucleotides after electrophoresis. The polynucleotides are visualized by 5' radioactive labeling by $^{32}$P.

A set of experiments were performed to test endogenous Dicer activity of the prepared human cell lysate using a known human Dicer substrate (FIG. 17 top). Both 5' terminus ends of the substrate are labeled with radioactive probe (e.g. $^{32}$p-32). The substrate is incubated with the cell lysate with or without EDTA and with or without a recombinant Dicer enzyme (a product of Genlantis®). EDTA is a divalent cation chelator that is able to remove $Mg^{2+}$ ions from the active site of endonucleases, including Dicer, thereby inhibiting the endonuclease activity. To prevent spurious cleavage of the label substrate by endogenous endonucleases activities of the human cell lysate, an RNAse inhibitor (RNAsin Plus, a product of Promega®, or SUPERase-IN, a product of Ambion®) is also included in the incubation.

The incubation was performed at 37° C. for 2 hours. Then the incubation products were extracted using phenol/chloroform, and loaded onto a denaturing polyacrylamide gel for electrophoresis. After electrophoresis, the polynucleotides were transferred to a nitrocellulose membrane and were visualized by the 5' radioactive label (see FIG. 17 bottom).

As shown in FIG. 17, a RNA ladder with strands at 10 nucleotide length increments was shown in lane 15 No significant difference was observed for the incubations with added RNAsin plus (lanes 1-7) as compared to the ones with added SUPERase-IN (lanes 8-14). The patterns shown in lanes 3, 6, 10 and 13 indicate cleavage of the substrate by the recombinant Dicer enzyme; The patterns shown in lanes 4, 6, 11 and 13 indicate cleavage of the substrate by the endogenous Dicer activity. In particular, lane 3 and 10 shows cleavage by the recombinant Dicer enzyme alone, which produces cleaved polynucleotides of estimated 21 and 22 nt, respectively; Lane 4 and 11 shows cleavage by the endogenous Dicer activity alone, which produces cleaved polynucleotides of 20, 21, and 22 nt, respectively; Lane 6 and 13 shows cleavage by both enzyme activities. The patterns shown in lanes 2, 7, 9 and 14 indicate inhibition of both enzyme activities by EDTA, as no cleaved polynucleotides of small sizes was observed. Negative control groups are shown in lanes 1 and 8. This result indicates that the human cell lysate preparation has normal endogenous Dicer enzymatic activity.

Example 2

Signal Activation of the Signal Activated Construct Through Endogenous RNAse H Activity A set of experiments were performed to test signal activation and RNAse H cleavage of a signal activated construct using the human cell lysate described in Example 1. The signal activated construct used in this set of experiments has the structure as shown in FIG. 18 C and D (implementation 2). In particular, as shown in FIG. 18 D left penal, the inactive conformation (SEQ ID NO: 11 and SEQ ID NO: 12) has a double strand duplex of 25 base pairs in the targeting domain, which has one blunt end and a 2 base 3' overhang at the opposite end, which links to the sensor domain. The sensor domain has a 14 base pair stem, a 9 base DNA loop and an 8 base toehold domain arranged as a 3' overhang of the sensor domain. As shown FIG. 18 D right panel, upon binding to a synthetic signal polypeptide (SEQ ID NO: 17), the construct transform to the activated conformation having an 8 base pair DNA:RNA duplex, which serves as a suitable substrate for RNAse H.

The signal activated construct was labeled with a radioactive label ($^{32}$P) at the 5' terminus of one of its two strands and was incubated with the human cell lysate with or without the synthetic signal polynucleotide and with or without EDTA. EDTA is a divalent cation chelator that is able to remove $Mg^{2+}$ ions from the active site of Dicer and other endonucleases, thereby inhibiting their activity. In this set of experiments, the addition of EDTA is used as a negative control for Dicer activity.

The incubation was performed at 37° C. for 1 or 2 hour(s). Then the incubation products were extracted using phenol/chloroform, and loaded onto a denaturing polyacrylamide gel for electrophoresis. After electrophoresis, the polynucleotides were transferred to a nitrocellulose membrane and were visualized by the 5' radioactive $^{32}$P label.

Figure 19:
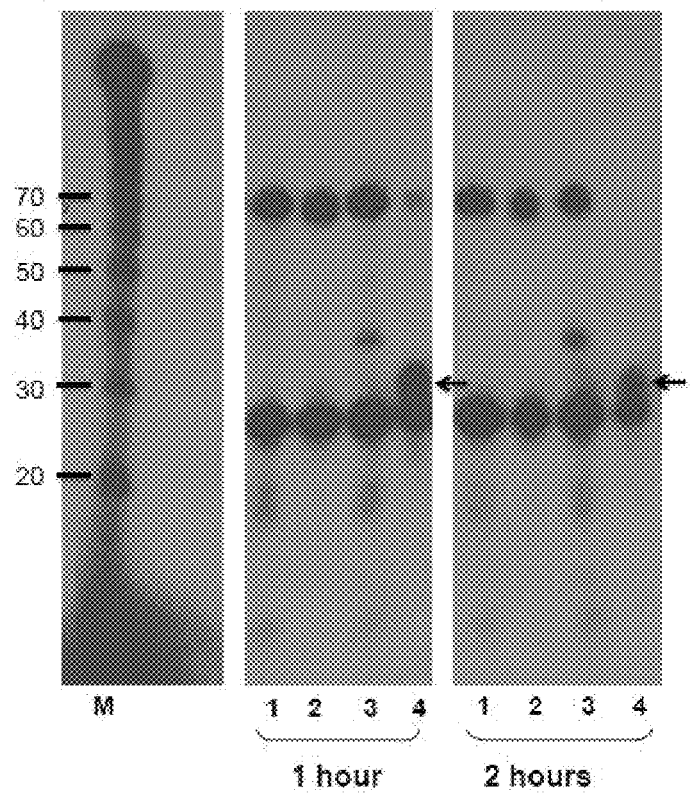
FIG. 19 shows signal activation and RNAse H cleavage of the signal activated construct according to an exemplary embodiment (Implementation 2) herein described. The figure shows a polyacrylamide gel showing radioactively labeled polynucleotides after electrophoresis. The polynucleotides are visualized by 5' radioactive labeling by $^{32}$P. Arrow indicates signal polynucleotide dependent RNAse H cleavage product.

As shown in FIG. 19 the signal activated construct is rapidly activated by endogenous RNAse H, and the RNAse H cleaved products are stable in the human cell lysate (lane 4 1 hr and 2 hr). Also, the RNAse H activity is inhibited by EDTA (lane 3 1 hr and 2 hr).

Example 3

Signal Activation of the Signal Activated Construct and RNA Interfering Through Endogenous RNAse H and Dicer Activity A set of experiments were performed to test signal activation and subsequent RNAi activity of the signal activated construct using the human cell lysate described in Example 1. The signal activated construct used in this set of experiments has the structure as shown in FIG. 18A and B (Implementation 1). Briefly, as shown in FIG. 18B left penal, the inactive conformation (SEQ ID NO: 1 and SEQ ID NO: 3) has a double strand duplex of 25 base pairs in the targeting domain, which has one blunt end and a 2 base 3' overhang at the opposite end, which links to the sensor domain. The sensor domain has a 14 base pair stem, a 15 base loop comprising 8 deoxylnucleotides and an 8 base toehold domain arranged as a 3' overhang of the sensor domain. As shown in FIG. 18B right penal, upon binding to a synthetic signal polypeptide (SEQ ID NO: 9), the construct transform to the activated conformation having an 8 base pair DNA:RNA duplex, which serves as a suitable substrate for RNAse H.

The signal activated construct was labeled with a radioactive label ($^{32}$P) at the 5' terminus of one of its two strands and was incubated with the human cell lysate with or without the synthetic signal polynucleotide and with or without EDTA. EDTA is a divalent cation chelator that is able to remove $Mg^{2+}$ ions from the active site of Dicer and other endonucleases, thereby inhibiting their activity. In this set of experiments, the addition of EDTA is used as a negative control for Dicer activity.

The signal activated construct was labeled with a radioactive label (P-32) at the 5' terminus of one of its two strands and was incubated with the human cell lysate with or without the synthetic signal polynucleotide and with or without EDTA. EDTA is a divalent cation chelator that is able to remove $Mg^{2+}$ ions from the active site of Dicer and other endonucleases, thereby inhibiting their activity. In this set of experiments, the addition of EDTA is used as a negative control for Dicer activity.

The incubation was performed at 37° C. for 1 or 2 hours. Then the incubation products were extracted using phenol/chloroform, and loaded onto a denaturing polyacrylamide gel for electrophoresis. After electrophoresis, the polynucleotides were transferred to a nitrocellulose membrane and were visualized by the 5' radioactive P-32 label or Northern blot using P-32 labeled complementary DNA probes.

The result is shown in FIGS. 20 to 26. Note that in all cases, the complete signal activated construct that comprises both strands is used for the incubation. In each case, only one of the two strands was radioactively labeled, so as to tract the behavior of the particular labeled strand in the cell lysate. As shown in FIG. 18, the 25 nucleotide shorter strand will be referred to as the "short strand", and the 72 nucleotide longer strand will be referred to as the "long strand".

Figure 20:
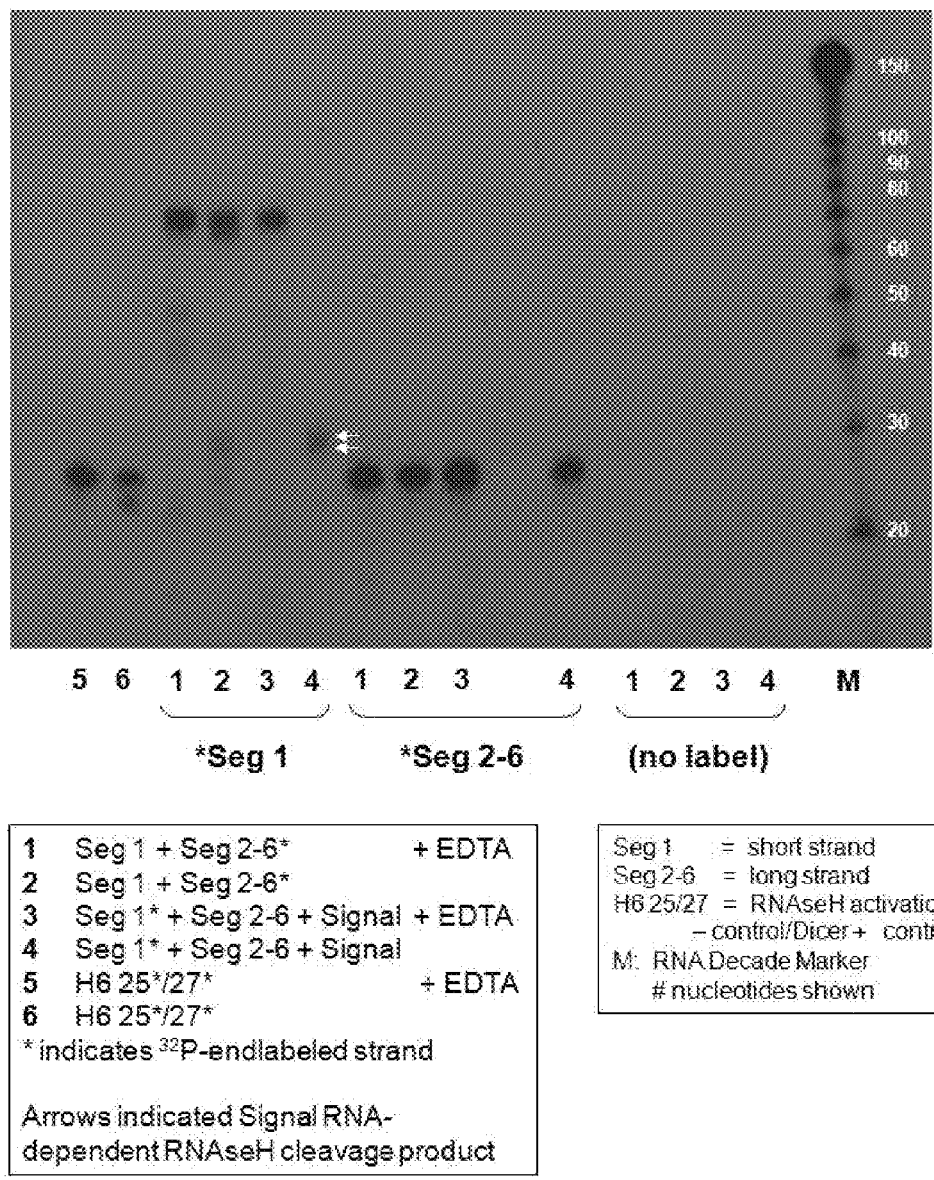
FIG. 20 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling by $^{32}$P. Arrow indicates signal polynucleotide dependent RNAse H cleavage product.

As shown in FIG. 20, a RNA ladder with strands at 10 nucleotide length increments was shown in lane M. Lanes 5 and 6 show processing of H6 25/27 mer Dicer substrate siRNA by the cell lysate used in the experiment. Compared with lane 5 (a negative control), lane 6 shows a clear Dicer cleavage product of about 22 nt, demonstrating that Dicer is active in the cell lysate, which is consistent with the Data shown in FIG. 19. As shown in Seg 1 lanes 1 to 4, the 72 nucleotide long strand of the signal activated construct is labeled at the 5' terminus, which shows up at around 70 nucleotide position on the membrane as expected. As shown in Seg 1 lanes 3 and 4, in the absence of the signal polynucleotide, this strand is not cleavage into short sequences. Note that, the additional bands visible between the 40-50 nucleotide positions are resulted from spurious degradation of the long strand during 5' labeling with $^{32}$P and irrelevant to the results. In the lysate, these spuriously cleaved products adopt a constitutively active conformation that is processed by RNAse H into about 30 nucleotide long products (lane 4). As shown in Seg 1 lanes 3 and 4, the signal activated construct is annealed to and activated by the signal polypeptide, which results in processing by RNAse h of the long strand into the about 30 nucleotide long sequences as shown in seg 1 lane 4.

As shown in Seg 2-6 lanes 1 to 4, the 25 nucleotide short strand of the signal activated construct is labeled at the 5' terminus. The stability of the short strand as shown in Seg 2-6 lanes 1 to 4 illustrate that the construct is highly resistant to Dicer processing in human cell lysate. The lack of Dice processor activity as shown in lane Seg 2-6 lanes 4 is likely due to inefficient Dicer processing of the RNAse H liberated RNAi targeting domain, which has a 6 nucleotide long 3' overhang.

Figure 21:
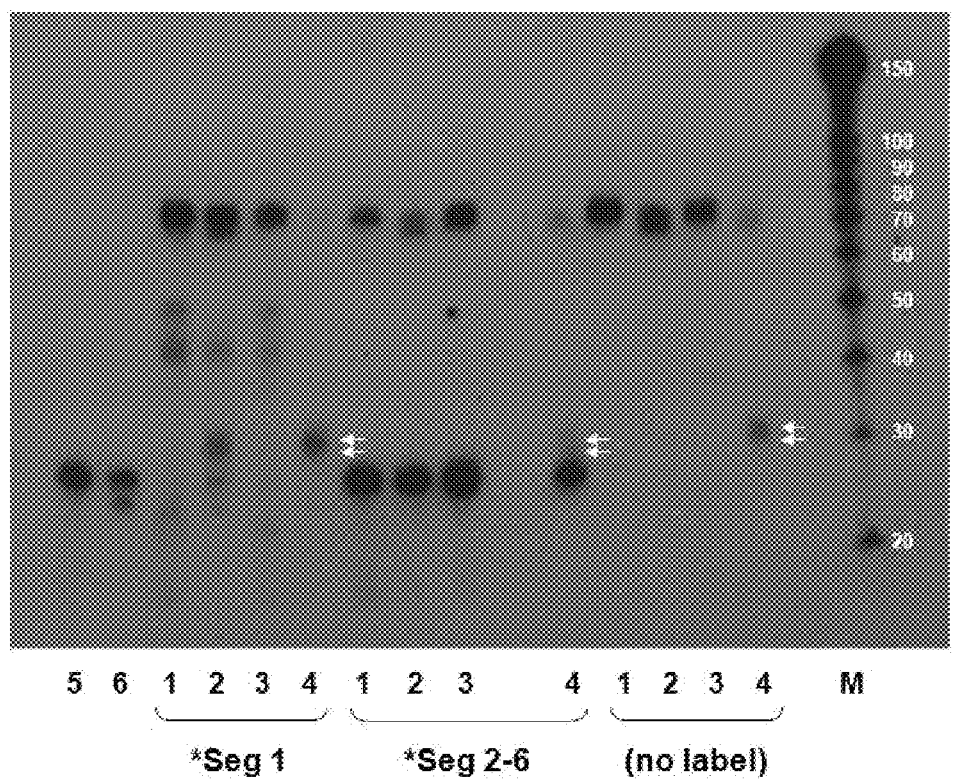
FIG. 21 shows RNAse H cleavage and Dicer processing of a signal activated construct according to an exemplary embodiment (Implementation 2) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.

As shown in FIG. 21 and FIG. 22, the membrane is blotted with a 5' radioactively labeled DNA strand complementary to the long strand. Unlabeled sequences as in lanes 1 to 4 (no label) are thus visualized. In lanes 1 to 4 (no label), the absence of signals at the two positions between 40 and 50 nucleotide further indicates that the signals seen at the corresponding positions of lane 3 are spurious products generated during the labeling process. Compared with lane 10, the signal activated construct in lane 1 (no label) shows minimal degradation, demonstrating that the construct is highly resistant to endogenous Dicer activity. In the presence of the signal polynucleotide (lanes 3 and 4, no label), the long strand is efficiently processed by RNAse H into the desired product at the about 30 nucleotide position. FIG. 22 shows the no label lanes 1-4 as shown in FIG. 21.

Figure 23:
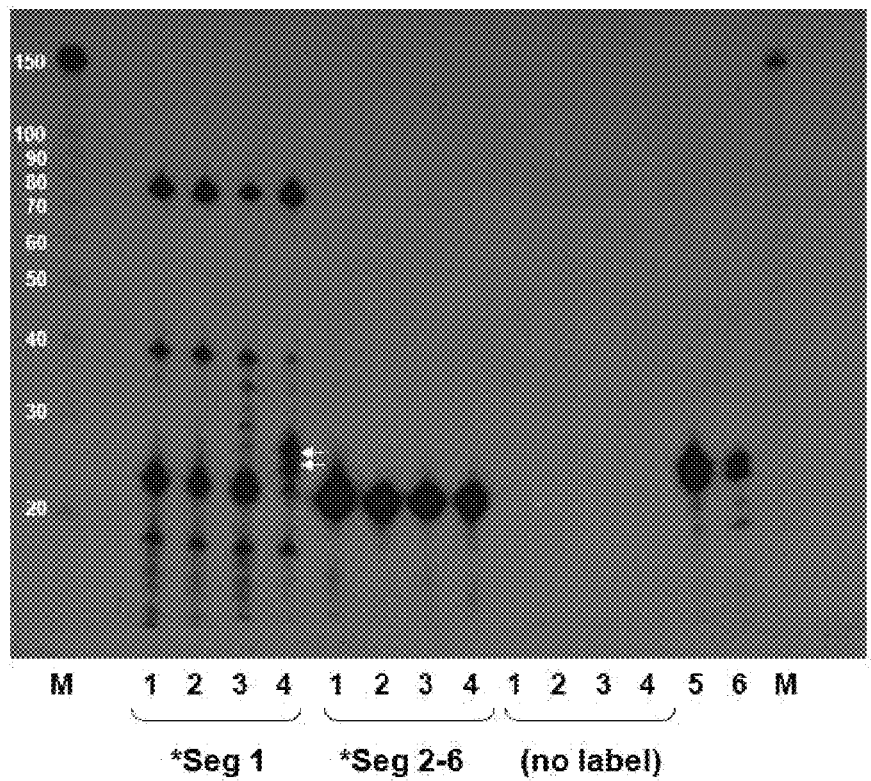
FIG. 23 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.
Figure 24:
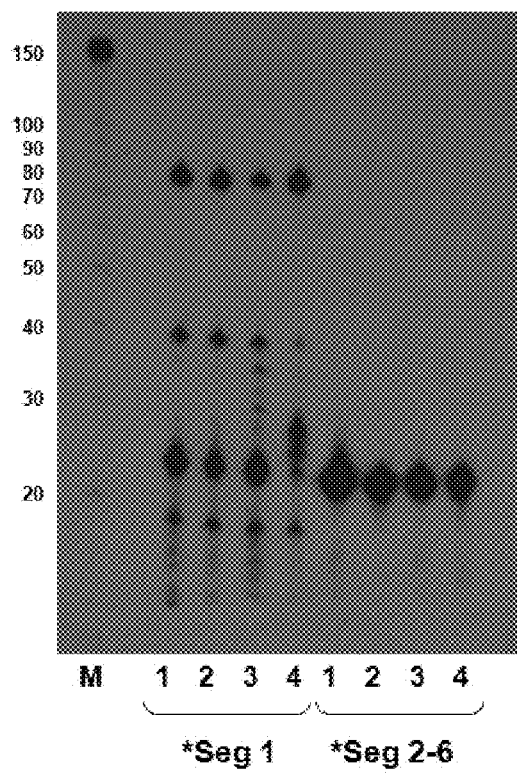
FIG. 24 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.

FIG. 23 shows there was very little observable RNAse H processing of the construct in the absence of the signal polynucleotide. When the construct was annealed with a signal polynucleotide, three distinctive bands appeared indicating cleavage at approximate positions (lane 4, Seg 1, arrows), which is consistent with the results as shown in FIGS. 20-22. FIG. 24 shows the portion of FIG. 23 without the no label lanes 1-4.

Figure 25:
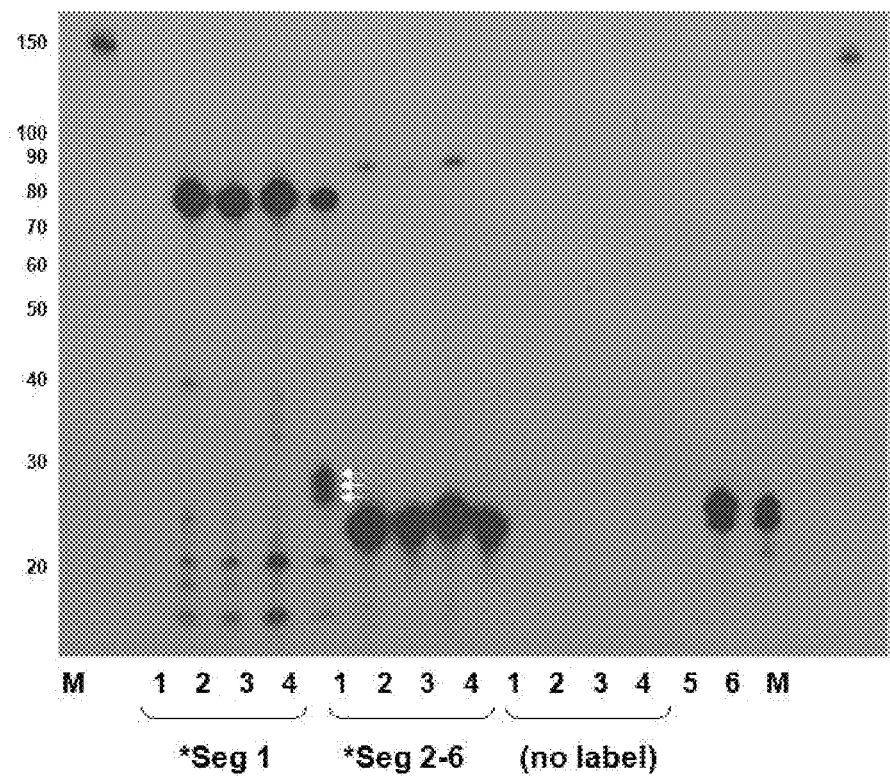
FIG. 25 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.
Figure 26:
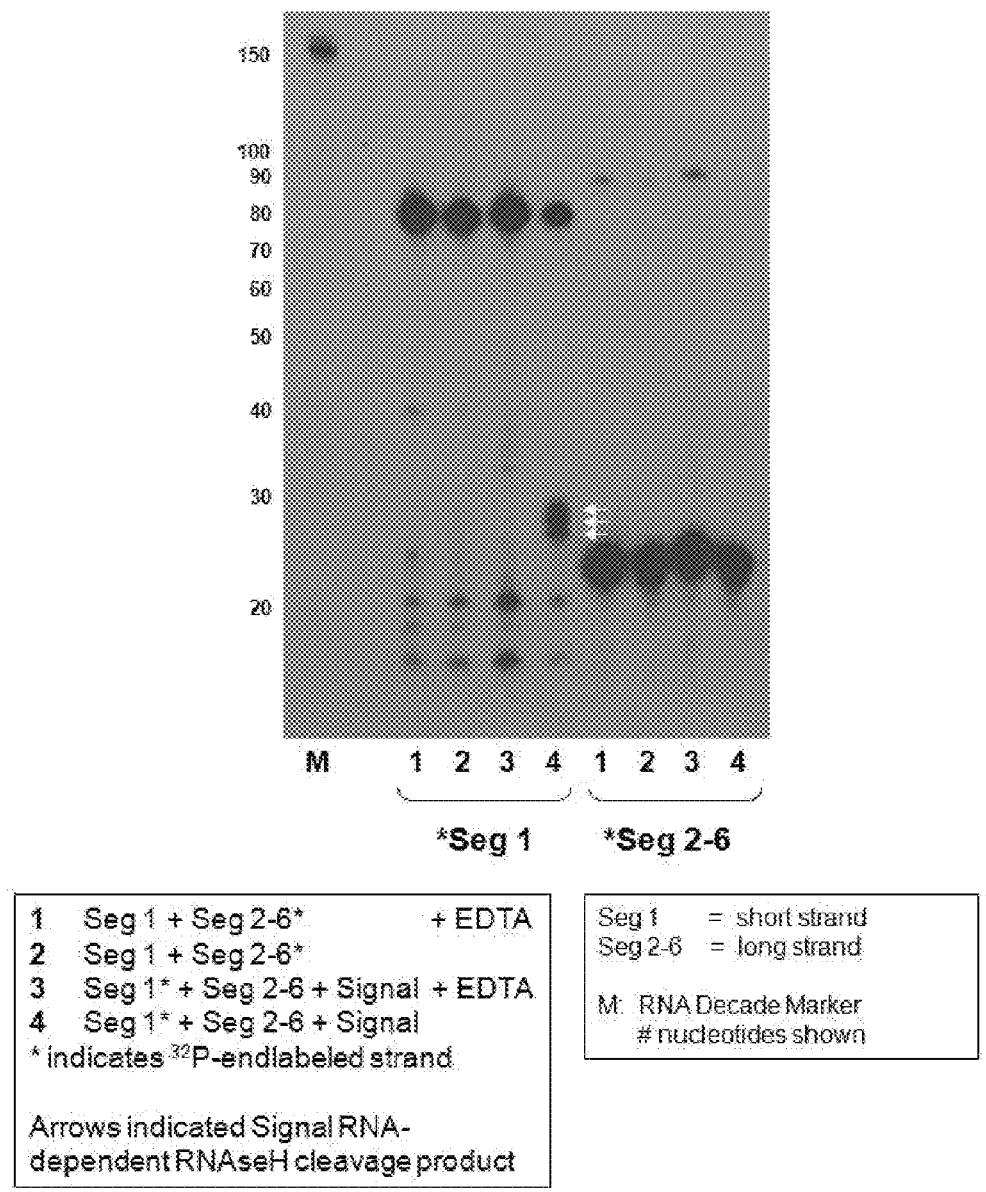
FIG. 26 shows RNAse H cleavage and Dicer processing of a signal activated construct according to an exemplary embodiment (Implementation 1) herein described. The figure shows a polyacrylamide gel showing radioactively labeled polynucleotides after electrophoresis. The polynucleotides are visualized by 5' radioactive labeling and by northern blotting using 5' radioactively labeled complementary DNA sequences by $^{32}$P. Arrow indicates signal polynucleotide dependent RNAse H cleavage product.

FIGS. 25 and 26 shows the above experiment after 2 hour incubation and lower exposure time. Results indicate that the construct was likely processed at the positions indicated by the arrows in the other figure only in the presence of the signal polynucleotide.

Taken together, these results indicate that the signal activated construct is rapidly activated by endogenous RNAse H when base-paired with the signal polynucleotide. However, in the absence of the signal polynucleotide, the signal activated construct is resistant to Dicer processing and inert to processing by RNAse H.

Example 4

Testing and Measuring of the Melting Temperature (Tm) of the Construct-Activation Junction Exemplary experimental procedures for testing/measuring the melting temperature of the three-way activation formed between the activation segment and portions of the first segment, the second segment and the protection segment are described below:

Applicants first synthesized oligonucleotides comprising sequences of designed for the first segment, second segment, protection segment and activation segment respectively using standard methods for oligonucleotide synthesis well establish in the art. Then the synthesized oligonucleotides were then purified based on their expected lengths. The purified oligonucleotides were mixed together in an RNAase free buffer containing PBS. To allow proper annealing of the oligonucleotides, the mixture was heated to about 90° C. for 1 minutes and then cooled to a desired melting temperature of about 15° C. at the rate of 1° C. every 10 seconds. After annealing, RNAse H was added to the buffer and incubated according to manufacturer's instructions to allow cleavage of the construct by RNAse H. The cleavage products were then loaded onto a denaturing polyacrylamide gel (SDS-PAGE) following by electrophoresis to examine whether a proper DNA: RNA duplex of at least 5 consecutive base pairs have formed during annealing and whether the construct was cleaved at the expected RNAse H cleavage site.

To examine whether an activation junction formed among the segments (e.g. a three-way activation junction) is formed properly, Applicants attached pairs of fluorophore/quencher to nucleotides that are expected to form base pairs between opposing strands when the activation junction is properly formed, and examined whether significant quenching of the fluorescence signal can be observed at the minimum melting temperature using fluorescent microcopy. Additionally, the fluorophore/quencher pairs can be attached to pairs of neighboring nucleotides near the junction. Alternatively, in the above experiments, the fluorophore/quencher pairs can be replaced by pairs FRET acceptor/donor fluorophores, and examine significant FRET can be observed at the minimum melting temperature.

As a complimentary approach, Applicants used a standard set of procedures known to the art to establish the secondary structure of the construct.

First, Applicants used single stranded RNA endonucleases to digest the construct, and examined whether RNA portions of the segments that are expected to form double strands were protected from the cleavage by the endonuclease by formation of proper secondary structures.

Second, Applicants used single stranded DNA endonucleases to digest the construct, and examine whether the construct is protected from the cleavage by formation of the secondary structure of the DNA:RNA duplex.

Third, Applicants tested whether the expected duplex regions of the junction is protected from RNA modifying and RNA cleaving chemical probes using 5' or 3' radionucleotide labeling or primer extension analysis.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

The above described experiments can also be performed according to commonly used experimental protocols and procedures, such as the one described in Keril J. Blight et al., Journal Of Virology, October 1997, vol 71, p. 7345-7352 herein incorporated by reference in its entirety.

Example 5

Testing and Measuring of the Melting Temperature (Tm) of the Construct-Protection Stem Exemplary experimental procedures for testing/measuring the melting temperature (Tm) of the double-stranded duplex formed by the protection segment and the displacement segment are described below:

Applicants first synthesized oligonucleotides comprising sequences of designed for the first segment, second segment, protection segment, activation segment, displacement segment and toehold segment respectively using standard methods for oligonucleotide synthesis well establish in the art. Then an internal fluorophore was attached to the 3' end of the displacement segment, and a quencher was attached to the 5' end of the protection segment opposing the base carrying the fluorophore. Alternative, the quencher can be attached to the 3' end of the displacement segment, while the internal fluorophore was attached to the 5' end of the protection segment opposing the base carrying the fluorophore. Also, a FRET donor/acceptor fluorophore pairs can be used instead of the fluorophore/quencher pair.

Then the oligonucleotides were purified based on their expected lengths and are mixed together in an RNAse free buffer containing PBS. To allow proper annealing of the oligonucleotides, the mixture was heated to about 90° C. for 1 minutes and then cooled to a desired melting temperature of about 25° C. at the rate of 1° C. every 10 seconds. During the annealing, the fluorescence signal was observed using a spectrolfuorometer to examine whether a proper double-stranded duplex is formed between the protection segment and the displacement segment. At the melting temperature of 25° C., the fluorescence signal was quenched (if a FRET pair was used instead of the fluorophore/quencher pair, significant FRET signal between the FRET pairs is expected to be observed), which indicated that a double-stranded duplex has been formed properly between the protection segment and the displacement segment.

In addition, Applicants used the standard panel of enzymatic digest and chemical probe tests to further examine the melting temperature of the construct. Applicants used single strand endonuclease to digest the construct at or below the expected melting temperature (e.g. 25° C.) to examine whether the double-stranded portion of the displacement segment and the protection segment was protected from the endonuclease cleavage.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

Example 6

Testing and Measuring of the Strand Displacement of the Construct

Exemplary experimental procedures for testing and measuring the strand displacement of the construct are described below:

Applicants first synthesized oligonucleotides comprising sequences of designed for the protection segment, activation segment, displacement segment and toehold segment (sensor domain) using standard methods for oligonucleotide synthesis well establish in the art. Then an internal fluorophore was attached to the terminus of the displacement segment that is further away from the toehold segment. A quencher was attached to the terminus of the protection segment that is further away from the toehold segment. Alternative, the internal fluorophore can be attached to the terminus of the protection segment that is further away from the toehold segment, while a quencher was attached to the terminus of the displacement segment that is further away from the toehold segment. Also, a FRET donor/acceptor fluorophore pairs can be used instead of the fluorophore/quencher pair. Also synthesized was a corresponding signal polynucleotide designed for the sensor domain described above.

Then the synthesized oligonucleotides were purified based on their expected lengths and were incubated with an equal amount of the signal polynucleotide under the operating condition (e.g. 1×PBS buffer) at the expected operating temperature (e.g. 37° C.).

The change in the fluorescent signal during the process of strand displacement was monitored and recorded using a spectrofluorometer. The recorded signal was then plotted as a function of time and the kinetic rate of the displacement reaction was determined from the plot.

To examine whether the attachment of the fluorophor/quencher introduces artifacts to the displacement kinetics and whether the entire protection segment is displaced during the process, the fluorophore/quencher pair was then attached to a different pair of nucleotides selected respectively from the protection segment and the displacement segment at positions closer to the toehold segment, and the above procedures were repeated.

Example 7

Process of Designing, Synthesis and Testing the Activity of a Signal Activated Construct Exemplary processes are described below for the designing, synthesis and testing the activity of a signal activated construct, which comprise a targeting domain configured for interfering a target intracellular process through RNAi.

To design a construct, Applicants started with the analysis of a RNA sequence that was to be targeted (interference) by RNAi, such as a target mRNA or a set of target mRNAs. According to the RNA sequence to be targeted, applicants selected the sequences for the targeting domain of the construct that were known in the art.

For example, in one set of experiments, applicants used the Dicer substrate 25/27 mers duplex of the exemplary implementations 1 or 2. In another set of experiments, applicants used a miRNA which has a similar sequence to the target mRNA(s) (see *Molecular Therapy* (2010) 18 4, 796-802. doi:10.1038/mt. 2009.321, RNA (2010), 16:1275-1284). Alternatively, a short hairpin RNA or a siRNA of known sequences can also be selected for the targeting domain or the construct.

Applicants chose a 3' terminus of the selected targeting domain to connect to the sensor domain and then blocked all other termini with 3' fluorescein. Alternatively, the termini can also be blocked by introducing one or more deoxyribonucleotides at the terminal positions.

Applicants then designed a minimum length for the signal polynucleotide based on the organism or types of cells that the construct was used. The signal sequence was designed long enough so that there are very few spurious matches to possible RNA transcripts from the organism's genome. In particular, the signal sequence was designed to comprise at least a difference of 4 nucleotides between the signal sequence and its nearest homologous sequence. For using in human cells, the signal polynucleotide was designed to have a minimum length of about 14 nucleotides. Further, the signal polynucleotide was designed to have at least 4 nucleotides that complementarily bind to the toehold segment. In total, the signal nucleotide designed for the use in human cells was about 18 nucleotides in length.

Then, Applicants designed a construct with a toehold segment arranged at the 3' terminus of the displacement segment. For a given signal polynucleotide of a length (n), with n≥18 nucleotides, Applicants examined all possible contiguous subsequences of length 18, and got n−18+1 possible sequences. For each possible sequence, Applicants took the last 14 base at the 3' end of each sequence and designated it as the protection segment, and took the fully complement sequence of the 4 bases at the 5' end of the possible sequence and designated it as the toehold segment. Applicants took the fully complementary sequence of the protection segment as the displacement segment.

After that, Applicants chose the position of the RNAse H cleavage of the construct. Applicants refer to FIG. 18A. In order to have a high efficiency for Dicer processing of the targeting domain, Applicants designed the construct so that the RNAse H cleavage produces a 2-base overhang (2c) at the 3' terminus of the targeting domain. In order to have the construct forming the cleavage position correctly, Applicants made segment 4b the exact complement of the two bases in 2c and the 3 bases in the targeting domain to the 5' of 2c, and then added two bases complementary to the two bases in the protection segment directly to the 3' of the second segment to produce a 7-base segment 4b. This is because RNAse H cleaves a substrate of 7 base pair DNA: RNA duplex with higher efficiency.

After designing the 7 nucleotides (4b), applicants designed additional nucleotides flanking 4b to stabilize the construct in the activated conformation. In particular, applicants placed additional ribonucleotides to the 5' of 4b, which are complementary to the protection segment. After the signal polynucleotide displaces the protection segment, these nucleotides in 4b will bind to the protection segment to initiate the binding segment 4b into the duplex formed by 1a and 2b. Applicants also extended the 3' of 4b by a single deoxyribonucleotide complementary to the second segment to stabilize the RNA/DNA duplex. Applicants then added 4 ribonucleotides (4d) to the 3' of 4b which are complementary to 1a, in order to stabilize the displacement of 1a by 4b via the formation of 4 extra base pairs to form a 3-way activation junction.

At this stage all segments in the sensor domain (i.e. the protection segment, displacement segment, activation segment and the toehold segment) have been specified. Using the above algorithm, Applicants designed the sensor domains for the every possible 18-nucleotides possible sequence of a chosen signal polynucleotide. Then Applicants examined each candidate design by running the sequences through an RNA secondary structure calculation code to examine the predictions for secondary structure conformation and stability. Based on the result, applicants chose one or more candidate designs with the best stability, the least complicated secondary structure in the terminal loop formed by the activation segment, and the best conformity to the target shape (e.g. a 14 base pair duplex formed by the protection segment and the displacement segment, a 4-nucleotide single stranded 3' toehold segment 6), and added chemical modifications to regulate base pair stability.

In particular, for increased stability, Applicants applied blocking chemical modification such as a fluorescein, phosphorothioate DNA bases, or cytidine bisphosphate to the 3' terminus of the toehold segment. Additionally, for increased stability, all single stranded segments (in the inactive conformation) of the sensor can be chemically protected. In particular, ribonucleotides can be protected by 2'-O-Methyl or 2'-F modifications and deoxyribonucleotides can be protected by phosphorothioate backbone. In addition, for energetic stability, the displacement segment can be made completely with 2'-O-methyl nucleotides.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the paper copy of the sequence listing submitted herewith and the corresponding computer readable form are both incorporated herein by reference in their entireties.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

Wu, H. et al., "Properties of cloned and expressed human RNase H1", The Journal of Biological Chemistry, Vol. 274, pp. 28270 (1999).

Zamaratski, E. et al., "A critical survey of the structure function of the antisense oligo/RNA heteroduplex as substrate for RNase H", Journal of Biochemical and Biophysical Methods, Vol. 48, pp. 189 (2001).

Cazenave, C. et al., "Characterization and subcellular localization of ribonuclease H activities from Xenopus laevis oocytes", The Journal of biological chemistry, Vol. 269, pp. 25185 (1994).

Nowotny, M. et al., "Crystal structures of RNase H bound to an RNA/DNA hybrid: substrate specificity and metal-dependent catalysis", Cell, Vol. 121, pp. 1005 (2005).

Song, J. J. et al., "The crystal structure of the Argonaute2 PAZ domain reveals an RNA binding motif in RNAi effector complexes", Nature Structural Biology, Vol. 10, pp. 1026 (2003).

Ma, J. B. et al., "Structural basis for overhang-specific small interfering RNA recognition by the PAZ domain", Nature, Vol. 429, pp. 318 (2004).

Yan, K. S. et al., "Structure and conserved RNA binding of the PAZ domain", Nature, Vol. 426, pp. 468 (2003).

Lingel, A. et al., "Structure and nucleic-acid binding of the Drosophila Argonaute 2 PAZ Domain", Nature, Vol. 426, pp. 465 (2003).

Behlke, M. A. et al., "Chemical modification of siRNAs for in vivo use", Oligonucleotides, Vol. 18, pp. 305 (2008).

Rose, S. D. et al., "Functional polarity is introduced by Dicer processing of short substrate RNAs", Nucleic Acids Research, Vol. 33, pp. 4140 (2005).

Tomari, Y., et al., "A Protein Sensor for siRNA Asymmetry", Science, Vol. 306, pp. 1377, (2004).

Susan M. Freier and Karl-Heinz Altman, The ups and downs of nucleic acid duplex stability: structure-stability studies on chemically-modified DNA:RNA duplexes, Nucleic Acids Research, 1997, Vol. 25, No. 22 4429-4443

Nucleic Acids Research, 1998, Vol. 26, No. 9, 2224-2229

Nucleic Acids Research, 2005, Vol. 33, No. 16, 5082-5093

564-574 Nucleic Acids Research, 2006, Vol. 34, No. 2

Sequence-specific recognition of double helical RNA and RNA.DNA by triple helix formation, PNAS May 1, 1993 vol. 90 no. 9 3806-3810

Burge S, Parkinson G N, Hazel P, Todd A K, Neidle S (2006). "Quadruplex DNA: sequence, topology and structure". NAR 34 (19): 5402-5415. doi:10.1093/nar/gk1655

J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. J Comput Chem, 32, 170-173, 2011.

R. M. Dirks, J. S. Bois, J. M. Schaeffer, E. Winfree, and N. A. Pierce. (2007) Thermodynamic analysis of interacting nucleic acid strands. SIAM Rev, 49, 65-88.

R. M. Dirks and N. A. Pierce. (2003) A partition function algorithm for nucleic acid secondary structure including pseudoknots. J Comput Chem, 24, 1664-1677.

R. M. Dirks and N. A. Pierce. (2004) An algorithm for computing nucleic acid base-pairing probabilities including pseudoknots. J Comput Chem, 25, 1295-1304.

J. N. Zadeh, B. R. Wolfe, N. A. Pierce. Nucleic acid sequence design via efficient ensemble defect optimization. J Comput Chem, 32, 439-452, 2011.

M. Zuker. Mfold web server for nucleic acid folding and hybridization prediction. Nucleic Acids Res. 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major. RNAML: A standard syntax for exchanging RNA information. RNA 8 (6), 707-717, 2002.

M. Zuker & A. B. Jacobson. Using Reliability Information to Annotate RNA Secondary Structures. RNA 4, 669-679, 1998. [Abstract][Preprint] Note: Explains color annotation of secondary structure.

N. R. Markham & M. Zuker. UNAFold: Software for Nucleic Acid Folding and Hybridization. In Data, Sequence Analysis, and Evolution, J. Keith, ed., Bioinformatics: Volume 2, Chapter 1, pp 3-31, Humana Press Inc., 2008.

M. Zuker, D. H. Mathews & D. H. Turner. Algorithms and Thermodynamics for RNA Secondary Structure Prediction: A Practical Guide In RNA Biochemistry and Biotechnology, 11-43, J. Barciszewski and B. F. C. Clark, eds., NATO ASI Series, Kluwer Academic Publishers, Dordrecht, NL, 1999.

M. Zuker. Prediction of RNA Secondary Structure by Energy Minimization. In Computer Analysis of Sequence Data A. M. Griffin and H. G. Griffin eds. Methods in Molecular Biology, Humana Press Inc., 267-294, 1994.

J. A. Jaeger, D. H. Turner & M. Zuker. Predicting Optimal and Suboptimal Secondary Structure for RNA. In Molecular Evolution: Computer Analysis of Protein and Nucleic Acid Sequences, R. F. Doolittle ed. Methods in Enzymology 183, 281-306, 1990.

M. Zuker. On Finding All Suboptimal Foldings of an RNA Molecule. Science 244, 48-52, 1989.

D. H. Mathews, J. Sabina, M. Zuker & D. H. Turner. Expanded Sequence Dependence of Thermodynamic Parameters Improves Prediction of RNA Secondary Structure J. Mol. Biol. 288, 911-940, 1999.

E. Walter, D. H. Turner, J. Kim, M. H. Lyttle, P. Müller, D. H. Mathews & M. Zuker. Coaxial stacking of helixes enhances binding of oligoribonucleotides and improves predictions of RNA folding. Proc. Natl. Acad. Sci. USA 91, 9218-9222, 1994.

D. H. Mathews, D. H. Turner & M. Zuker. RNA Secondary Structure Prediction. In Current Protocols in Nucleic Acid Chemistry S. Beaucage, D. E. Bergstrom, G. D. Glick, and R. A. Jones eds., John Wiley & Sons, New York, 11.2.1-11.2.10, 2007.

D. H. Mathews, S. J. Schroeder, D. H. Turner & M. Zuker. Predicting RNA Secondary Structure. In The RNA World, R. F. Gesteland, T. R. Cech and J. F. Atkins eds., 3rd edition, Cold Spring Harbor Laboratory Press, Cold Spring Harbor, N.Y., Chapter 22, 2006.

D. H. Mathews & M. Zuker. Predictive Methods Using RNA Sequences. In Bioinformatics: A Practical Guide to the Analysis of Genes and Proteins, A. Baxevanis and F. Ouellette eds., 3rd edition, John Wiley & Sons, New York, Chapter 7, 2005.

D. H. Mathews, M. D. Disney, J. L. Childs, S. J. Schroeder, M. Zuker & D. H. Turner. Incorporating chemical modification constraints into a dynamic programming algorithm for prediction of RNA secondary structure. Proc. Natl. Acad. Sci. USA 101 (19), 7287-7292, 2004.

M. Zuker & D. Sankoff. RNA Secondary Structures and their Prediction. Bull. Mathematical Biology 46, 591-621, 1984.

M. Zuker & P. Stiegler. Optimal computer folding of large RNA sequences using thermodynamics and auxiliary information. Nucleic Acids Res. 9, 133-148, 1981.

J.-M. Rouillard, M. Zuker & E. Gulari. OligoArray 2.0: design of oligonucleotide probes for DNA microarrays using a thermodynamic approach. Nucleic Acids Res. 31 (12), 3057-3062, 2003.

J.-M. Rouillard, C. J. Herbert & M. Zuker. OligoArray: Genome-scale oligonucleotide design for microarrays. Bioinformatics 18 (3), 486-487, 2002.

RNA secondary structure prediction by centroids in a Boltzmann weighted ensemble, Ye Ding, Chi Yu Chan, and Charles E. Lawrence, RNA 2005. 11: 1157-1166

Oligonucleotide synthesis: methods and applications, Volume 288 of Methods in molecular biology, Piet Herdewijn, Humana Press, 2005

Principles of Nucleic Acid Structure, Stephen Neidle, 2008 Elsevier Inc, ISBN: 978-0-12-369507-9

RNA Interference in Mammalian Cells by Chemically-Modified RNA, Biochemistry 2003, 42, 7967-7975

Modified Nucleosides: in Biochemistry, Biotechnology and Medicine, Piet Herdewijn (Editor), Wiley-VCH, 2008 in-Biao Ma, Keqiong Ye & Dinshaw J. Patel Structural basis for overhang specific small interfering RNA recognition by the PAZ domain, Nature, 429, 318 (2004)

Nature Reviews Drug Discovery 8, 129-138 (February 2009) | doi:10.1038/nrd2742, Knocking down barriers: advances in siRNA delivery Simeoni, F. "Insight into the mechanism of the peptide based gene delivery system MPG: implications for delivery of siRNA into mammalian cells." Nucleic acids research 31.11 (2003):2717.

Liu, Z., Winters, M., Holodniy, M. and Dai, H. (2007), siRNA Delivery into Human T Cells and Primary Cells with Carbon-Nanotube Transporters. Angewandte Chemie, 119: 2069-2073. doi: 10.1002/ange.200604295

Aptamer mediated siRNA delivery Nucl. Acids Res. 34(10): e73 doi:10.1093/nar/gkl388

Dynamic PolyConjugates for targeted in vivo delivery of siRNA to hepatocytes PNAS 2007 104 (32) 12982-12987

Bioconjugate Chem., 2007, 18 (5), pp 1391-1396, DOI: 10.1021/bc060367e

T Cell-Specific siRNA Delivery Suppresses HIV-1 Infection in Humanized Mice, Cell, Volume 134, Issue 4, 22 Aug. 2008, Pages 577-586

A universal RNAi-based logic evaluator that operates in mammalian cells, Nature Biotechnology 25, 795-801 (2007)

Molecular Therapy (2010) 18 4, 796-802. doi:10.1038/mt.2009.321, RNA (2010), 16:1275-1284

Molecular Therapy (2006) 13, 494-505

---

What is claimed is:

1. A sensor domain for enzyme-assisted molecular delivery, the sensor domain comprising
   a protection segment comprising an RNA portion, and a targeting domain binding portion presented for covalent attachment to a targeting domain;
   an activation segment comprising a DNA portion complementary to the RNA portion of the protection segment;
   a displacement segment complementary to the protection segment, the displacement segment complementarily binding the protection segment; and
   a toehold segment complementary to a signal polynucleotide,
   wherein the protection segment, displacement segment, and activation segment are configured so that upon complementary binding of the signal polynucleotide to the toehold segment, the displacement segment is displaced from the protection segment and the DNA portion of the activation segment complementarily binds the RNA portion of the protection segment to provide an RNAase H binding site presented for binding;
   wherein the targeting domain binding portion and the RNA portion of the protection segment are configured to allow release of the targeting domain upon cleavage of the RNAase H binding site;
   wherein each of the displacement segment, the protection segment, the activation segment and the toehold segment have a 5' terminus and a 3' terminus, and
   wherein the 5' of the activation segment is adjacent to the 3' terminus of the protection segment, the 3' terminus of the activation segment is adjacent to the 5' terminus of the displacement segment, the 3' terminus of the displacement segment is adjacent to the 5' terminus of the toehold segment.

2. The sensor domain of claim 1, wherein the targeting domain binding portion and the activation domain are located at opposite sides of the RNA portion of the protection segment.

3. The sensor domain of claim 1, wherein the displacement segment complementary binding to the protection segment results in a duplex polynucleotide having a Tm of at least about 25° C. and the complementary binding of the signal polynucleotide to the toehold segment, results in a duplex polynucleotide having a Tm of at least about 25° C.

4. The sensor domain of claim 1, wherein the complementary binding of the signal polynucleotide to the toehold segment results in a duplex polynucleotide having at least 3 consecutive base pairs.

5. A method to provide a molecular complex for enzyme-assisted molecular delivery, the method comprising
   contacting the sensor domain of claim 1, with the targeting domain, the targeting domain being configured for covalent attachment to the targeting domain binding portion of the protection segment of the sensor domain of claim 1, the contacting performed for a time and under condition to allow covalent attachment of the targeting domain to the targeting domain binding portion of the protection segment in a molecular complex configured to release the targeting domain.

6. A system for providing a molecular complex for enzyme-assisted molecular delivery, the system comprising
   the sensor domain of claim 1 and a targeting domain, the targeting domain being configured for covalent attachment to the targeting domain binding portion of the protection segment of the sensor domain of claim 1, to provide a molecular complex wherein the targeting domain is bound to the sensor domain of claim 1 through covalent attachment to the targeting domain binding portion of the protection segment of the sensor of claim 1, the molecular complex configured to release the targeting domain upon cleavage of the RNAase H binding site.

7. A molecular complex for enzyme-assisted molecular delivery, the molecular complex comprising:
   a targeting domain;
   a sensor domain, the sensor domain comprising
   a protection segment comprising an RNA portion,
   an activation segment comprising a DNA portion complementary to the RNA
   portion of the protection segment;
   a displacement segment complementary to the protection segment, the displacement segment complementarily binding the protection segment; and
   a toehold segment complementary to a signal polynucleotide wherein the sensor domain is bound to the targeting domain through covalent attachment of the targeting domain to the protection segment of the sensor domain at a targeting domain binding portion configured to allow release of the targeting domain upon cleavage of the RNAase H binding site;

wherein the protection segment, displacement segment, and activation segment are configured so that upon binding of the signal polynucleotide, the displacement segment is displaced from the protection segment and the DNA portion of the activation segment complementarily binds the RNA portion of the protection segment to provide an RNAase H binding site presented for binding;

wherein each of the displacement segment, the protection segment, the activation segment and the toehold segment have a 5' terminus and a 3' terminus, and wherein the 5' of the activation segment is adjacent to the 3' terminus of the protection segment, the 3' terminus of the activation segment is adjacent to the 5' terminus of the displacement segment, the 3' terminus of the displacement segment is adjacent to the 5' terminus of the toehold segment.

8. The molecular complex of claim 7, wherein the targeting domain comprises a double stranded polynucleotide.

9. The molecular complex of claim 8, wherein the targeting domain is configured to interfere with a target intracellular process of the cells through RNAi in presence of the signal polynucleotide.

10. The molecular complex of claim 9, wherein the targeting domain comprises siRNA, microRNA and additional duplex structure suitable to be used in connection with RNA interfering.

11. A method for enzyme-assisted molecular delivery, the method comprising
contacting the molecular complex of claim 7, with the signal polynucleotide and the RNAase H for a time and under condition to allow release of the targeting domain from the molecular complex.

12. A system for enzyme-assisted molecular delivery, the system comprising:
at least two of:
one or more molecular complexes of claim 7;
a signal polynucleotide complementary to the toehold segment of the one
or more molecular complexes of claim 7; and
an RNAase H ; for simultaneous, combined or sequential use to control release of the targeting domain from the one or more molecular complexes of claim 7.

13. An activatable molecular complex comprising
a targeting domain and
a sensor domain, the sensor domain comprising
a protection segment comprising an RNA portion;
an activation segment comprising a DNA portion complementary to the RNA portion of the protection segment;
a displacement segment complementary to the protection segment; and
a toehold segment complementary to a signal polynucleotide the activatable molecular complex configured to exhibit a first conformation and a second, activated, conformation wherein,
in the first conformation the protection segment covalently attaches the targeting domain, the displacement segment complementarily binds the RNA portion of the protection segment, and the toehold segment and at least a portion of the activation segment are presented for binding to complementary molecules;
in the second, activated, conformation the displacement segment and the toehold segment complementary bind the signal polynucleotide, the RNA portion of the protection segment complementary binds the DNA portion of the activation segment to provide an RNAase H binding site presented for binding, and the targeting domain is attached to the protection segment in a configuration cleavable upon cleavage of the RNAase binding site;

wherein each of the displacement segment, the protection segment, the activation segment and the toehold segment have a 5' terminus and a 3' terminus, and wherein the 5' of the activation segment is adjacent to the 3' terminus of the protection segment, the 3' terminus of the activation segment is adjacent to the 5' terminus of the displacement segment, the 3' terminus of the displacement segment is adjacent to the 5' terminus of the toehold segment.

14. The activatable molecular complex of claim 13, wherein in presence of a signal polynucleotide, the second activated conformation has a free energy of at least about 5 kcal/mol lower than the free energy of the first inactive conformation.

15. The activatable molecular complex of claim 13, wherein in the first conformation the displacement segment and the protection segment form a double stranded duplex, the duplex being up to 30 bp in length.

16. The activatable molecular complex of claim 15, wherein the duplex comprise at least about 5% 2'-O-methyl modifications or one or two mismatches.

17. A method for enzyme-assisted molecular delivery, the method comprising
contacting the molecular complex of claim 13, with a signal polynucleotide complementary to the toehold segment of the molecular complex of claim 13 and an RNAase H for a time and under condition to allow release of the targeting domain from the molecular complex of claim 13.

18. A system for controlled release of a targeting domain from an activatable molecular complex, the system comprising
at least two of:
one or more activatable molecular complexes of claim 13:
a signal polynucleotide complementary to the toehold segment of the one or more activatable molecular complexes of claim 13; and
an RNAase H, for simultaneous combined or sequential use to control release of the targeting domain from the molecular complex of claim 13.

19. A method for controlled activation of a molecular complex, the method comprising
contacting the activatable molecular complex of claim 13 in the first condition, with a signal polynucleotide complementary to the toehold segment to allow switching of the molecular complex from the first condition to the second activated condition of the activatable molecular complex.

20. The method of claim 19, wherein the contacting is performed by providing the activatable molecular complex a expressing the signal polynucleotide.

21. The method of claim 20 wherein the providing is performed by administering the activatable molecular complex to an individual in vivo.

22. An activated molecular complex, the activated molecular complex comprising
a targeting domain; and
a sensor domain, the sensor domain comprising
a protection segment comprising an RNA portion;
an activation segment comprising a DNA portion complementary to the RNA portion of the protection segment;

a displacement segment complementary to the protection segment; and a toehold segment complementary to a signal polynucleotide wherein the displacement segment and the toehold segment complementary bind the signal polynucleotide, the RNA portion of the protection segment complementary binds the DNA portion of the activation segment to provide an RNAase H binding site presented for binding, and the targeting domain is attached to the protection segment in a configuration cleavable upon cleavage of the RNAase binding site wherein each of the displacement segment, the protection segment, the activation segment and the toehold segment have a 5' terminus and a 3' terminus, and wherein the 5' of the activation segment is adjacent to the 3' terminus of the protection segment, the 3' terminus of the activation segment is adjacent to the 5' terminus of the displacement segment, the 3' terminus of the displacement segment is adjacent to the 5' terminus of the toehold segment.

23. A method for enzyme-assisted molecular delivery, the method comprising contacting the activated molecular complex of claim 22 with a signal polynucleotide complementary to the toehold segment of the activated molecular complex of claim 22 and with an RNAase H for a time and under condition to allow release of the targeting domain from the activated molecular complex.

24. The method of claim 23, wherein the contacting is performed by providing the activated molecular complex directly to a cell expressing the signal polynucleotide.

25. A composition comprising one or more of the sensor domains of claim 1 together with a suitable vehicle.

26. A composition, comprising one or more of the molecular complex of claim 8 or one or more of the activatable molecular complex of claim 13 together with a suitable vehicle.

27. A method for treating a disease in an individual through enzyme-assisted signal activated molecular delivery in cells, the method comprising:

administering to the individual an effective amount of one or more of the molecular complexes of claim 4 or one or more of the activatable molecular complex of claim 13.

28. The sensory domain of claim 1, wherein the DNA portion of the activation segment is no longer than 10 nucleotides.

29. A sensor domain for enzyme-assisted molecular delivery, the sensor domain comprising a protection segment comprising an RNA portion, and a targeting domain binding portion presented for covalent attachment to a targeting domain;

an activation segment comprising a DNA portion complementary to the RNA portion of the protection segment;

a displacement segment complementary to the protection segment, the displacement segment complementarily binding the protection segment; and a toehold segment complementary to a signal polynucleotide, wherein the protection segment, displacement segment, and activation segment are configured so that upon complementary binding of the signal polynucleotide to the toehold segment, the displacement segment is displaced from the protection segment and the DNA portion of the activation segment complementarily binds the RNA portion of the protection segment to provide an RNAase H binding site presented for binding;

wherein the targeting domain binding portion and the RNA portion of the protection segment are configured to allow release of the targeting domain upon cleavage of the RNAase H binding site, and wherein each of the displacement segment, the protection segment, the activation segment and the toehold segment have a 5' terminus and a 3' terminus, and wherein the 5' terminus of the activation segment is adjacent to the 3' terminus of the protection segment, the 3' terminus of the activation segment is adjacent to the 5' terminus of the toehold segment, and the 3' terminus of the toehold segment is adjacent to the 5' terminus of the displacement segment.

30. A sensor domain for enzyme-assisted molecular delivery, the sensor domain comprising a protection segment comprising an RNA portion, and a targeting domain binding portion presented for covalent attachment to a targeting domain;

an activation segment comprising a DNA portion complementary to the RNA portion of the protection segment;

a displacement segment complementary to the protection segment, the displacement segment complementarily binding the protection segment; and a toehold segment complementary to a signal polynucleotide, wherein the protection segment, displacement segment, and activation segment are configured so that upon complementary binding of the signal polynucleotide to the toehold segment, the displacement segment is displaced from the protection segment and the DNA portion of the activation segment complementarily binds the RNA portion of the protection segment to provide an RNAase H binding site presented for binding;

wherein the targeting domain binding portion and the RNA portion of the protection segment are configured to allow release of the targeting domain upon cleavage of the RNAase H binding site, wherein each of the displacement segment, the protection segment, the activation segment and the toehold segment have a 5' terminus and a 3' terminus, and wherein the 5' terminus of the toehold segment is adjacent to the 3' terminus of the protection segment, the 3' terminus of the toehold segment is adjacent to the 5' terminus of the displacement segment, and the 3' terminus of the displacement segment is adjacent to the 5' terminus of the activation segment.

31. A sensor domain for enzyme-assisted molecular delivery, the sensor domain comprising a protection segment comprising an RNA portion, and a targeting domain binding portion presented for covalent attachment to a targeting domain;

an activation segment comprising a DNA portion complementary to the RNA portion of the protection segment;

a displacement segment complementary to the protection segment, the displacement segment complementarily binding the protection segment; and a toehold segment complementary to a signal polynucleotide, wherein the protection segment, displacement segment, and activation segment are configured so that upon complementary binding of the signal polynucleotide to the toehold segment, the displacement segment is displaced from the protection segment and the DNA portion of the activation segment complementarily binds the RNA portion of the protection segment to provide an RNAase H binding site presented for binding;

wherein the targeting domain binding portion and the RNA portion of the protection segment are configured to allow release of the targeting domain upon cleavage of the RNAase H binding site, wherein each of the displacement segment, the protection segment, the activation segment and the toehold segment have a 5' terminus and a 3' terminus, and wherein the 5' terminus of the activation segment is adjacent to the 3' terminus of the protection segment, the 3' terminus of the activation segment is arranged as a single strand overhang presented for binding, and the 3' terminus of the displacement segment is adjacent to the 5' terminus of the toehold segment.

32. A molecular complex for enzyme-assisted molecular delivery, the molecular complex comprising:

a targeting domain;

a sensor domain, the sensor domain comprising a protection segment comprising an RNA portion, an activation segment comprising a DNA portion complementary to the RNA portion of the protection segment;

a displacement segment complementary to the protection segment, the displacement segment complementarily binding the protection segment; and a toehold segment complementary to a signal polynucleotide wherein the sensor domain is bound to the targeting domain through covalent attachment of the targeting domain to the protection segment of the sensor domain at a targeting domain binding portion configured to allow release of the targeting domain upon cleavage of the RNAase H binding site;

wherein the protection segment, displacement segment, and activation segment are configured so that upon binding of the signal polynucleotide, the displacement segment is displaced from the protection segment and the DNA portion of the activation segment complementarily binds the RNA portion of the protection segment to provide an RNAase H binding site presented for binding, wherein each of the displacement segment, the protection segment, the activation segment and the toehold segment have a 5' terminus and a 3' terminus, and wherein the 3' terminus of the activation segment is adjacent to the 5' terminus of the targeting domain, and the 5' terminus of the activation domain is a arranged as a single stranded overhang presented for binding, the 5' terminus of the toehold segment is adjacent to the 3' terminus of the protection segment, and the 3' terminus of the toehold segment is adjacent to the 5' terminus of the displacement segment.

33. A molecular complex for enzyme-assisted molecular delivery, the molecular complex comprising:

a targeting domain;

a sensor domain, the sensor domain comprising a protection segment comprising an RNA portion, an activation segment comprising a DNA portion complementary to the RNA portion of the protection segment;

a displacement segment complementary to the protection segment, the displacement segment complementarily binding the protection segment; and a toehold segment complementary to a signal polynucleotide wherein the sensor domain is bound to the targeting domain through covalent attachment of the targeting domain to the protection segment of the sensor domain at a targeting domain binding portion configured to allow release of the targeting domain upon cleavage of the RNAase H binding site, wherein the protection segment, displacement segment, and activation segment are configured so that upon binding of the signal polynucleotide, the displacement segment is displaced from the protection segment and the DNA portion of the activation segment complementarily binds the RNA portion of the protection segment to provide an RNAase H binding site presented for binding, wherein each of the displacement segment, the protection segment, the activation segment and the toehold segment have a 5' terminus and a 3' terminus, and wherein the 5' of the activation segment is a single stranded overhang presented for binding, the 3' terminus of the protection segment is covalently attached to the 5' terminus of the displacement segment through a polynucleotide linker, and the 3' terminus of the displacement segment is adjacent to the 5' terminus of the toehold segment.

* * * * *